(12) United States Patent
Heldman et al.

(10) Patent No.: US 7,887,833 B2
(45) Date of Patent: Feb. 15, 2011

(54) AMPHIPHILIC COMPOUNDS AND VESICLES LIPOSOMES FOR ORGAN-SPECIFIED DRUG TARGETING

(75) Inventors: Eliahu Heldman, Rehovot (IL); Charles Linder, Rehovot (IL); Sarina Grinberg, Meitar (IL); Victoria Kolot, Beer-Sheva (IL); Eleonora Shaubi, Beer-Sheva (IL)

(73) Assignee: Ben-Gurion University of the Negev Research and Development Authority, Beer-Sheva (IL)

( * ) Notice: Subject to any disclaimer, the term of this patent is extended or adjusted under 35 U.S.C. 154(b) by 1257 days.

(21) Appl. No.: 10/497,705

(22) PCT Filed: Dec. 4, 2002

(86) PCT No.: PCT/IL02/00977

§ 371 (c)(1),
(2), (4) Date: Feb. 7, 2005

(87) PCT Pub. No.: WO03/047499

PCT Pub. Date: Jun. 12, 2003

(65) Prior Publication Data

US 2006/0039962 A1   Feb. 23, 2006

Related U.S. Application Data

(60) Provisional application No. 60/334,940, filed on Dec. 4, 2001, provisional application No. 60/395,813, filed on Jul. 16, 2002.

(51) Int. Cl.
*A61K 9/127* (2006.01)
*C07C 231/00* (2006.01)
*C07C 229/00* (2006.01)

(52) U.S. Cl. .......................... 424/450; 554/37; 554/103

(58) Field of Classification Search ................ 424/450; 554/37, 103
See application file for complete search history.

(56) References Cited

U.S. PATENT DOCUMENTS 5,270,053 A   12/1993   Schneider et al.

(Continued)

FOREIGN PATENT DOCUMENTS

GB   2177092 A   1/1987

(Continued)

OTHER PUBLICATIONS

Bayder et al(International Journal of Cosmetic Science, Novel quaternary ammonium salts derived from triglycerides and their application in skin and hair products, 1991, 13, pp. 169-190).*

(Continued)

*Primary Examiner*—Frederick Krass
*Assistant Examiner*—Snigdha Maewall
(74) *Attorney, Agent, or Firm*—Browdy and Neimark, PLLC

(57) ABSTRACT

An amphiphilic compound is provided capable of forming vesicles or liposomes, said amphiphilic compound having at least one headgroup containing a selectively cleavable group or moiety such as a residue of a choline or phenylalanine derivative, and at least one hydrogen-bonding group located either within said headgroup and/or in close proximity thereto. The cleavable group or moiety is cleaved under selective conditions including change of chemical, physical or biological environment and is preferably cleaved enzymatically in a biological environment such as the brain or the blood. Vesicles or liposomes made from said amphiphilic compounds are suitable for delivery of a therapeutic substance or a diagnostic agent specifically to a target organ or tissue, or for delivery of a nucleic acid for gene therapy.

25 Claims, 3 Drawing Sheets

U.S. PATENT DOCUMENTS

| | | | |
|---|---|---|---|
| 5,767,298 | A | 6/1998 | Daleke |
| 5,939,096 | A * | 8/1999 | Clerc et al. ................. 424/450 |
| 6,087,325 | A | 7/2000 | Meers et al. |
| 6,217,886 | B1 * | 4/2001 | Onyuksel et al. ............ 424/401 |
| 6,294,191 | B1 | 9/2001 | Meers et al. |

FOREIGN PATENT DOCUMENTS

| | | |
|---|---|---|
| WO | 9734582 A1 | 9/1997 |
| WO | 9809600 A2 | 3/1998 |
| WO | 0105375 A1 | 1/2001 |
| WO | 02055011 A2 | 7/2002 |

OTHER PUBLICATIONS

Aver'yanov et al.,"Esterification of Dicarboxylic Acids with Benzyl Alcohol under the Action of the Microwave Radiation" Russian Journal of General Chemistry, 78(10):1920-1923 (2008).

Bangham et al., "Diffusion of univalent ions across the lamellae of swollen phospholipids", J. Mol. Biol., 13(1):238-252 (1965).

Baumann et al., "Natural Fats and Oils—Renewable Raw Materials for the Chemical Industry" Angewandte Chemie International Edition in English., 27:1:41-62 (1988).

Baydar et al., "Novel quaternary ammonium salts derived from triglycerides and their application in skin and hair products" International Journal of Cosmetic Science 13:169-190 (1991).

Biermann et al., "New Synthesis with Oils and Fats as Renewable Raw Materials for the Chemical Industry" Angew. Chem. Intl. Ed. 39: 2206-2224 (2000).

Chan et al., "Acid-cleavable polymeric core-shell particles for delivery of hydrophobic drugs" Journal of Controlled Release 115:197-207 (2006).

May, Clayton A., "Epoxy resins: chemistry and technology" 2nd Ed. M. Dekker, New York, NY (only relevant pp. 285-293) (1988).

Dai et al., "Synthesis and Characterization of the Different Soy-Based Polyols by Ring Opening of Epoxidizing Soybean Oil with Methanol, 1,2-Ethanediol and 1,2-Propanediol" J Am Oil Chem Soc 86:261-267 (2009).

Furuta et al.,"Design and synthesis of artificial phospholipid for selective cleavage of integral membrane protein", Chem.Commun., pp. 4575-4577 (2005).

Gast et al.,"Polyester amides from linseed oil for protective coatings; low acid-value polymers", J. Am. Oil Chem. Soc. 43(6), 418-421 (1966).

S. Grinberg et al.,"New Chemical derivatives based on Vernonia galamensis oil" Industrial Crops and Products 3:113-119 (1994).

S. Grinberg et al., "Novel Cationic Amphiphilic Derivatives from Vernonia Oil: Synthesis and Self-Aggregation into Bilayer Vesicles, Nanoparticles, and DNA Complexants" Langmuir 21:7638-7645 (2005).

S. Grinberg et al., "Synthesis of novel cationic bolaamphiphiles from vernonia oil and their aggregated structures" Chemistry and Physics of Lipids, 153:85-97 (2008).

Guidotti et al., "Heterogeneous catalytic epoxidation of fatty acid methyl esters on titanium-grafted silicas" Green Chemistry 5:421-424 (2003).

Halldorsson et al., "Chemoenzymatic synthesis of structured triacylglycerols by highly regioselective acylation" Tetrahedron 59: 9101-9109 (2003).

Hayakawa et al., "The C-2 Selective Azide Opening Reaction of trans-2,3-Epoxy Alcohols by NaN3 and PhB(OH)2" Tetrahedron Letters 40:4589-4592 (1999).

Heidelberger et al.,"Amidines as Intermediates in Transamidation Reactions" Helv. Chim. Acta, 64, 399. (1981).

Itoi et al., "Epoxidation of Fatty Acid Esters with Aqueous Hydrogen Peroxide in the Presence of Molybdenum Oxide-Tributyltin Chloride on Charcoal Catalyst" Bull. Chem. Soc. Jpn., 59:3941-3943 (1986).

Jordan et al., "Low temperature aminolysis of methyl stearate catalyzed by sodium methoxide" J. Am. Oil Chem. Soc. 38:600-605 (1961).

Kramer et al., "The 'Zip' Reaction: A New Method for Ring Expansion; Synthesis of 17- and 21- Membered Polyaminolactams" Angew. Chem. Int. Ed.Engl 16(12): 861-862 (1977).

Lee and Neville., "Handbook of Epoxy Resins" McGraw-Hill, New York, NY (only relevant pp. 3-12, 5-4 through 5-6, and 5-33 through 5-39 (1967).

Leplyanin et al., "Reaction of methacrylic acid with epoxy compounds" Russian Chemical Bulletin (33): 1319-1321 (1984).

Ljunger et al., "Lipase catalyzed acylation of glucose", Biotechnol. Lett., 16, 1167-1172 (1994).

Maruoka et al., "A Highly Regio- and Stereoselective Ring-Opening of 2,3-Epoxy Alcohols With Trimethylsilyl Azide-Diethylaluminum Fluoride System" Chemistry Letters., 599-602 (1985).

Menger et al., "Specific Enzyme-Induced Decapsulation" J. Am. Chem. Soc., 113: 5461-5468 (1991).

Metzger et al., "New Type of Skipped Oligoaziridines: Synthesis of New Fatty Acid Derivatives Containing Aziridine Functions" Eur. J. Org. Chem pp. 661-664 (1999).

Pascu et al., "Interfacial polymerization of an epoxy resin and carboxylic acids for the synthesis of microcapsules" Polym Int 57:995-1006 (2008).

Rusch gen. Klaas et al., "Lipase-catalyzed preparation of peroxy acids and their use for epoxidation" Journal of Molecular Catalysis A: Chemical 117:311-319 (1997).

Tang., "Boric Acid Catalyzed Amide Formation From Carboxylic Acids and Amines: N-Benzyl-4-Phenylbutyramide [(Benzenebutanamide, N-(phenylmethyl)-)]" Organic Syntheses, 81:262 (2005).

Wang et al. "Drug delivery: principles and applications" Wiley-Interscience, Hoboken, NJ (cover-page and table of content only) (2005).

Werner et al.,"The preparation of ethylamine and diethylamine"J. Chem Soc., 899-902 (1981).

Wicks et al., "Organic coatings: science and technology." 3rd Ed. Wiley-Interscience, Hoboken, NJ, (cover-page and table of content only) (2007).

Xu et al., "Esterase-catalyzed dePEGylation of pH-sensitive vesicles modified with cleavable PEG-lipid derivatives" Journal of Controlled Release 130:238-245 (2008).

Yan et al., "Regioselective lipase-catalyzed synthesis of glucose ester on a preparative scale" Eur. J. Lipid Sci. Technol., 103:583-587 (2001).

Yoo et al., "Enzymatic synthesis of sugar fatty acid esters" J. Ind. Eng. Chem,13:1-6 (2007).

Supplementary European Search Report in corresponding European application, mailed Oct. 13, 2010.

* cited by examiner

AMPHIPHILIC COMPOUNDS AND VESICLES LIPOSOMES FOR ORGAN-SPECIFIED DRUG TARGETING

FIELD OF THE INVENTION

The present invention relates to novel amphiphilic derivatives and to vesicles and liposomes made therefrom for site-directed delivery of therapeutic agents and specific release thereof at a target tissue, while being insulated from non-relevant tissues. The invention is particularly suitable for delivering toxic agents, or agents with short biological life time or low bioavailability, to the target organ.

BACKGROUND OF THE INVENTION

Therapeutic efficacy of many biologically active substances has been hindered due to the difficulty or incapability to deliver the substance in therapeutically active, or sufficient amounts to the patient's organ or tissue to be treated. One of the main difficulties with respect to the efficient delivery of such substances is presented by biological barriers with low or no permeability to many substances.

Compounds designed to facilitate intracellular delivery of biologically active molecules must interact with both polar and non-polar components within the body, and therefore, should typically contain themselves both polar and non-polar domains. For this purpose, amphiphilic compounds containing polar and hydrophobic (non-polar) domains and, particularly, cationic amphiphiles have been found suitable for intracellular delivery of drugs.

Vesicles from phospholipid amphiphiles known as liposomes are used to deliver drugs for treating certain cancers and microbial infections. For example, the therapeutic efficacy of some important chemotherapeutic and antibiotic agents can be enhanced by encapsulating them in liposomes, which have an acceptable blood circulatory lifetime and improved access to diseased sites via increased vascular porosity (Lasic, 1996). However the mode of delivery in these cases is passive, and the goal of targeting with controlled release still remains elusive.

Targeted controlled release of biologically active materials for therapeutic applications is under continuous development using different drug delivery platforms such as micelles, emulsions, complexants, prodrugs and vesicles. Vesicles, made from synthetic amphiphiles, as well as liposomes, made from synthetic or natural phospholipids, are considered very promising approaches because the therapeutic agent is totally isolated from the environment, each vesicle or liposome delivers many molecules, and the surface properties of the vesicle or liposome can be modified for biological stability, enhanced penetration through biological barriers and targeting, independent of the physico-chemical properties of the encapsulated drug. However, in spite of the serious efforts invested in making vesicles with targeted controlled release properties, vesicles with good mechanical, chemical and biological stability needed for many applications have not yet been produced.

Three approaches are currently being pursued to improve temporal control of drug release from vesicles or liposomes: (i) physical approaches such as temperature, pH or target-binding sensitive-induced phase changes; (ii) chemical approaches, which try to destabilize liposomes at a particular location; and (iii) biological approaches, which use surface attached targeting moieties (Lasic, 1998).

Spatial control of drug release has been attempted by cellular targeting in physically accessible sites by liposomes containing antibody molecules attached to liposome surface by polymer chains. The state of the art is ambivalent about the potential of antibodies and surface ligands for targeted delivery. It seems that problems of accessibility to a particular tissue and cells as well as overlooked severity of triggered immune response to the host organism by antibody- or lectin-coated liposomes, makes this approach problematic.

Enzyme-labile liposomes have been investigated as a model for site-directed liposomal drug delivery system. This approach takes into account that certain pathological cells produce excessive amounts of a particular enzyme, for example, bone cancer cells produce alkaline phosphatase, and neuroblastoma cells produce acetylcholinesterase. In one approach, small unilamellar vesicles with acetylcholine headgroups were made and shown to disrupt in vitro in the presence of acetylcholinesterase (Menger and Johnston, 1991).

Elastase is of interest because of its ubiquitous involvement in inflammatory and tumorigenic conditions. A peptide-lipid conjugate sensitive to enzymatic cleavage was designed and reported to generate liposomes that could be triggered to fuse by enzymatic activation. In effect, covalent linkage of dioleoyl phosphatidylethanolamine to an elastase substrate, N-acetyl-ala-ala, resulted in a cleavable peptide-lipid with no intrinsic fusogenic activity. In addition, the ability of elastase to recognize a simple peptide substrate simplifies coupling as well as potentially limiting the immunogenicity of the peptide-lipid (Pak et al., 1998).

U.S. Pat. No. 6,087,325 describes peptide-lipid conjugates that are incorporated into liposomes so as to selectively destabilize the liposomes in the vicinity of target peptidase-secreting cells, and hence to deliver the liposomes to the vicinity of the target cells, or directly into the cells. The liposomes can thus be used to treat mammals for diseases, disorders or conditions such as tumors, microbial infection and inflammation characterized by the occurrence of peptidase-secreting cells.

Vesicles and liposomes may also be destabilized by changes in pH at the target site. For example, WO 01/05375 describes amphiphilic lipid compounds having an acid or oxidative labile vinyl ether linked hydrophilic headgroup and liposomes made therewith, of a given stability for circulation and of a desired release rate profile or fusogenicity to suit a particular therapeutic or diagnostic indication. The stabilized liposomes or vesicles are said to be readily destabilized at a given site because of changes in the chemical environment such as pH or oxidants.

U.S. Pat. No. 6,294,191 describes liposomes containing one or more N-acylated phosphatidylethanolamine moieties for localizing the delivery of bioactive agents to cells.

The transport of compounds from the blood to target tissues is restricted by biological barriers such as the blood-brain-barrier (BBB). Drug delivery to the brain is particularly hampered because of the tight junctions between adjacent endothelial cells of brain capillaries, which form the BBB. However, some lipid soluble substances can penetrate passively across this barrier, whereas hydrophilic and ionic substances [e.g., amino acids] are transported by a specific carrier transport system. Therefore, it is possible to improve the entry of certain substances into the central nervous system (CNS) by regulating these transporters.

Efforts have been made to enhance transport via the BBB by conjugating drugs with CNS permeable moieties. For example, attempts have been made in correcting disorders affecting the CNS system by increasing BBB permeability of exogenous biological compounds such as proteins or specific nucleic acid sequences by conjugating them with lipids (Chopineau et al., 1998). Long alkyl chains, such as fatty acids, due to their hydrophobicity and low toxicity, are good potential candidates that may enhance BBB permeability of drugs when covalently bound to them. Another example of forming conjugates with a vector or carrier that enhance transport across the BBB is the utilization of membrane-bound enzymes to release a bioactive peptide from a highly lipophilic triglyceride peptide carrier (Patel et al., 1997).

The methods above and others, however, do not encapsulate the active agent and are not selective as the conjugated molecule is adsorbed and degraded in several biological compartments. Some further studies have been reported on the use of liposomes for crossing the BBB such as in corporation of enzymes into the liposomes (Naoi and Yagi et. al, 1980); using PC cholesterol and sulfatides, for delivery of their contents to rat brains (Yagi et. al, 1982); using liposomes composed of PC cholesterol and p-aminophenyl-alpha-mannopyranoside to deliver [3H]-galactocerebroside to brain lysosomes and to glial cells because of recognition of mannose residues by the cells of the BBB (Umezawa and Eto, 1988); and a study in which cAMP phosphodiesterase [PDE] was iodinated, entrapped in either dehydration-rehydration vesicles or small unilamellar vesicles (SUV's) prepared from PC cholesterol and sulfatides, and delivered to the brain by means of intravenous injection with hyperosmolar mannitol, that was shown to increase the permeability of the liposomes through the BBB (Kozler, 2001).

None of the above approaches of the prior art provide effective targeting to the CNS. In addition, because of poor stability, state of art liposomes release a relatively large amount of the encapsulated active agent into a variety of non-targeted tissues.

SUMMARY OF THE INVENTION

The present invention relates to novel amphiphilic compounds capable of forming vesicles or liposomes, said amphiphilic compound having at least one headgroup containing a selectively cleavable group or moiety and at least one hydrogen-bonding group located either within said headgroup and/or in close proximity thereto.

The selectively cleavable group or moiety is a group or moiety that is cleaved under selective conditions including change of chemical, physical or biological environment such as, but not limited to, change of pH or temperature, oxidative or reducing conditions, and/or, preferably, enzymatic conditions.

Vesicles and liposomes made from amphiphilic compounds of the invention can be used for encapsulating drugs and delivering them, while being encapsulated, to target organs. The vesicles are then disrupted at the target organ and the drugs are released primarily there. The amphiphilic compounds contain groups that form hydrogen bonding when the amphiphiles are organized into vesicles, so that the stability of the vesicles is increased, and headgroups containing selectively cleavable groups or moieties that are hydrolyzed in the target organ or tissue, thus causing the disruption of the vesicles and consequent release of the encapsulated drug. Additional targeting pendants may be introduced to direct the vesicles to the target organ or tissue.

DETAILED DESCRIPTION OF THE INVENTION

Figure 1:
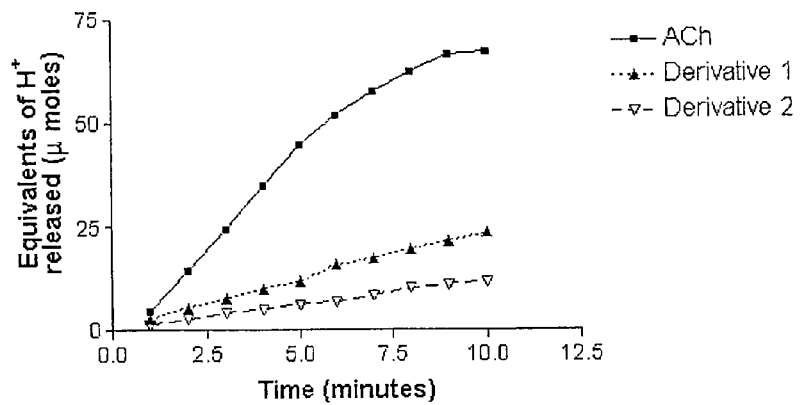
FIG. 1 shows release of $H^+$ during the hydrolysis of acetylcholine (Ach) and Derivatives 1 and 2 by cholinesterase (ChE).

The present invention relates, in one aspect, to amphiphilic compounds capable of forming vesicles or liposomes, said amphiphilic compound having at least one headgroup containing a selectively cleavable group or moiety and at least one hydrogen-bonding group located either within said headgroup and/or in close proximity thereto.

As used herein, the term "selectively cleavable group or moiety" refers to a group or moiety that is cleaved under selective conditions including change of chemical, physical or biological environment such as, but not limited to, selective conditions including change of pH or temperature, oxidative or reducing conditions, and/or enzymatic conditions. The term "removable group" is also used herein to denote a specific functional group within the selectively cleavable group or moiety that is removed from the molecule when the cleavage occurs.

In one preferred embodiment of the invention, the selectively cleavable group is cleaved enzymatically in a biological environment, particularly in the brain or blood, by degradatives enzymes such as hydrolases, esterases, phosphatases, oxidases, decarboxylases, deaminases and isomerases, some of which are restricted to the brain or exist also in the brain and in the periphery. Examples of such enzymes include, but are not limited to, cholinesterases (ChE) such as acetylcholine esterase (ACHE) and aromatic L-amino acid decarboxylase (AADC).

Examples of selectively cleavable groups or moieties that can be used according to the invention include, without being limited to, residues from derivatives of choline and thiocholine such as acetylcholine and thioacetyl choline; residues from derivatives of an aromatic amino acid selected from phenylalanine, tyrosine and tryptophan such as p-aminophenylalanine, levodopa (3,4-dihydroxy-phenylalanine); residues from glutamic acid or aspartic acid; and residues from peptides or derivatives thereof such as enkephaline (cleaved by enkephalinase primarily in the brain), N-acetyl-ala,ala (cleaved by elastase, that is overexpressed in certain types of cancer and aneurysms), peptides that constitute the domains recognized by beta and gamma secretases (which are overexpressed in the brain of Alzheimer's disease patients), and peptides that are recognized by stromelysins (their incorporation into vesicles will release their content in inflammatory sites).

According to the present invention, at least one hydrogen-bonding group such as, but not limited to, —OH, —SH, —NH—, —$N^+H_2$—, —$NH_2$, —$N^+H_3$, —NH—CO—, —O—CO—NH—, —NH—CO—NH—, —C=NOH, —C($NH_2$)=NOH, —C($NH_2$)=NO— and —CO—$NH_2$, is found either within the headgroup containing the selectively cleavable group or moiety and/or in close proximity to the headgroup, thus imparting more stability and other features to the vesicles made from such amphiphilic compounds. By "close proximity" it is meant herein that the hydrogen-bonding group is located at the atom vicinal to the atom of the aliphatic chain to which the headgroup is bound and/or at a distance of up to 6 atoms in the aliphatic chain.

In one embodiment, an amphiphilic compound of the invention has the formula I:

$$X1\text{-}CO\text{—}X2\text{-}X3 \qquad [I]$$

wherein $X1$ is -$Q_1$-R0, wherein $Q_1$ is —NH—, —O—, —S—, or —PO(OH)—O—;

R0 is —X4-X5-X6 or —$(CH_2)_{r'}$—X7;

X2 and X5, the same or different, each is an alkylene chain of at least 5 carbon atoms;

X3 and X6, the same or different, each is an aliphatic chain of at least 5 and at most 18 carbon atoms optionally carrying at least one double bond, said aliphatic chain being substituted by at least one polar, ionic and/or epoxy groups and/or by at least one moiety containing at least one polar, ionic and/or epoxy groups, said at least one polar, ionic and/or epoxy groups and at least one moiety containing at least one polar, ionic and/or epoxy groups being, in relation to their substitutions, in any combination of 1-2, 1-2-3, 1-2-3-4, 1-2-4-5, 1-2-3-4-5, 1-2-4, 1-2-5, 1-3-4, 1-3, 1-5, 1-4, or 1-2-6 positions of the chain, the position 1 being arbitrarily assigned to the substitution most remote from the CO group;

X4 is a spacer group consisting of a linear or branched aliphatic chain of up to 16 carbon atoms, optionally interrupted by $Q_2$ or by —CO-$Q_2$-, wherein $Q_2$ is —NH—, —O—, —S—, or —O—PO(OH)—O—, and optionally containing at least one polar and/or ionic group or at least one moiety containing at least one polar and/or ionic group;

X7 is hydrogen, C6-C14 aryl, preferably phenyl, or a heterocyclic radical;

r' is an integer from o to 12; and wherein at least one polar and/or ionic group and/or at least one moiety containing at least one polar and/or ionic group of X3, X4 and/or X6 is a headgroup, and wherein at least one of said at least one headgroup of X3 and/or X6 or of X4 is a headgroup containing a selectively cleavable group or moiety and at least one hydrogen-bonding group is located within and/or in in close proximity to said headgroup containing a selectively cleavable group or moiety.

In another embodiment, an amphiphilic compound of the invention has the formula II:

$$X6\text{-}X5\text{-}X4\text{-}CO\text{-}Q_1\text{-}X2\text{-}X3 \qquad [II]$$

wherein $Q_1$ is —NH—, —N(CH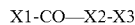, —O—, —S—, or —O—PO(OH)—O—;

X4 is a spacer group consisting of a linear or branched aliphatic chain of up to 16 atoms, optionally interrupted by —CO-$Q_2$-, wherein $Q_2$ is —NH—, —N(CH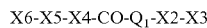, —O—, —S—, or —O—PO(OH)—O—, and optionally containing at least one polar and/or ionic group or at least one moiety containing at least one polar and/or ionic group;

X2 and X5, the same or different, each is an alkylene chain of at least 5 carbon atoms;

X3 and X6, the same or different, each is an aliphatic chain of at least 5 and at most 18 carbon atoms optionally carrying at least one double bond, said aliphatic chain being substituted by at least one polar, ionic and/or epoxy groups and/or by at least one moiety containing at least one polar, ionic and/or epoxy groups, said at least one polar, ionic and/or epoxy groups and at least one moiety containing at least one polar, ionic and/or epoxy groups being, in relation to their substitutions, in any combination of 1-2, 1-2-3, 1-2-3-4, 1-2-4-5, 1-2-3-4-5, 1-2-4, 1-2-5, 1-3-4, 1-3, 1-5, 1-4, or 1-2-6 positions of the chain, the position 1 being arbitrarily assigned to the substitution most remote from the CO group; and wherein at least one polar and/or ionic group and/or at least one moiety containing at least one polar and/or ionic group of X3, X4 and/or X6 is a headgroup, and wherein at least one of said at least one headgroup of X3 and/or X6 or of X4 is a headgroup containing a selectively cleavable group or moiety and at least one hydrogen-bonding group is located within and/or in in close proximity to said headgroup containing a selectively cleavable group or moiety.

In one preferred embodiment, the amphiphilic compounds of the invention of the formula I or II are composed of two fatty acid chains, formed by the —X2-X3 and —X5-X6 groups, each comprising a polar or ionic headgroup containing a selectively cleavable group or moiety, and at least one of the fatty acid chains contains a ionic or polar hydrogen-bonding group in close proximity to said headgroup and/or attached to a site within said headgroup, and the two fatty acid chains are separated by a non-fatty acid midsection or spacer, for example a C2-C16 alkylene chain optionally interrupted by —O—, —S— or —NH—, and each fatty acid chain is bound to the midsection through an amide (a hydrogen-bonding group), ether, ester, thioester, and/or phosphoesters bonds.

In one preferred embodiment, the invention provides amphiphilic compounds of the formula I above that are capable of forming monolayer vesicles, and have the formula Ia:

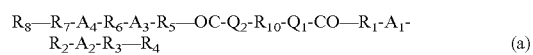 (a)

wherein the chains —CO—$R_1$-$A_1$-$R_2$-$A_2$-$R_3$—$R_4$ and $R_8$—$R_7$-$A_6$-$R_6$-$A_5$-$R_5$—CO— may be derived from the same fatty acid, wherein said fatty acid is selected from vernolic acid (12,13-epoxyoctadec-9-enoic acid), lesquerolic acid (14-hydroxyeicosa-11-enoic acid), ricinoleic acid (12-hydroxyoctadec-9-enoic acid), partially or totally epoxidized linoleic, linolenic, and arachidonic acid, or from a derivative thereof obtained by reaction of the epoxy group and/or of a double bond and/or of a hydroxy group, or the chain $R_8$—$R_7$-$A_6$-$R_6$-$A_5$-$R_5$—CO— may also be derived from a fatty acid selected from lauric, myristic, palmitic, stearic, arachidic, beherric, lignoceric, or undecylenic acid or from a derivative thereof. The sources of some epoxidized and hydroxylated fatty acids are vernonia oil, *lesquerella* oil, castor oil, and epoxidized soya and linseed oil.

In one preferred embodiment, the invention provides an amphiphilic compound of the formula Ia, wherein:

$R_1$ and $R_5$, the same or different, each is —$(CH_2)_n$—;

$A_1$ is selected from —$(CH_2)_{m+2}$—, —CH=CH—$(CH_2)_m$—, —CH=CH—CH($Y_1$)—, —$CH_2$—$CH_2$—CH($Y_1$)—, (—$CH_2$—CH($Y_1$)—$(CH_2)_m$—, —CH($Y_1$)—$CH_2$—$(CH_2)_m$—, —CH($Y_1$)—CH($Y_2$)—$(CH_2)_m$—, wherein $Y_1$ and $Y_2$ each is halogen, —OH, —O—CO—(CH$_2$)$_m$—Y$_3$, —NH—CO—Y$_3$, —SH, —SR$_{11}$, —NH$_2$, or —N(R$_{11}$)(R$_{12}$), or Y$_1$ and Y$_2$ together with the carbon atoms to which they are attached form a 2,3-oxiranylene group; and Y$_3$ is halogen, —OH, —SH, —NH$_2$, or —N(R$_{11}$)(R$_{12}$);

R$_2$ and R$_6$, the same or different, each is C1-C4 alkylene, preferably methylene, optionally substituted by halogen, amino or hydroxy;

A$_2$ is selected from —CH(R$_{13}$)—, —CH$_2$—CH(R$_{13}$)—, —CH(R$_{13}$)—CH$_2$—, —CH(OH)—CH(R$_{13}$)—, —CH(R$_{13}$)—CH(OH)—, —CH(OH)—CH$_2$—CH(OH)—CH(R$_{13}$)—, —CH(OH)—CH$_2$—CH(R$_{13}$)—CH(OH)—, -G1-(C6-C14 arylene)-(CH$_2$)$_q$R$_{14}$, —N(CH$_3$)$_2$R$_{14}$, or —SR$_{14}$;

R$_3$ and R$_7$, the same or different, each is —(CH$_2$)$_o$—;

R$_4$ is H or CH$_3$, and wherein the total sum of carbon atoms in the R$_1$-A$_1$-R$_2$-A$_2$-R$_3$—R$_4$ chain is at most 23;

Q1 is —NH—, —O—, —S—, or —O—PO(OH)—O—;

Q2 is —NH—, —O—, —S—, or —O—PO(OH)—O—;

R$_{10}$ is a group selected from —CH$_2$)$_p$—; —CH$_2$(CH$_3$)—(CH$_2$)$_p$—; —CH(CH$_3$)—(CH$_2$)$_p$—CH(CH$_3$)—; —(CH$_2$—CH$_2$—O—)$_p$—CH$_2$—CH$_2$—; —(CH$_2$—CH$_2$—S—)$_p$—CH$_2$—CH$_2$—; —(CH$_2$—CH$_2$—NH—)$_p$—CH$_2$—CH$_2$—; —C6-C14 arylene-; —(C6-C14 arylene)-R—(C$_6$-C$_{14}$ arylene)- wherein R is C1-C4 alkylene, —C(CH$_3$)$_2$—, —O—, —S—, —NH— or —SO$_2$—;

A$_3$ is as defined for A$_1$, or is —(CH$_2$)$_m$, phenyl or —CH$_2$-phenyl wherein the phenyl ring may be substituted by C1-C4 alkyl and/or by halogen;

A$_4$ is as defined for A$_2$, or is —(CH$_2$)$_m$;

R$_8$ is as defined for R$_4$;

R$_{13}$ is -G1-(CH$_2$)$_m$R$_{14}$ or -G1-CO(CH$_2$)$_m$R$_{14}$;

G1 is —O—, —S—, —NR"—, —CH$_2$NR"—, —CH$_2$S— or —CH$_2$O—, —NH—CO—, —O—CO—NH—, —NH—CO—NH—, —C=NO—, —C(NH$_2$)=NO—, wherein R" is H or C1-C18 alkyl;

R$_{14}$ is either a headgroup containing a selectively cleavable group or moiety, or is as defined for R$_{15}$ or for R$_{15}$ substituted by a selectively cleavable group or moiety;

R$_{11}$ and R$_{12}$, the same or different, each is C1-C18 alkyl optionally substituted by halogen; phenyl or —CH$_2$-phenyl, wherein the phenyl ring may be substituted by C1-C4-alkyl and/or by halogen, and wherein one of R$_{11}$ and R$_{12}$ may be H;

R$_{15}$ is —NH$_2$; —NR$_{11}$R$_{12}$; —N$^+$R$_{11}$R$_{12}$R$_{16}$ wherein R$_{16}$ is as defined for R$_{11}$ and R$_2$; —O—CO—(C2-C6 alkenyl); —O—CO—(CH$_2$)$_r$—NR$_{11}$R$_{12}$; —O—CO—(CH$_2$)$_r$—N$^+$R$_{11}$R$_{12}$R$_{16}$; —O—CO—(CH$_2$)$_r$—COOH; —O—CO—(CH$_2$)$_r$—SO$_3$H; —O—CO—(CH$_2$)$_r$—O—PO(OH)$_2$; —NH—(CH$_2$)$_r$—COOH; —NH—(CH$_2$)$_r$—SO$_3$H; —NH—(CH$_2$)$_r$—O—PO(OH)$_2$; —NH—PO(OH)$_2$; —N$^+$(CH$_3$)$_2$—R$_{17}$; —O—PO(OH)—O—(CH$_2$)$_2$—N$^+$R$_{11}$R$_{12}$R$_{16}$; —O—PO(OH)—O—(CH$_2$)$_2$—NH$_3^+$; —O—PO(OH)—NH—PO(OH)—O—; —O—PO(OH)—O—CH$_2$—CH(NH$_3^+$)—COO$^-$; —CH$_2$—CH=CH$_2$; —CO—CH=CH$_2$; —CO—C(CH$_3$)=CH$_2$; —(CH$_2$)$_r$—COOH; —(CH$_2$)$_r$—O—SO$_2$H; —(CH$_2$)$_r$—O—PO(OH)$_2$; —SR$_{18}$; -G1-(C6-C14 arylene)-NR$_{11}$R$_{12}$; -G1-(C6-C14 arylene)-N$^+$R$_{11}$R$_{12}$R$_{16}$; -G1-(C6-C14 arylene)-COOH; -G1-(C6-C14 arylene)-SO$_3$H; -G1-(C6-C14 arylene)-O—PO(OH)$_2$; -G1-(C6-C14 arylene)-(CH$_2$)$_r$—NR$_{11}$R$_{12}$; -G1-(C6-C14 arylene)-(CH$_2$)$_n$—N$^+$R$_{11}$R$_{12}$R$_{16}$; -G1-(C$_6$-C$_{14}$ arylene)-(CH$_2$)$_r$—COOH; -G1-(C$_6$-C$_{14}$ arylene)-(CH$_2$)$_r$—SO$_3$H;

R$_{17}$ is —CH$_2$—CH=CH$_2$, —CO—CH=CH$_2$, —CO—C(CH$_3$)=CH$_2$, —(CH$_2$)$_q$—N$^+$R$_{11}$R$_{12}$R$_{16}$, —(CH$_2$)$_q$—NH—(CH$_2$)$_q$—SO$_3$H, —(CH$_2$)$_q$—NH—(CH$_2$)$_q$—COOH, —(CH$_2$)$_q$—NH—(CH$_2$)$_q$—O—PO(OH)$_2$, —PO(OH)$_2$, or —O—PO(OH)—O—(CH$_2$)$_2$—N$^+$R$_{11}$R$_{12}$R$_{16}$;

R$_{18}$ is hydrogen, C1-C18 alkyl, C2-C6 alkenyl with a terminal double bond, —CO—CH=CH$_2$, or —CO—C(CH$_3$)=CH—NR$_{11}$R$_{12}$;

n is an integer from 5 to 10; m is an integer from 0 to 4; o is an integer from 0 to 10; p is an integer from 1 to 16; q is an integer from 0 to 3; r is an integer from 1 to 6; and t is an integer from 1 to 14, and salts thereof.

In one embodiment of the present invention, the amphiphilic compounds Ia are symmetric and comprise two identical fatty acid chains, to each of which the same headgroup containing the same selectively cleavable group and the same stabilizing polar hydrogen-bonding group are attached to the aliphatic chains in close proximity. In addition, an additional hydrogen-bonding group may be found within each of the headgroups.

For example, starting from vernolic acid, which acyl residue has the formula:

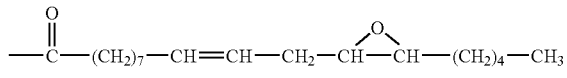

symmetric amphiphilic compounds of the formula Ib can be synthesized by reaction with an alkylene diamine, e.g. ethylene diamine, and opening of the oxiranyl ring with a carboxylic acid derivative, for example:

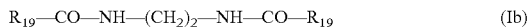

(Ib)

where

R$_{19}$ is —(CH$_2$)$_7$—CH=CH—CH$_2$—CH(OH)—CH(R$_{20}$)—(CH$_2$)$_4$—CH$_3$ and R$_{20}$ is —OCOCH$_2$CH$_2$NH-phenyl-CH$_2$—CH(NH$_2$)—COOH In this example, R$_{20}$ is the headgroup moiety containing the selectively cleavable moiety p-aminophenylalanine that is linked to the fatty acid chain R$_{19}$ through an ester linkage, and said headgroup contains the hydrogen-bonding —NH group at the para position of the phenyl group and another hydrogen-bonding —OH group on the vicinal carbon atom (positions 1-2), both contributing for stabilization.

Instead of ethylene as the spacer X4, another longer linear spacer or, for example, a branched spacer can be formed by reaction with a diamine such as: NH$_2$—CH$_2$—CH(CH$_3$)—CH$_2$—CH(CH$_3$)—CH$_2$—NH$_2$.

In another embodiment, the two fatty acid chains can be linked to the spacer by an ester instead of amide linkages, when the reaction is conducted with a dihydroxy compound such as diethylene glycol, thus obtaining, for example a compound of formula Ic:

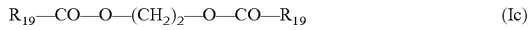

(Ic)

wherein

R$_{19}$ is as defined for compound Ib above.

In a further embodiment, the amphiphilic compound has the formula Id:

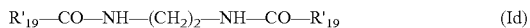

(Id)

where

R′$_{19}$ is —(CH$_2$)$_7$—CH=CH—CH$_2$—CH(OH)—CH(R$_{21}$)—(CH$_2$)$_4$—CH$_3$ and R$_{21}$ is —NHCO—CH$_2$CH$_2$NH-phenyl-CH$_2$—CH(NH$_2$)—COOH In a still further embodiment, the amphiphilic compound has the formula Ie:

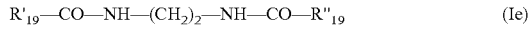

(Ie)

where

R′$_{19}$ is as defined above,

R″$_{19}$ is —(CH$_2$)$_7$—CH=CH—CH$_2$—CH(OH)—CH(R$_{23}$)—(CH$_2$)$_4$—CH$_3$ and R$_{23}$ is —NH—CH$_2$CH$_2$NH-phenyl-CH$_2$—CH(NH$_2$)—COOH In the compounds of the formulas Id and Ie, the headgroup moiety R$_{21}$ or R$_{23}$ containing the p-aminophenylalanine group is linked to the fatty acid chain R′$_{19}$ or R″$_{19}$ through an amido or amino linkage, respectively, and said headgroup contains the hydrogen-bonding —NH group at the para position of the phenyl group and the hydrogen-bonding —CONH— or —NH— group two carbon atoms further, besides the hydrogen-bonding —OH group on the vicinal carbon atom. These compounds can be obtained from vernonia oil by amidation (Id) or aminolysis of the epoxide ring (Ie).

In one preferred embodiment of the present invention, asymmetric amphiphilic compounds are provided in which the aliphatic chains on both sides of the spacer X4 are identical, except for the headgroups, and wherein at least the bulkier headgroup contains the selectively cleavable group or moiety and will be on the outside of the vesicle made therefrom. An example of such an asymmetric compound is a compound of formula If:

$$R_{24}\text{—CO—NH—}(CH_2)_2\text{—NH—CO—}R'_{19} \qquad (If)$$

where

R″$_{19}$ is as defined above, and contains the bulkier headgroup R$_{21}$ with the selectively cleavable moiety —NH—CH$_2$CH$_2$NH-phenyl-CH$_2$—CH(NH$_2$)—COOH R$_{24}$ is —(CH$_2$)$_7$—CH=CH—CH$_2$—CH(OH)—CH(R$_{25}$)—(CH$_2$)$_4$—CH$_3$, and R$_{25}$ is —NH—CO—CH$_2$—COOH, a headgroup with no selectively cleavable group.

In still another embodiment, a symmetric amphiphilic compound has the formula Ig:

$$R_{27}\text{—CO—NH—}(CH_2)_2\text{—NH—CO—}R_{26} \qquad (Ig)$$

wherein

R$_{26}$ is —(CH$_2$)$_{12}$—CH(OH)—CH$_2$—R$_{23}$

R$_{27}$ is —(CH$_2$)$_{12}$—CH(OH)—CH$_2$—R$_{23}$, and

R$_{23}$ is —NHCH$_2$CH$_2$NH-phenyl-CH$_2$—CH(NH$_2$)COOH

The compound Ig is a compound of formula Ia wherein R$_1$ and R$_5$ are —(CH$_2$)$_{10}$, A$_1$ and A$_3$ are —CH$_2$—CH$_2$—CH(Y$_1$)—, Y$_1$ is —OH, R2 and R$_6$ are —CH$_2$, A$_2$ and A$_4$ are R$_{23}$, R$_3$ and R$_7$ are absent and R$_4$ and R$_8$ are H.

Compounds Ih-In below are some specific examples of amphiphilic compounds of the invention in which the hydrogen-bonding group is located within the headgroup containing the selectively cleavable group or moiety.

$$R_{28}\text{—CO—NH—}(CH_2)_2\text{—NH—CO—}R_{28} \qquad (Ih)$$

wherein

R$_{28}$ is —(CH$_2$)$_{12}$—R$_{23}$, and R$_{23}$ is —NHCH$_2$CH$_2$NH-phenyl-CH$_2$—CH(NH$_2$)COOH Compound Ih has the headgroup R$_{23}$ that contains both the selectively cleavable phenylalanine (levodopa-type) moiety and the hydrogen-bonding —NH— group attached to a (CH$_2$)$_{12}$ aliphatic chain, with no further hydrogen-bonding groups in the aliphatic chain.

$$R_{29}\text{—CO—NH—}(CH_2)_2\text{—NH—CO—}R_{29} \qquad (Ii)$$

wherein

R$_{29}$ is —(CH$_2$)$_{12}$—R$_{21}$, and R$_{21}$ is —NHCO—CH$_2$CH$_2$NH-phenyl-CH$_2$—CH(NH$_2$)COOH The sole difference between the compounds Ih and Ii is that the headgroup moiety R$_{23}$ in Ih is attached to the (CH$_2$)$_{12}$ aliphatic chain by an amino linkage while the headgroup moiety R$_{23}$ is attached by an amido linkage.

Compound Ij is an example of an asymmetrical amphiphilic compound with a bulky headgroup R$_{29}$ containing the levodopa-type headgroup on one end and a smaller headgroup with a —COOH group on the other end:

$$R_{30}\text{—CO—NH—}(CH_2)_2\text{—NH—CO—}R_{29} \qquad (Ij)$$

wherein

R$_{29}$ is —(CH$_2$)$_{12}$—R$_{21}$, and R$_{21}$ is —NHCO—CH$_2$CH$_2$NH-phenyl-CH$_2$—CH(NH$_2$)COOH, and R$_{30}$ is —(CH$_2$)$_{12}$—COOH.

Another example of a symmetrical amphiphilic compound is represented by formula Ik:

$$R_{31}\text{—CO—NH—}(CH_2)_2\text{—NH—CO—}R_{31} \qquad (Ik)$$

wherein

R$_{31}$ is —(CH$_2$)$_{12}$—R$_{32}$, and R$_{32}$ is —NHCH$_2$CH$_2$N$^+$(CH$_3$)$_2$—CH$_2$—CH$_2$—OCOCH$_3$ R$_{32}$ is an example of a headgroup containing both an acetylcholine-type group and the hydrogen-bonding —NH— group.

Another example of an asymmetrical amphiphilic compound is of the formula Il:

$$R_{33}\text{—CO—NH—}(CH_2)_2\text{—NH—CO—}R_{31} \qquad (Il)$$

wherein

R$_{31}$ is —(CH$_2$)$_{12}$—R$_{32}$, and R$_{32}$ is —NHCH$_2$CH$_2$N+(CH$_3$)$_2$—CH$_2$—CH$_2$—OCOCH$_3$, and R$_{33}$ is —(CH$_2$)$_{12}$—R$_{34}$, and R$_{34}$ is —NHCH$_2$CH$_2$N$^+$(CH$_3$)$_3$ In the asymmetrical double-headed amphiphilic derivative Il, one chain contains the bulkier ionic headgroup R$_{32}$ with the acetylcholine-type group and the hydrogen-bonding —NH— group, while the other aliphatic chain contains the smaller ionic headgroup.

Similarly to the amphiphilic compounds derived from vernolic acid and from saturated fatty acids exemplified above, further amphiphilic derivatives according to the invention are derived from the lesquerolic acid found in lesquerella oil, which acyl residue has the formula:

—CO—(CH$_2$)$_9$—CH=CH—CH$_2$—CH(OH)—(CH$_2$)$_5$CH$_3$

In one embodiment, a symmetric amphiphilic compound has the formula Im:

$$R_{35}\text{—CO—NH—}(CH_2)_2\text{—NH—CO—}R_{35} \qquad (Im)$$

wherein

R$_{35}$ is —(CH$_2$)$_9$—CH=CH—CH$_2$—CH(R$_{36}$)—(CH$_2$)$_5$CH$_3$ and R$_{36}$ is —OCH$_2$CH$_2$NH—CO—CH$_2$—CH$_2$—CH(NH$_2$)COOH $R_{36}$ is a headgroup containing the selectively cleavable residue of glutamic acid $OCH_2CH_2NH-CO-CH_2-CH_2-CH(NH_2)COOH$, and the hydrogen-bonding —CONH— polar group for stabilization.

In an additional embodiment, the amphiphilic derivatives of the invention are derived from the ricinoleic acid found in castor oil, which acyl residue has the formula:

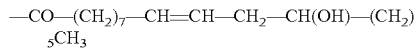

As an example, a symmetrical derivative has the formula In:

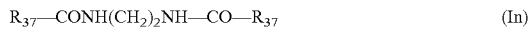 (In)

wherein $R_{37}$ is $-(CH_2)_7-CH=CH-CH_2-CH(R_{38})-(CH_2)_5CH_3$, and $R_{38}$ is $-OCH_2CH_2NH$-phenyl-$CH_2-CH(NH_2)COOH$ In a different embodiment of the invention, the amphiphilic compound has, besides the polar or ionic headgroups containing the selectively cleavable groups and the hydrogen-bonding groups, additional hydrophobic pendants either on the aliphatic chain and/or on the headgroup containing the selectively cleavable group or moiety.

In one embodiment, a symmetric amphiphilic compound having a hydrophobic pendant on the headgroup containing the selectively cleavable group has the formula Io:

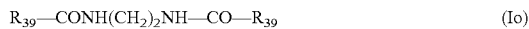 (Io)

wherein $R_{39}$ is $-(CH_2)_{12}-N(R_{40})CH_2CH_2NH$-phenyl-$CH_2-CH(NH_2)COOH$ and $R_{40}$ is a C4-C16 alkyl.

In the above compound, the headgroups that contain the selectively cleavable levodopa-type group and the H-bonding group —NH—, also have a relatively long aliphatic chain $R_{40}$ attached to an amino group in both headgroup moieties to give extra stability due to hydrophobic interactions.

In another embodiment, an additional hydrophobic group of the amphiphilic compound ($R_{40}$) is not located in the headgroup moiety as above, but is bound to the fatty acid chain through an ether linkage, as shown in formula Ip:

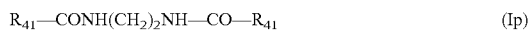 (Ip)

where $R_{41}$ is $-(CH_2)_7-CH=CH-CH_2-CH(OR_{40})-CH(R_{38})-(CH_2)_4CH_3$ $R_{40}$ is C4-C16 alkyl, and $R_{38}$ is $-OCH_2CH_2NH$-phenyl-$CH_2-CH(NH_2)COOH$ In a further embodiment, the amphiphilic compound of the invention is a bolaamphiphile of formula IIa comprising a $-CO-R_{10}-CO-$ midsection as follows:

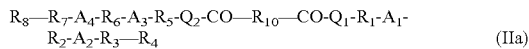 (IIa)

wherein all groups are as defined hereinabove and $Q_2$ and $Q_1$ are identical.

For example, starting from hexadecanoic acid [$HO_2C(CH_2)_{14}CO_2H$] and 11-hexadecen-1-ol [$CH_3(CH_2)_3CH=CH(CH_2)_{10}OH$], the following symmetric derivatives IIb and IIc with a headgroup containing a glutamic acid residue or a p-aminophenylalanine residue, respectively, can be synthesized:

where $R_{42}$ is $-(CH_2)_{10}-CH(OH)-CH(R_{43})-(CH_2)_3-CH_3$, and $R_{43}$ is $-O-CO-CH_2CH_2CH(NH_2)CO_2H$ (IIb)

or $R_{21}$: $-NH-CO-CH_2CH_2CH-NH$-phenylalanine (IIc)

An asymmetric bolaamphiphile can be made having one bulkier headgroup containing a p-aminophenylalanine residue and a second smaller headgroup containing a glutaric acid residue, as shown by formula IId:

 (IId)

where $R_{44}$ is $-(CH_2)_{10}-CH(OH)-CH(R_{46})-(CH_2)_3-CH_3$ $R_{45}$ is $-(CH_2)_{10}-CH(OH)-CH(R_{47})-(CH_2)_3-CH_3$ $R_{46}$ is $-NHCO-CH_2CH_2CH-NH$-phenyl alanine and $R_{47}$ is $-NHCO-CH_2CH_2CH_2CO_2H$ In another embodiment, a symmetric bolaamphiphile is provided in which there is no hydrogen-bonding —OH group on the vicinal carbon atom as in compounds IIb-IId above, but rather the hydrogen-bonding group is located within the headgroup containing an ionic selectively cleavable group, as shown in formula IIe:

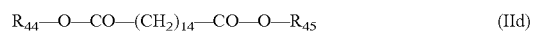 (IIe)

wherein $R_{48}$ is $-(CH_2)_{11}-NH-(CH_2)-N^+(CH_3)_2(CH_2)_2O-CO-CH_3Cl^-$

This symmetric bolaamphiphile has a headgroup $R_{48}$ containing both the acetylcholine-type moiety and the hydrogen-bonding —NH— group, and can be prepared starting from $HOOC-(CH_2)_{16}-COOH$ and 11-bromo-1-undecanol [$Br(CH_2)_{11}OH$].

In a further embodiment, starting again from $HOOC-(CH_2)_{16}-COOH$ and 11-bromo-1-undecanol, the following asymmetric bolaamphilie of formula IIf can be made with one acetylcholine headgroup and one glucosamine headgroup:

 (IIf)

wherein $R_{49}$ is $-(CH_2)_{11}-NH-(CH_2)-N^+(CH_3)_2(CH_2)_2O-CO-CH_3\ Cl^-$ and $R_{50}$ is $-(CH_2)_1,-NH-(CH_2)-NH-C_6H_{11}O_5$ where $-NH-C_6H_{11}O_5$ is the glucosamine moiety, useful for transport across the biological barriers.

In another different embodiment, the present invention provides amphiphilic derivatives capable of forming bilayered vesicles, in which two fatty acid chains are linked through a midsection/spacer region such as $-NH-(CH_2)_2-N^*-(CH_2)_2-N-$, the residue comprising the polar or ionic headgroup containing the selectively cleavable group or moiety is localized in the midsection of the molecule and is attached to the N* atom in the middle of the midsection region, between the two fatty acid chains. The midsection also contains hydrogen-bonding groups provided by the —CONH— groups at the intersection with the fatty acid chains, and the headgroup moiety may also contain hydrogen-bonding groups. An example of such a compound is the Derivative 4 herein.

According to this embodiment, the amphiphilic compound of the invention has the formula I'a:

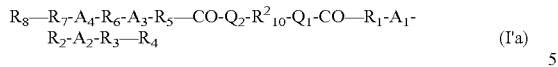
(I'a)

wherein $R_1$ to $R_8$, $A_1$, $A_2$, $A_3$, $A_4$, $Q_1$ and $Q_2$ are as defined above for compounds of formula Ia, with the proviso that functional groups or moieties that may function as headgroups are not present;

$R^2_{10}$ is a spacer including a residue comprising a headgroup containing a selectively cleavable group or moiety, said spacer being selected from: —$(CH_2)_q$—$R_{51}$—$(CH_2)_q$—; —$R_{52}$—C6-C14 arylene)-; or —C6-C14 arylene)-G2-($R_{52}$—C6-C14 arylene)-; wherein G2 is —$(CH_2)_q$—, —NH—, —S—, —SO—, —$SO_2$—, or —$CH(CH_3)_2$—, and q is an integer from 1 to 3;

$R_{51}$ is —N($R_{53}$)($R_{54}$)— wherein $R_{53}$ is a headgroup containing a selectively cleavable group or moiety, and $R_{54}$ is H or a C1-C18 alkyl group; and $R_{52}$ is a residue comprising a headgroup $R_{51}$ containing a selectively cleavable group or moiety.

The values and structures of $R_8$—$R_7$-$A_4$-$R_6$-$A_3$-$R_5$— may or may not be equivalent to $R_1$-$A_1$-$R_2$-$A_2$-$R_3$—$R_4$. In one preferred embodiment, they are equivalent.

The derivatives above can form vesicles with bilayered membranes, either a single bilayer membrane or multilayers of bilayer membranes.

Specific examples of this type of compounds are shown below in the compounds of formulas Iq-Iu:

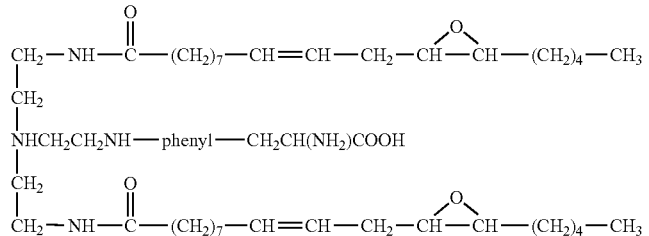
Iq

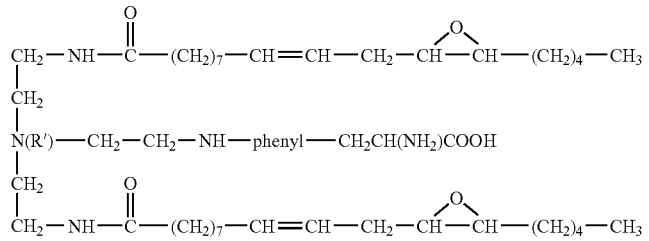
Ir where R' is C4–C18 alkyl.

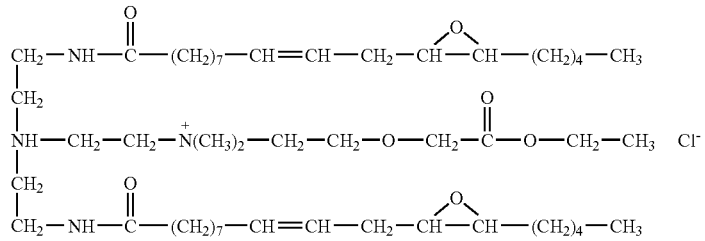
Is

Instead of amide linkage between the fatty acid and the midsection/spacer group, transesterification can be carried out to form similar derivatives but with ester bounds instead of amides, for example:

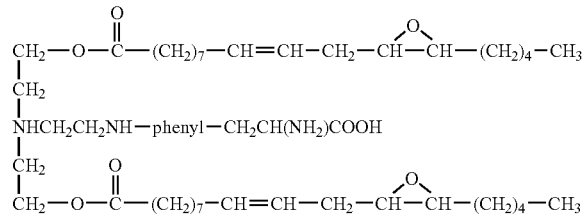

It

In addition, the fatty acid chains may contain polar groups for further stability such as the epoxy groups shown above or hydroxy groups shown below:

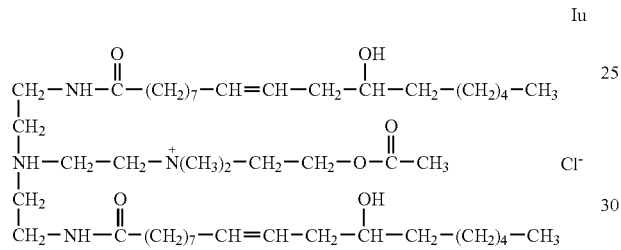

Iu

In still a further embodiment, the present invention provides amphiphilic compounds which are fatty acid glycerol derivatives with the headgroup containing the selectively cleavable group or moiety on one hydroxyl group of the glycerol and fatty acid chains on the remaining two hydroxyl groups, wherein said fatty acid chains contain additional polar groups or an epoxy group or halogens to contribute to stabilization of formed vesicles.

According to this embodiment, amphiphilic compounds are provided which are capable of forming bilayered vesicles, of the formula I″a:

$$R_8\text{—}R_7\text{-}A_4\text{-}R_6\text{-}A_3\text{-}R_5\text{—}C(=O)\text{-}Q_2\text{-}R^3{}_{10}\text{-}Q_1\text{-}C(=O)\text{—}R_1\text{-}A_1\text{-}R_2\text{-}A_2\text{-}R_3\text{—}R_4 \quad (I''a)$$

wherein $R_1$ to $R_8$, $A_1$, $A_2$, $A_3$ and $A_4$ are as defined above, with the proviso that functional groups or moieties that may function as headgroups are not present;

$Q_1$ and $Q_2$ are —O—;

$R^3{}_{10}$ is selected from —$CH_2$—$CH(OR_{55})$—$CH_2$— and —$CH(CH_2$—$OR_{55})$—$CH_2$—;

$R_{55}$ is selected from —$(CH_2)_{m'}R_{51}$ and —$CO(CH_2)_{m'}R_{51}$;

$R_{51}$ is a headgroup containing a selectively cleavable group or moiety: and m' is an integer from 0 to 4.

A compound according to this definition, wherein $R^3{}_{10}$ is —$CH_2$—$CH(OR_{55})$—$CH_2$— will have a structure as shown below:

H$_2$C—O—CO—R$_1$-A$_1$-R$_2$-A$_2$-R$_3$—R$_4$
|
HC—OR$_{55}$
|
H$_2$C—O—CO—R$_5$-A$_3$-R$_6$-A$_4$-R$_7$—R$_8$.

A compound according to this definition, wherein $R^3{}_{10}$ is —$CH(CH_2$—$OR_{55})$—$CH_2$— will have a structure as shown below:

H$_2$C—OR$_{55}$
|
HC—O—CO—R$_1$-A$_1$-R$_2$-A$_2$-R$_3$—R$_4$
|
H$_2$C—O—CO—R$_5$-A$_3$-R$_6$-A$_4$-R$_7$—R$_8$

The Rs and As groups on either fatty acid chain are all chosen from the same groups although within the groups the choice for each chain may be different. In one preferred case they are equivalent.

In yet still a further embodiment, the amphiphilic compounds of the present invention form bilayered membranes and have a sole aliphatic chain as defined before and either one short alkyl chain or a phenyl or phenylalkyl radical instead of the second aliphatic chain.

These derivatives have the general formula Iw:

$$R0\text{-}Q_1\text{-}CO\text{—}R_1\text{-}A_1\text{-}R_2\text{-}A_2\text{-}R_3\text{—}R_4 \quad (Iw)$$

wherein $R0$ is —$(CH_2)_{r'}$—$X7$;

$X7$ is hydrogen, C6-C14 aryl, preferably phenyl, or a heterocyclic radical;

r' is an integer from 0 to 12, preferably 1;

$Q_1$ is —O—, —S— or —NH—; and $R_1$, $A_1$, $R_2$, $A_2$, $R_3$, and $R_4$ are as defined before but should contain a headgroup containing a cleavable group or moiety and hydrogen-bonding groups, and a C8-C20 alkyl chain connected either to the fatty acid chain one or two carbons removed from the headgroup moiety or to a site in the headgroup moiety, thus forming an amphiphilic derivative with two alkyl chains originating from the area of the headgroup moiety.

An example of such compound of formula Iz is given below:

H$_3$CO—CO—(CH$_2$)$_7$—CH=CH—CH(OH)—CHNH
[(CH$_2$)$_2$—NHphenyl-CH$_2$—CH(NH$_2$)COOH]—
C$_5$H$_{11}$      Iz For the preparation of the amphiphilic derivatives of the present invention, methods similar to those described in WO 02/055011 of the same applicants can be used.

The preferred starting materials for making the above fatty acid chains are natural plant oils, in particular vernonia oil, castor oil and *lesquerella* oil, as well as of other fatty acids or their derivatives which contain in the fatty acid chain a combination of hydroxyl and/or epoxy groups and/or double bonds (e.g. allyl methyl groups, in effect methylene groups alpha to an olefin]. Through these reactive groups well-known methods in the art of chemistry can be carried out to get the different configurations of 1-2, 1-2-3, 1-2-3-4 or 1-2-3-4-5, 1-2-4, 1-2-5, 1-3-4, 1-3, 1-5, 1-4, 1-2-6, or 1-2-4-5 of the polar, ionic and/or epoxy groups substitutions of the fatty acid chains as defined above.

The chemistry transformations below are given as one type of preferred example, but they are not to be considered limiting. It is also to be considered that, although in the formulas herein the —OH group is presented in cis position to its vicinal group, this is done for reasons of convenience only and it is meant to include also the trans configuration that, in effect, is the preferred configuration of the compounds.

For illustration, the acyl chains of the fatty acids derived from vernonia, lesquerella and castor oil are given below, wherein the individual numbered reactive carbons may be modified according to the invention to produce the desired amphiphilic derivatives:

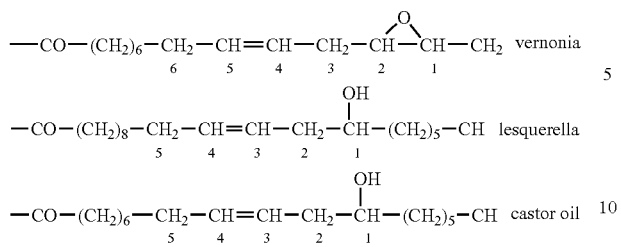

Any of the above carbons number 1 to 6 may be substituted in different combinations with polar or ionic groups as desired. For example, the epoxy group of vernonia may be substituted by different groups to give a 1-2 configuration. In one example as shown below, the epoxy group may be opened with a halocarboxylic acid such as chloroacetic acid to give a derivative wherein G1 is a haloacyloxy group (e.g. —OCOCH$_2$Cl) and G2 is —H, or the epoxy group may be opened with an azide (e.g. NaN$_3$) and then reduced to —NH$_2$ to give a derivative wherein G1 is —NH$_2$ and G2 is —OH, or the epoxy is opened by Na$_2$S then giving G1=—SH and G2=—OH. All these groups may be further derivatized at will by methods well-known in chemical synthesis. Thus, in the haloacyloxy OCOCH$_2$Cl group, the Cl may be further reacted with a tertiary amine, e.g. trimethyl amine, to give a quaternary ammonium group, or may be reacted with aminoethane sulfonic acid to give the corresponding aminoethane sulfonic acid derivative.

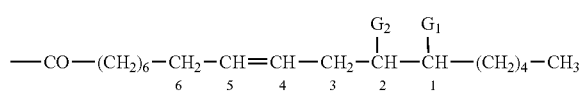

In another embodiment, the derivative above may be reacted with reagents which add across the double bond such as Br$_2$ thus forming derivatives with substitutions in positions 1-2-4-5 as shown below:

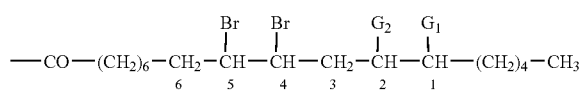

If reaction across the double bond is carried out with HBr, then derivatives with substitutions in positions 1-2-4 and 1-2-5 are formed as shown below:

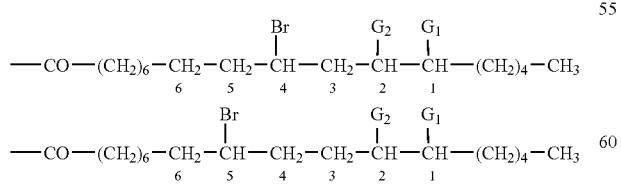

The —Br atoms may be readily reacted with compounds containing amino or sulfide groups to products containg anionic, cationic or zwitterionic groups. If the above bromo groups are replaced by —NH$_2$ or —SH groups or by moieties containing —NH$_2$ or —SH then derivatives are formed which may also be used to bind proteins, peptides, polysaccharides, DNA and RNA fragments In another embodiment, if vernonia oil below:

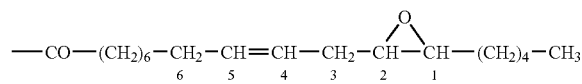

is subjected to N-bromosuccinamide/benzoyl peroxide+UV radiation, the 3 carbon is substituted with Br yielding the derivative:

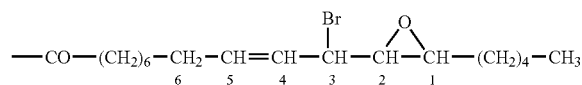

This bromo derivative may be further reacted with an amine to give:

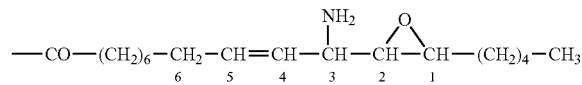

Then, upon opening the epoxy with Na+—OCOCH$_2$Cl, for example, the following derivative with a 1-2-3 combination is obtained:

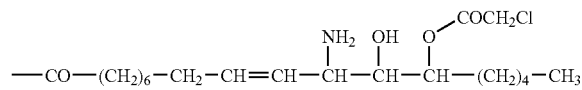

In another embodiment, the epoxy may be hydrolyzed to give:

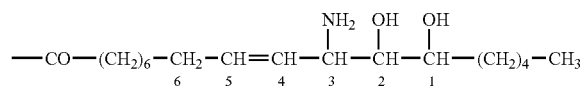

The amino group may be further reacted with well known reagents and conditions to give derivatives with anionic, cationic or zwitterionic moieties.

In another embodiment, if vernonia oil is reacted with N-bromo-succinamide/benzoyl peroxide/UV radiation in methylene chloride under conditions where the allyl H on the carbon atom 6 is substituted, then the derivative is formed:

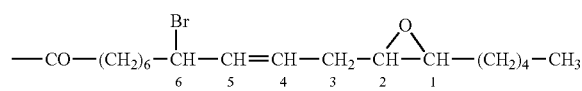

This derivative may be further reacted, for example with Na₂S, to give a 1-2-6 derivative below:

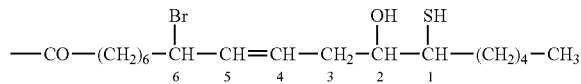

In another embodiment, if the acyl chain derived from lesquerella or castor oil is reacted with meta-chloroperoxybenzoic acid for epoxidation of the double bond, then the resulting derivatives are, respectively:

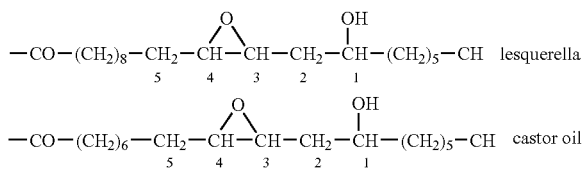

The epoxy may then undergo any of the reactions described in the specification. For example, the epoxy group may be opened and further reacted to give derivatives with substitutions in the 1-3-4 configuration as shown below, wherein G3 may be haloacyloxy (e.g. —OCOCH₂Cl) and G4 may be —OH, or the epoxy may be opened with an azide and then reduced to —NH₂ to give G3═—NH₂ and G4═—OH, or the epoxy is opened by Na₂S and G3═—SH and G4═—OH. The amino and the —SH as well as the —OH are readily derivatized to anionic, cationic or zwitterionic derivatives or they may be used to bind proteins, peptides, polysaccharides, DNA and RNA fragments.

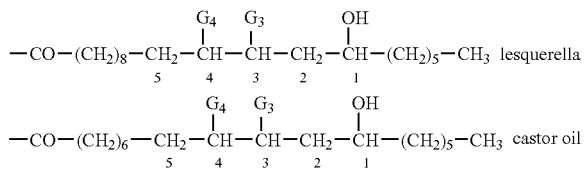

In another embodiment, other 1-3-4 derivatives may be synthesized if the acyl chain derived from lesquerella or castor oil are reacted with hypochlorous acid (HOCl) in water and then extracted into methylene chloride, and the following compounds may be obtained:

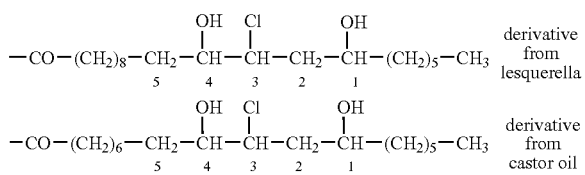

If the acyl chain of lesquerella or castor oil is reacted with N-bromosuccinamide/benzoyl peroxide/UV radiation in methylene chloride under conditions where the allyl Hs on both 2 and 5 carbons are substituted with Br, then the following 1-2-5 derivatives from lesquerella and castor oil are formed:

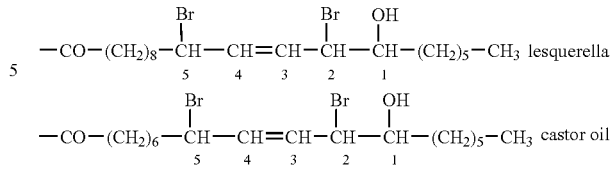

The —Br groups may be readily reacted as described above to give anionic, cationic and zwitterionic groups as described above. The above 1-2-5 derivatives may be further derivatized through the double bonds, with Br₂, for example, to give 1-2-3-4-5 substituted chains.

Both lesquerella or castor acyl chains may be reacted with N-bromosuccinamide/benzoyl peroxide/UV radiation in methylene chloride under conditions where only the allyl H on the second carbon atom has reacted, to give:

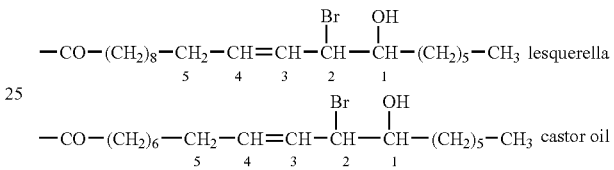

The —Br can be further reacted and derivatized as described above.

The above derivatives may be further reacted through the double bond with, for example, Br₂, to give 1-2-3-4 derivatives or with HBr to give 1-2-4 or 1-2-3 derivatives.

If both lesquerella or castor acyl chains are reacted with HBr or similar reagents which add across the double bond with a H radical adding to one carbon, then the 1-3 and 1-4 derivatives can be made. The HBr can also substitute the OH group with a bromide ion. The G group below can represent either OH or Br. The Br can be further substituted by an amino or mercapto group, which in turn can be modified to form anionic, cationic or zwitterionic groups.

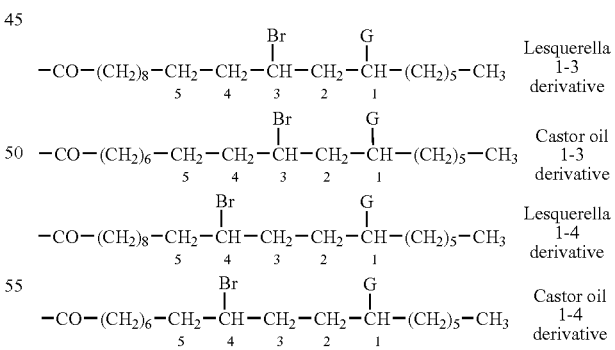

As described above, these derivatives may undergo further modification to substitute the Br with other groups or moieties to give polar or ionic groups or moieties as described above.

If both lesquerella or castor acyl chains are reacted with N-bromosuccinamide/benzoyl peroxide/UV radiation in methylene chloride under conditions where the allyl H on the 5 carbon is substituted with Br, these derivatives can be further derivatized as discussed above to give derivatives with polar and ionic groups in the 1-5 positions.

As used herein the term "C1-C18 alkyl" typically refers to a straight or branched alkyl radical having 1-18 carbon atoms and includes, for example, methyl, ethyl, n-propyl, isopropyl, n-butyl, iso-butyl, tert-butyl, n-heptyl, 2,2-dimethylpropyl, n-hexyl, n-dodecyl, n-octadecyl and the like. The term "C2-C16 alkylene" refers to straight or branched alkylene groups having 2-16 carbon atoms and includes for example methylene, ethylene, propylene, butylene and the like. The term "C2-C6 alkenyl" refers to straight or branched hydrocarbon radicals having 2-6 carbon atoms and at least one terminal double bond and includes for example vinyl, prop-2-en-1-yl, but-3-en-1-yl, pent-4-en-1-yl, and hex-5-en-1-yl. The term "aliphatic chain of up to 16 atoms optionally interrupted by $Q_2$ or —CO-$Q_2$" means that the chain including the heteroatoms represented by $Q_2$ has up to 16 atoms.

The term "C6-C14 aryl" refers to an aromatic carbocyclic group having 6 to 14 carbon atoms consisting of a single ring or multiple condensed rings such as phenyl, naphthyl, and phenanthryl optionally substituted by C1-C6 alkyl. The term "heterocyclic" refers to a monocyclic, bicyclic or tricyclic fused-ring heteroaromatic group. Particular examples are pyridyl, pyrrolyl, furyl, thienyl, imidazolyl, oxazolyl, quinolinyl, thiazolyl, pyrazolyl, 1,3,4-triazinyl, 1,2,3-triazinyl, benzofuryl, isobenzofuryl, indolyl, imidazo[1,2-a]pyridyl, benzimidazolyl, benzthiazolyl and benzoxazolyl. The term "halogen" refers to fluoro, chloro, bromo or iodo.

The invention further encompasses the salts of the amphiphilic derivatives. Examples of salts include, but are not limited to acid addition salts formed with inorganic acids (hydrochloric acid, hydrobromic acid, sulfuric acid, phosphoric acid, nitric acid and the like) and salts formed with organic acids such as acetic acid, oxalic acid, tartaric acid, succinic acid, maleic acid, fumaric acid, maleic acid, ascorbic acid, benzoic acid, and the like. Said compounds can also be quaternary salts known by a person skilled in the art, which specifically include the quaternary salt of the formula —NRR'R"+Z' wherein R, R', R" is independently hydrogen, alkyl or benzyl and Z is a counterion, including chloride, bromide, iodide, O-alkyl, toluenesulfonate, methylsulfonate, sulfonate, phosphate, or carboxylate.

Base addition salts are formed with metals or amines such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, ethylenediamine, and N-methylglucamine.

Vernonia oil derivatives of the invention are prepared from trivernolin, vernolic acid triglyceride, the main component of vernonia oil. Derivatization of trivernolin may be achieved by reacting pure trivernolin extracted from the vernonia oil mixture or by reacting the multi-component vernonia oil mixture followed by isolation of the products and purification of the functionalized trivernolin. In the Examples given in the present invention, preparation of the amphiphilic derivatives of trivernolin is carried on the vernonia oil mixture without initial separation of trivernoline, or unless specified otherwise. Trivernolin was separated from vernonia oil by column chromatography using n-hexane and increasing amounts of diethyl ether as the eluent as previously described (Grinberg et al., 1994). The TLC in n-hexane and diethyl ether (1.5:1 v/v) gave an $R_f$ of 0.4 for trivernolin. The amount of epoxy groups calculated for trivernolin was 13.6% (found: 13.3%).

In another aspect, the present invention provides vesicles/liposomes made from the novel amphiphilic derivatives of the invention for delivering biologically active agent, including pharmaceutical and diagnostic agents, specifically to a target organ while being insulated from non-relevant tissues.

The vesicles/liposomes of the invention have one or more of the following characteristics:

(i) an ionic or polar headgroup attached to a hydrophobic chain, said headgroup containing a selectively cleavable group or moiety and a hydrogen-bonding group within the headgroup or in close proximity thereto;

(ii) two ionic or polar headgroups on opposite ends of the hydrophobic chain moiety, at least one containing a selectively cleavable group or moiety and a hydrogen-bonding group within the headgroup or in close proximity thereto, and optionally containing additional ionic and polar groups in proximity to the said headgroups, that do not hinder vesicle formation but which are capable of polar or hydrogen-bonding interactions that stabilize the vesicles which are made from such derivatives;

(iii) two headgroups on opposite ends of the molecule, at least one containing a selectively cleavable group or moiety and a hydrogen-bonding group within the headgroup or in close proximity thereto, and said headgroups may optionally contain additional polar groups within the center or in relative proximity to the midsection or center of the hydrophobic chain, capable of polar or hydrogen-bonding interactions that stabilize the vesicles which are made from such derivatives;

(iv) in addition to (i) to (iii), additional aliphatic chain(s) of at least 5 methylene groups attached to the aforementioned hydrophobic chain moiety or to the headgroups to increase the hydrophobic interactions, and thus, contribute to the stability of vesicles which are made from such derivatives.

In one preferred embodiment, the vesicles comprise monolayered membranes made from the above-mentioned amphiphilic derivatives having two polar headgroups on both ends, wherein the selectively cleavable ionic or polar headgroup is oriented at least to the outer surface. One preferred vesicles comprising monolayered membranes are formed from, asymmetric amphiphiles derived from vernolic, lesquerolic or ricinoleic acid as described above, and have several advantages over the state-of-the-art bilayered vesicles: they are generally more stable, have thinner membranes, and totally asymmetric vesicle membranes can be formed with monolayered membranes but not with bilayers. This asymmetry allows the formation of smaller vesicles with improved stability, as these vesicles may contain smaller headgroups located in the interior with reduced steric repulsion by the headgroups, and thus, the inner surface has a smaller radius.

The physico-chemical interactions of the functional groups of the amphiphilic derivative allows the formation of physically, chemically and biologically stable vesicles, which nevertheless can release their contents selectively in the targeted tissue, cells, organs or microorganisms.

According to the invention, the active agent for diagnosis or therapy is encapsulated within the vesicles of the invention by known methods.

Disruption of the vesicle's membrane and release of its contents is initiated when the aforementioned polar or ionic selectively cleavable groups are cleaved by enzymatic activity or other conditions that affect the vesicle stability and may be confined mainly to the target organ. These conditions may be chemical environment such as pH or oxidants, or temperature, or chemical or enzymatic conditions that favor the hydrolysis of the headgroups, and thus disrupt the vesicles.

The rate of release from the disrupted vesicle is a function of the kinetics of the removal of the headgroups.

By using the functional amphiphilic derivatives of the invention having headgroups that can be selectively and controlably cleaved/removed, and a unique combination of stabilizing hydrophobic, polar and ionic groups, novel vesicles/liposomes are obtained that are nanosized, stable and targeting. This combination of properties overcomes the limitations of the state-of-art liposomes and enables the said vesicles to cross biological barriers and move freely in and out of different biological compartments, and yet, release their content mainly at the target organ where the enzymatic or chemical environment that destabilize the vesicles is localized.

The unique physical and chemical features of the amphiphilic derivatives of the present invention enable the manufacture of vesicles/liposomes that are sufficiently small to penetrate various biological barriers and yet remain intact until they release their content at a targeted site. These targeting vesicles contain the necessary stabilizing elements as well as surface functional groups needed for efficient targeting mechanisms.

Prior to the present invention, no vesicles that demonstrate the combination of nanosize, chemical, mechanical and biological stability, penetrability through biological barriers and selective release at the target organ, have been disclosed. These limitations of the state of art are especially evident when targeted controlled release platforms for the treatment of disorders of the CNS are considered. The present invention describes how these limitations of the state of the art can be overcome.

The amphiphilic derivatives of this invention have selectively cleavable ionic or polar headgroups attached to a hydrophobic aliphatic acid chain and additional functional groups attached at different sites on the said aliphatic chain. The latter groups give the vesicle additional stability, but nevertheless allow the vesicle to disrupt after the removal of the cleavable group that takes place in the target tissue. Furthermore, without these additional interactive groups, stable nanosized vesicles could not be formed, nor could the vesicles undergo, during production, post-formation surface modification without a significant reduction in the yield due to disruption. Post-formation surface modification is often needed to introduce functional groups that improve penetration through biological barriers or that minimize clearance by various biological mechanisms.

Another distinguishing feature of the present invention is the design of the headgroups containing the selectively cleavable group or moiety, so that their hydrolysis can be controlled according to conditions that are restricted to the target tissue. Such conditions may be enzymatic activity, chemical environment such as pH or oxidants and temperature. Specific hydrolysis of the headgroups at the target tissue will cause the disruption of the vesicle membrane at the hydrolysis site and thus, the release of the drug from within the vesicles will occur mainly at the target tissue.

International Application No. PCT/IL02/00043 of the present applicants, filed on 16 Jan. 2001 (published as WO 02/055011 on 18 Jul. 2002), herein incorporated by reference as if fully disclosed herein, describes certain amphiphilic derivatives, precursors thereof, and vesicles, liposomes, micelles, and complexants made from said amphiphilic derivatives. The amphiphilic derivatives and products made therefrom can be used in the fields of medicine, agriculture, food industry, cosmetics and chemical industry. The amphiphilic derivatives described therein disclose the polar and ionic functional groups and moieties needed to form stable nanosized vesicles. However, this patent application does not disclose headgroups which can be selectively cleaved to disrupt a stable vesicle at a target site. In our present invention, the amphiphilic derivatives are modifed by incorporating to them hydrolyzable cleavable or otherwise altered headgroups that determine where the vesicle will disrupt and release their content. An additional distinguishing feature of the present invention is that the said nanosized vesicles, prior to removing the exterior headgroup, can penetrate through biological barriers, and are relatively stable in different biological compartments.

The rate of release from the disrupted vesicles is a function of the rate of the hydrolysis and the removal of the ionic or the polar groups from the surface of the vesicular membrane or from within the aliphatic moiety. The destabilization of the vesicles may have different degrees. In one preferred degree, the vesicle's membrane is rapidly disintegrated and all the content is released rapidly following the hydrolysis. In another preferred embodiment, the disruption and release of the vesicular content takes place over a period of hours. The ability to control the rate of the release is another distinguishing feature of the invention.

Thus, in one highly preferred embodiment, the invention provides targeted controlled monolayered nanovesicles with asymmetric headgroups, made from double headed amphiphilic derivatives with two different polar or ionic headgroups on opposite sides of the aliphatic chains (bolaamphiphiles), wherein at least one of the said headgroups (the bulkier one) contains a group or moiety, located on the outer vesicle surface, that can be selectively cleaved/removed, and additional polar or ionic headgroups on the aliphatic chain(s) that are smaller and give the vesicle additional stability, but nevertheless allow the vesicle to disrupt after removal of the ionic or polar headgroups. Such vesicles can be sufficiently stable in order to serve as a general platform for drug delivery system with targeted controlled release features.

In one preferred embodiment, the vesicle preparations of the invention are designed for delivering therapeutic or diagnostic agents to the brain. Such vesicles contain headgroups that are hydrolyzed or rearranged by enzymes which are degradatives such as hydrolases, esterases, oxidases, decarboxylases, deaminases and isomerases. The degradative enzymes are either restricted to the brain, or alternatively, the delivery is applied in combination with enzyme inhibitors that do not penetrate the blood-brain-barrier, thereby preventing the disruption of the vesicles in the periphery where the degradative enzyme is inhibited. For example, the vesicle may contain a choline or, thiocholine derivative or an aromatic amino acid-type compound and the peripheral enzyme inhibitors may be a choline esterase inhibitor, an aromatic L-amino acid decarboxylase inhibitor, a monoamine oxidase (MAO) inhibitor and a catechol-o-methyltransferase (COMT) inhibitor.

One most preferred embodiment of the present invention consists in its applications in targeting controlled release platforms for targeting to the brain for the treatment of neurological/neurodegenerative diseases or disorders that affect the CNS such as Parkinson's disease or Alzheimer's disease or for treatment of brain tumors.

In one preferred embodiment, vesicles/liposomes of the invention containing the therapeutic drug for targeting to the brain are made of amphiphilic compounds having at their surface a headgroup containing an aromatic amino acid-type molecule such as phenylalanine, tyrosine, levodopa, tryptophan and derivatives thereof. The carboxyl group of these aromatic amino acids is selectively cleaved by aromatic L-amino acid decarboxylase (AADC) in the brain, thus releasing the therapeutic drug in the brain. However, AADC also exists in the periphery and can disrupt the vesicles before they reach the brain. Thus, in order to prevent premature disruption of the vesicles, the present invention also envisages the administration of the vesicles containing the therapeutic drug in combination with an AADC inhibitor such as benserazide or carbidopa, that will inhibit the peripheral AADC activity and prevent the disruption of the vesicles before they reach the brain. The inhibitor will be administered to the patient prior to the vesicles/liposomes containing the drug, usually from about 15 min up to about 1 hour or 2 hours before the encapsulated drug is administered.

In another embodiment, vesicles/liposomes of the invention containing the therapeutic drug for targeting to the brain are made of amphiphilic compounds having at their surface a headgroup containing one or more (thio)choline esters derivatives such as acetylcholine or acetylthiocholine, which are cleaved by acetylcholinesterase (ACHE) in the brain. However, ACHE present in the serum, liver and pancreas can also cleave the acetylcholine residue and similar derivatives. Thus, in order to prevent premature disruption of the vesicles, the present invention also envisages the administration of the vesicles containing the therapeutic drug in combination with an ACHE inhibitor that do not penetrate the blood-brain barrier (BBB) such as neostignine and pyridostigmine, that will inhibit the peripheral ACHE activity and prevent the disruption of the vesicles before they reach the brain. The inhibitor will be administered to the patient prior to the vesicles/liposomes containing the drug, usually from about 15 min up to about 1 hour or 2 hours before the encapsulated drug is administered.

For the purpose of administration of drugs within the brain, the vesicles of the invention may contain, besides the headgroups containing the selectively cleavable group or moiety, also ligands as functional groups on the surface of the vesicles for targeting purposes, and/or ligands as surface groups to increase permeability through the BBB.

Examples of ligands for targeting purposes include nicotine, cytisine (nicotinic agonist), lobeline (nicotinic agonist), 1-glutamic acid (a ligand of the NMDA and AMPA receptors, since it has specific transporter that transfers it across the BBB), MK801 (NMDA antagonist), morphine (binds to the opiate receptors), enkephaline (pentapeptides that bind opiate receptors, can also be used as a headgroup that is cleaved specifically by a brain-specific peptidase called enkephalinase), benzodiazepines such as diazepam (valium) and librium (bind to the GABA receptor complex), dopamine agonists (e.g. bromokriptine, pergolide, ropirinol etc.), dopamine antagonists (neuroleptics such as halidol, benzamine (sulpiride),phenothiazines), tricyclic antidepressants (such as amytyptiline and desimipramine), muscarinic agonists (such as oxotremorine, pilocarpine and cis-2-methylspiro[1,3-oxathiolane-5,3'-quinuclidine], muscarinic antagonists (have very high affinity to the muscarinic receptors, such as atropine and scopolamine), cannabinoids such as delta-9-tetrahydro canabbinol (delta-9-THC) and arachidonyl ethanol amide (see Umezawa and Eto, 1988; Wolf and Brett, 2000).

Examples of potential ligands for BBB transport, that help to transfer the liposomes through the BBB, include: monosaccharides such as glucose, mannose, and ascorbic acid; antibodies such as those targeting the transferrin receptors (were shown to be very effective in transferring liposomes via the BBB); choline; amino acids such as glutamic acid, tryptophan, and DOPA, that can be used as vectors for BBB transporters as well as cleavable headgroups that will cleave specifically in the brai (see Shi et al., 2001; Pardridge, 2001; Lee et al., 2001; Yang C. et al., 2001).

In one preferred embodiment, the vesicle preparations of the invention are designed for delivering agents for the treatment of diseases or disorders associated with the CNS. For the treatment of Parkinson's disease, the drugs to be encapsulated in the vesicles/liposomes of the invention include, but are not limited to, levodopa (L-DOPA), carbidopa/levodopa, apomorphine, dopamine, and growth factors such as glial derived neurotrophic factor (GDNF). For the treatment of Alzheimer's disease, the drugs include, but are not limited to, antibodies against components of the Alzheimer plaques, anti-inflammatory agents, growth factors, and muscarinic agonists that do not penetrate the BBB such as carbachol. For treatment of brain tumors, the vesicles may contain a suitable chemotherapeutic agent such as doxorubicin. The therapeutic agent is encapsulated by known methods in stable vesicles of the invention wherein the outer surface ionic groups of the vesicular membrane are composed of aromatic L-amino acids (e.g. phenylalanine, tyrosine, levodopa, tryptophan and their derivatives thereof) and the vesicles containing the therapeutic agent are administered to a patient in need thereof in combination with a peripheral aromatic L-amino acid decarboxylase inhibitor (e.g. benserazide or carbidopa). In another embodiment, the surface ionic groups of the vesicles membrane are composed of one or more choline esters and the peripheral activity of cholinesterases is inhibited by quaternary cholinesterase inhibitors that do not penetrate the blood-brain barrier, such as neostigmine and pyridostigmine.

In another preferred embodiment, the vesicle preparations of the invention are designed for delivering therapeutic agents which have a short lifetime at the delivery sites (e.g. stomach, intestine etc.) and have to be released at the site of action in another part of the body. For example, in one preferred embodiment, the invention provides vesicles that contain insulin for the treatment of diabetes, or Cop 1 (Copaxone) for the treatment of multiple sclerosis, or antibodies such as Herceptin for the treatment of breast cancer, or a mixture of immunoglobulins for the treatment of immunodeficiency diseases. All these agents exert their action in the blood circulation and have a short lifetime in the intestine and stomach and are poorly absorbed in the gastrointestinal (GI) tract. Said vesicles are designed to contain polar headgroups on the surface of the vesicular membrane which are composed of choline esters that are hydrolyzed by cholinesterases in the blood, thus releasing the therapeutic agent in the blood circulation. No enzyme inhibitors are needed in this case.

In another preferred embodiment, the invention provides vesicles designed to deliver an antibacterial or antiviral agent for the selective treatment of viral and bacterial infections, wherein the outer surface of the vesicle membrane contains functional groups that specifically interact with the viral wall such as, but not limited to, lectins and inactines, or with the bacterial wall such as, but not limited to, antibodies against the sequence LPXTG which constitutes the cell wall sorting signals in a variety of bacteria and also specific antibodies such as those against protein A of *Staphylococcus aureus*.

In a further embodiment, the invention provides liposomes for the delivery of nucleic acids/genes for gene therapy. For example, liposome formulations comprising liposome-DNA combinations/complexes are being developed for intratracheal gene therapy of lung cancer, for treatment of ovarian and other cancers, hemophilia, and other diseases.

The vesicle preparations of the present invention can be delivered by any suitable route including, but not being limited to, the following routes of administration: intravenous, oral, nasal, lung or gum administration.

The vesicles/liposomes of the invention may be made only from at least one amphiphilic derivative containing the selectively cleavable and hydrogen-bonding groups as defined hereinbefore, or they may be mixed with additional amphiphilic and or non-amphiphilic components that are distributed uniformly on the surface or in a mosaic configuration. If the disruption of the headgroups is such that it occurs only in mosaic patches of the vesicle membrane, then large holes in the membrane will be made through which its components are released.

For example, amphiphilic derivatives can be formed with headgroups containing moieties that assist in the transport across the biological barriers, e.g. across the BBB, as described hereinbefore, and/or containing moieties that assist in targeting, as described hereinbefore, and/or containing polyethylene glycol (PEG) moieties as a hydrophobic steric barrier to increase biological stability.

Examples of other materials which can be added as minor components of the vesicles of the invention are cholesterol, cholesterol derivatives and amphiphilic derivatives taken from zwitterionic, acidic, or cationic lipids. Examples of zwitterionic lipids are phosphatidylcholines, phosphatidylethanol amines, sphingomyelins. Examples of acidic amphiphilic lipids are phosphatidylglycerols, phosphatidylserines, phosphatidylinositols, and phosphatidic acids. Examples of cationic amphipathic lipids are diacyl trimethylammonium propanes, diacyl dimethylammonium propanes, and stearylamines. In addition, a cationic amphiphile such as spermine cholesterol carbamate (described in WO99/02190), that facilitates the transport of therapeutical biologically active molecules-into cells, can be added.

Covalent crosslinking is another mechanism to stabilize the vesicles chemically and mechanically. Covalent crosslinking of the amphiphilic membrane components of the vesicle in general prevents the disruption of the membrane after headgroup hydrolysis. This approach may nevertheless be used if the covalent bond can be selectively cleaved or if it is unevenly distributed throughout the vesicle membrane. Thus, selective covalent crosslinking of the membrane may be permissible in a mosaic distribution, where parts of the vesicle membrane which will disrupt are not crosslinked. The non-crosslinked portions may leach or disintegrate leaving a porous membrane through which said pores the content may be leached out.

Vesicles may be crosslinked either through the polar headgroups or through reactive groups within the hydrophobic membranes. For example, headgroups with vinyl substituents can be polymerized on the outer surface with water-soluble initiators or on both surfaces with UV radiation. Reactive groups within the hydrophobic layer of the membrane are inaccessible to water-soluble reagents. In general, visible and UV radiation has been used to polymerize amphiphiles through diene or diyne groups. Crosslinking may also occur via condensation reactions widely known in the state of art. For example, if the monomer amphiphilic compounds contain epoxy groups, they may be self-condensed using appropriate catalysts (e.g., tertiary amines containing hydroxyl or phenol groups), or through reaction with polyfunctional amines.

Functional groups and moieties may be used to stabilize the vesicles against clearance by the immune system and other clearing mechanisms of the body. Thus, other amphiphilic derivatives having oligomeric or polymeric chain moieties can be added during the vesicle formation stage as a minor component, and have a major effect on surface properties, without affecting vesicle stability (see Lasic, 1996). To improve transparency to the immune system and to improve biological stability, the following pendants can be added to the vesicle surface in varying amounts so as not to prevent enzymatic hydrolysis and disruption of the vesicle after hydrolysis of selectively cleavable groups: pendants from ganglioside GM1 or phosphatidylinositol at 5-10 mole % onto the surface, pendants from polymers such as, but not limited to, polyethylene glycols (PEG), polyethyloxazoline, polymethyloxazoline, PAA, and PVP covalently bound at about 5-mole % on the surface layer, and polysaccharides such as dextrans and cellulose.

For penetration through biological barriers, the small size of the vesicles is an important factor. The vesicles should be less than 1000 Å and in many cases closer to 200 Å. In some embodiments, sizes of 10 to 100 nm are preferred for many applications, and 15 to 30 nm for other applications. However, larger sizes can be used for other applications.

The invention will now be illustrated by the following non-limiting Examples.

EXAMPLES

The Derivatives 1, 2, 3, 4, 5, 8, 9, 12 of the invention, the Derivatives 6, 7, 10, 11 that have targeting, transporter or stabilization groups, and the Precursors 1-24 used herein for their preparation as well as a schematic presentation of the preparation methods are depicted in Schemes 1-31 herein. The preparation of the Precursors 1, 3, 4, 16, 23 is described in WO 02/055011.

Example 1

Synthesis of 13-(2-chloroacetoxy)-12-hydroxyoctadec-9-enoic acid methyl ester (Precursor 1)

Precursor 1 was prepared in one step from methyl vernolate as shown in Scheme 1 herein and as described in WO 02/055011 (Example 4).

Example 2

Synthesis of Precursor 2

Precursor 2 was prepared from Precursor 1 (X=Br) as shown in Scheme 2, as follows: To 0.449 g (1 mmol) of the Precursor 1 (X=Br) in 1 ml of dry acetone, 0.13 g (1 mmol) of 2-dimethylaminoethyl acetate was added and the solution was refluxed for 4 h. The quaternary salt (Rf=0.66) was separated from the reaction mixture by column chromatography using chloroform and methanol (1:1, v/v) as the eluent to give 0.26 g, 45% yield of Precursor 2.

$^1$H NMR spectrum, δ ppm: 0.8 (—CH$_3$), 2.1 (CH$_3$—C=O), 3.6 [N$^+$(CH$_3$)$_2$, C$\underline{H}$—OH and CH$_3$—O], 4.2 (N$^+$—CH$_2$—C$\underline{H}_2$), 4.5 (N$^+$—C$\underline{H}_2$—CH$_2$), 4.9 (C$\underline{H}$—O—C=O), 5.4 (CH=CH).

$^{13}$C NMR, δ ppm: 14.0 (CH$_3$), 20.8 ($\underline{C}$H$_3$—C=O), 51.4 and 52.6 (N$^+$(CH$_3$)$_2$ and CH$_3$—O), 58.4 and 62.7-63.2 (N$^+$—$\underline{C}$H$_2$—CH$_2$—O, N$^+$—$\underline{C}$H$_2$—CH$_2$—O, C=O—CH$_2$—N$^+$), 71.3 (CH—OH), 79.9 ($\underline{C}$H—O—C=O), 123.2-133.4 (CH=CH), 164.5, 170.0 and 174.3 (C=O).

Elemental analysis calculated for $C_{27}H_{50}NO_7Br$: $Br^-$, 13.74%. Found: 12.27% (content as determined by argentometric titration).

Example 3

Synthesis of N,N-ethylene bis (vernolamide)—Precursor 3

Precursor 3 was prepared either from trivernolin, or from methyl vernolate as shown in Scheme 3 herein, and as described in WO 02/055011 (Example 14).

Example 4

Synthesis of Precursor 4

Precursor 4 was prepared from Precursor 3 as shown in Scheme 4 herein and as described in WO 02/055011 (Example 15).

Example 5

Preparation of amphiphilic Derivative 1

Derivative 1 was prepared from Precursor 4 as shown in Scheme 5, as follows: To a solution of 0.81 g (0.001 mol) of Precursor 4 as the chloroacetate in dry acetone (2.0 ml), 0.264 g (0.002 mol) of dimethylaminoethyl acetate was added. The reaction mixture was refluxed for 3 h and then triturated with ether, thus obtaining Derivative 1 as the chloride salt. In a similar way, Precursor 4 as the bromoacetate was used for the preparation of Derivative 1 as the bromide salt.

$^1$H NMR, δ (ppm): 0.86 (—$CH_3$), 2.1 ($CH_3$—C=O), 3.3 ($CH_2$—NH), 3.58-3.63 [$N^+(CH_3)_2$, and C$\underline{H}$—OH], 4.2 ($N^+$—$CH_2$—$CH_2$), 4.5 ($N^+$—$CH_2$—$CH_2$), 4.9 (C$\underline{H}$—O—C=O), 5.2-5.5 (CH=CH) and (CO—$CH_2$—$N^+$).

$^{13}$C NMR, δ (ppm): 14.0 ($CH_3$), 20.8 ($\underline{C}H_3$—C=O), 52.2 and 52.6 ($N^+(CH_3)_2$), 57.5, 62.6 and 63.2 (CO—$\underline{C}H_2$—$N^+$) and ($N^+$—$\underline{C}H_2$—$CH_2$—O, $N^+$—$\underline{C}H_2$—$CH_2$—O), 71.7 (CH—OH), 80 (CH—O—C=O), 127-133 (CH=CH), 164.5 ($CH_3$—$\underline{C}O$), 169.8 (CH—O—$\underline{C}O$), 174.6 (NH—$\underline{C}O$).

Elemental analysis calculated for $C_{54}H_{100}N_4O_{12}Cl_2$ (MW=1067) Cl, 6.6%. Found: 6.5%. (content as determined by argentometric titration).

Elemental analysis calculated for $C_{54}H_{100}N_4O_{12}Br_2$ (MW=1156) Br, 13.8%. Found: 12.0%.

Example 6

Synthesis of Precursor 5

Precursor 5 was prepared from methyl ester of vernonia oil and glutaric acid as shown in Scheme 6, as follows: A mixture of 7.2 g methyl esters of vernonia oil and 17 g, of glutaric acid was refluxed in 230 ml of toluene for 48 h. After cooling in an ice bath, the excess of glutaric acid was precipitated and filtered (14.6 g). The toluene solution was washed with a 10% NaCl solution to a neutral pH, dried over magnesium sulfate and the solvent removed under reduced pressure to give 8.6 g of a crude product.

IR ($cm^{-1}$): 1710 (carboxylic group), 1734, 1739 (ester group)

$^1$NMR 500 MHz, toluene $d_6$ (δ, ppm): 0.89 (—$CH_3$), 2.46 ($CH_2$—CO—O), 3.4 ($CH_3$—O), 3.60 ($\underline{C}H_2$—OH), 5.45-5.54 (CH=CH), 4.9 (C$\underline{H}$—O—C=O).

$^{13}$C NMR, 500 MHz, toluene $d_6$ (δ, ppm): 50.97 ($\underline{C}H_3$—O—C=O), 72.2 and 72.6 ($\underline{C}H$—OH), 76.2 and 76.4 (CH—$\underline{C}H$—O—C=O), 124-132 (CH=CH), 177.9 ($\underline{C}OOH$), 173.7 ($CH_3$—O—$\underline{C}O$), 172.4 and 172.5 (CH—CH—O—$\underline{C}$=O)

HPLC RP C18 methanol:water 3:1, acetic acid pH=3.3 flow 1 ml/min Rt=16.7 min.

Elemental analysis $C_{24}H_{42}O_7$ (MW=442); acid no. 2.26 meq/g. Found 2.1.

MS m/z [M-H]=441.

Example 7

Synthesis of Precursor 6

Precursor 6 was prepared as the acyl halide of Precursor 5 as shown in Scheme 7, as follows: A solution containing 5 g of Precursor 5 and 7.5 ml of thionyl chloride in dry toluene (230 ml) was stirred overnight. The solution was then refluxed for two hours, cooled and the solvent was evaporated under reduced pressure to give a 5.3 g of the crude acyl halide.

IR ($cm^{-1}$) 1790 (acyl halide group).

$^1$NMR 200 MHz, $CDCl_3$, δ (ppm): 3.5 ($CH_3$—O), 5.4-5.7 (CH=CH), 4.0 ($CH_2$—Cl).

$^{13}$CNMR 200 MHz, $CDCl_3$, δ (ppm): 45.9 ($\underline{C}H_2$—Cl), 51.4 ($CH_3$—O), 171.7 ($\underline{C}OCl$), 173.3 ($CH_3$—O—$\underline{C}O$).

Elemental analysis: Calculated for $C_{24}H_{40}O_5Cl_2$ (MW=479): Cl, 14.8%. Found: Cl 13.7%.

Example 8

Synthesis of Precursor 7

Precursor 7 was prepared from Precursor 6 as shown in Scheme 8, as follows: A mixture of 2 g of the acyl chloride Precursor 6 and 0.7 g of dry choline chloride in 11 ml of dry acetone were refluxed for 4 h. The reaction mixture was cooled, ether was added and the excess of choline chloride was filtered. The solvent was removed under reduced pressure and washed several time with hexane.

Elemental analysis: Calculated for $C_{28}H_{52}NO_6Cl_2$ (MW=582): Cl, 6.1%. Found: 6.3%. Cl total found=11.4% ($Cl^-$ total calc.=12.2%).

MS m/z [M-Cl]=547.

Example 9

Synthesis of Precursor 8

Precursor 8 was prepared from Precursor 5 as shown in Scheme 9, as follows: A mixture of 200 mg of Precursor 5 (after purification by column chromatography), 93 mg DCC, 80 mg of dimethylaminoethanol in 50 ml of dry toluene, was refluxed for 20 h, cooled, filtered, washed with water, dried over magnesium sulfate and the solvent was evaporated. 140 mg of product was obtained. IR showed no acid peak, only esters peaks.

Elemental analysis Calculated for $C_{28}H_{53}NO_7$: MW=513.

MS m/z [M]=513.

Example 10

Synthesis of Precursor 9

Precursor 9 was prepared from Precursor 8 as shown in Scheme 10, as follows:

0.1 g of Precursor 8 was reacted with 0.25 g of methyl iodide in dry ether at RT for about 2 h and then left in refrigerator overnight. Amberlite CG-400-1 was used to obtain the chloride derivative.

Example 11

Synthesis of Precursor 10

Precursor 10 was prepared from Precursor 5 as described in Scheme 11, as follows: To a solution of 3 g of Precursor 5 in dry toluene, 0.95 g of choline chloride and 1.7 g of DCC were added and the reaction mixture was refluxed for 18 h.

Elemental analysis Calculated for $C_{29}H_{54}NO_7Cl$ (MW=563.5): $Cl^-$ 6.3%;

Found 5.9%. MS M/z [M-Cl]=528.

Example 12

Synthesis of Precursor 11

Precursor 11 was prepared from Precursor 3 as described in Scheme 12 as follows: A mixture of 1 g of diamide Precursor 3 (1.75 mmol) and 2.8 g of glutaric acid (21.2 mmol) in 70.5 g of 1,1,2-trichloroethane was stirred at reflux temperature for 17 h. Then the reaction was cooled. The excess of glutaric acid precipitated and was filtered. The filtrate was washed with a saturated solution of sodium chloride to pH=6.5, dried over magnesium sulfate and the solvent was removed under reduced pressure to give 1.56 g of crude product. The product was purified by column chromatography (80 g of silica gel) The eluent was a mixture of chloroform and methanol. 0.44 g of pure Precursor 11 was obtained.

IR $cm^{-1}$: 1732 (COOR), 1710 (COOH), 1641 (RCONH), 1555 (NH)

$^1$H NMR ppm: 7.0 (N$\underline{H}$ 2H), 5.4 (C$\underline{H}$=C$\underline{H}$ 4H), 4.8 (OC$\underline{H}$—CHOH 2H), 3.6 (C$\underline{H}$OH 2H), 3.4 (C$\underline{H}$2NH 4H)

$^{13}$C NMR ppm: 179 (CO of the carboxylic group) 175.5 & 172.8 (CO of the amide and ester group), 133-124.6 (CH=CH), 78 ($\underline{C}$HO—CHOH), 72.2-71.9 ($\underline{C}$HOH)

ESI-MS: m/z=880; 880-115 [—CO—(CH$_2$)$_3$—COOH]=765

Example 13

Synthesis of Precursor 12

Precursor 12 was prepared from Precursor 11 as shown in Scheme 13 as follows: A solution of 0.39 g of 1-[3-(dimethylamino)propyl]-3-ethyl-carbodiimide hydrochloride (EDCI) in 10 ml dichloromethane was added dropwise to a solution of 0.44 g of Precursor 11, 0.25 g DMAP (dimethylaminopyridine) and 0.48 g of dimethylaminoethanol in 10 ml dichloromethane. The temperature was kept at 0° C. during the addition The reaction was stirred at room temperature overnight. A saturated solution of NaCl was added and the phases were separated. The organic phase was washed with a diluted HCl solution, then with a solution of NaHCO$_3$, then again with the NaCl solution to pH=6.7. The organic phase was dried over magnesium sulfate and the solvent was removed under reduced pressure to give 0.23 g of crude product. The product was purified by column chromatography (133 g silica gel 60, the eluent:chloroform:methanol 10:1) 0.17 g of pure Precursor 12 was obtained.

IR $cm^{-1}$: 2773 (CH$_3$N); 1732 (COOR); 1652 (NHCO)

$^1$H NMR δ ppm: 0.8-0.83 (CH$_3$, 6H); 3.5-3.6 (C$\underline{H}$OH—CHOCO—, 2H); 4.0-0.2 (—OC$\underline{H}$2-CH$_2$—N—, 4H); 4.8 (C$\underline{H}$—O—CO, 2H); 5.4 (C$\underline{H}$=C$\underline{H}$, 4H); 6.5 (N$\underline{H}$, 2H)

$^3$C NMR δ ppm: 45.5 [($\underline{C}$H$_3$)$_2$N—]; 57.7 [O—$\underline{C}$H$_2$—$\underline{C}$H$_2$—N—]; 61.99 [$\underline{C}$H$_2$O]; 68 [$\underline{C}$H$_2$N(amide)]; 71.7 ($\underline{C}$H—OH); 167.6 [—$\underline{C}$O—O—CH2-CH2-N—]; 172.7-172.9

Example 14

Preparation of Derivative 2

Derivative 2 was prepared from Precursor 12 according to Scheme 14 as follows: A solution of 0.17 g of Precursor 11 and 2 ml of methyl iodide in acetone-isopropanol (1:1) as the solvents, was stirred at room temperature for 72 h. The solvent was removed under reduced pressure to give 0.18 g of the quaternary Derivative 2.

$I^{-1}$ found=15% $I^{-1}$ calcd.=19.4% (the $I^-$ was exchanged with $Cl^-$ using an Amberlite CG-400-I)

IR $cm^{-1}$: the peak at 2773 $cm^{-1}$ characteristic of the tertiary amine disappeared $^1$H NMR δ ppm: 0.83 (C$\underline{H}$$_3$—CH$_2$-6H); 3.0 (C$\underline{H}$$_3$N—, 18H), 3.6 (C$\underline{H}$OH—CHOCO); 4.4 (—OC$\underline{H}$$_2$—CH$_2$—N—, 4H); 4.7 (—CH—O—CO, 2H); 5.3-5.4 (CH=CH, 4H)

$^{13}$C NMR δ ppm: the chemical shift at 45.5 ppm characteristic of the tertiary amine [(CH$_3$)$_2$N)] disappeared and a new chemical shift at 52.9 ppm characteristic for the quat group [(CH$_3$)$_3$N)—] appeared; 57.9 (O—CH$_2$—CH$_2$—N); 63.8 ($\underline{C}$H$_2$O); 70.0 ($\underline{C}$H$_2$N, amide); 71 ($\underline{C}$HOH); 75 (—CH—O—CO—); 171.9-172.3 (—$\underline{C}$H$_2$—CO—O—)

ESI-MS: m/z [(M-2I)/2]=526 (z=2)

Example 15

Synthesis of Precursor 13

Precursor 13 was prepared as described in Scheme 15, as follows: A solution of 2 g 1,18-octadecanedicarboxylic acid, 2.94 g bromoundecanol and 0.4 g p-toluenesulfonic acid in 118 g toluene were refluxed with azeotrope overnight. After cooling, the mixture was washed with water, with a solution of 10% NaHCO$_3$, and with water again. The organic phase was dried over magnesium sulfate, and the solvent was removed under reduced pressure. Hexane was added and 4 g of the end product precipitated. Elemental analysis Calculated for Br, 19.8%. Found: 18%.

Example 16

Preparation of Derivative 3

Derivative 3 is an example of a compound that has a selectively cleavable group but no hydrogen bonding group. Nevertheless, it formed very stable vesicles and is herein encompassed by the present invention.

Derivative 3 was prepared from Precursor 13 as shown in Scheme 16, as follows: A solution of 1.5 g of the Precursor 13 and 1.9 g of 2-dimethylaminoethyl acetate in 25 ml nitromethane was refluxed for 6 h. Then the reaction mixture was cooled, the solvent evaporated, 30 ml of dichloromethane was added and the mixture was cooled in an ice bath. The

Example 17

Synthesis of Precursor 14

Precursor 14 was prepared from diethylene triamine and methyl vernolate or trivernolin as shown in Scheme 17 herein and as described in WO 02/055011.

Example 18

Synthesis of Precursor 15

Precursor 15 was prepared from Precursor 14 as described in Scheme 18, as follows: Precursor 14 (6.56 g, 10 mmol) was dissolved in 30 ml of dry toluene at 65° C. To this solution anhydrous potassium carbonate (0.69 g, 5 mmol) and dibromoethane (2.82 g, 15 mmol) were added and the reaction mixture was stirred at 60° C. for 15 hours. The reaction mixture, after filtration, was dissolved in chloroform and washed with water 3-4 times. The organic phase was separated, dried over $Na_2SO_4$ and evaporated under reduced pressure. The diamide mixture containing tertiary amine group was purified by column chromatography using acetone: methanol 1:1 v/v as the eluent to give the alkylated product Precursor 15.

IR (KBr, cm$^{-1}$): 3330, 1640, 1550(secondary amide), 2780 (tertiary amine), 840, 820 (epoxy group).

Elemental analysis $C_{42}H_{76}O_4N_3Br$ (MW=766) Calculated: Br, 10.44%. Found: 9.8%.

Example 19

Preparation of Derivative 4

Derivative 4 was synthesized from Precursor 15 s shown in Scheme 19, as follows: The alkylated product Precursor 15 was dissolved in 50 ml of dry acetone at 60° C. and N,N-dimethylaminoethyl acetate was added during 10 minutes. The reaction mixture was stirred and heated at 60° C. for 2 h. After cooling and removal of the solvent under reduced pressure, diethyl ether was added to the residue and the precipitate was then filtered to give a white powder of Derivative 4 (50% yield).

Elemental analysis Calculated for $C_{48}H_{89}O_6N_4Br$ (MW=897): Br, 8.9%. Found: 8.0%.

Example 20

Preparation of Derivative 5

Derivative 5 was prepared from Precursor 4 as described in Scheme 20, as follows: To a solution of (0.81 g) of Precursor 4 in 2 ml of dry acetone, p-aminophenylalanine (0.4 g) and potassium carbonate (0.145 g) were added. The reaction mixture was refluxed for 4 h. After filtration, the residue was triturated with ether to give Derivative 5

Example 21

Preparation of Derivative 6

Derivative 6 was prepared from Precursor 16 and Precursor 17 as shown in Schemes 21 and Scheme 22. Precursor 16 was prepared as described in WO 02/05501-1 (Example 24, the monomethylated form of Precursor 10 in Scheme 12 there). Precursor 17 was obtained from Precursor 16 by reaction with 3-chloropropyl-tetra-O-acetyl-β-D-glucopyranoside and sodium iodide in 2-methoxyethanol under reflux for 24 hours. The solvent was removed under reduced pressure and the residue purified on a silica gel column with methanol and chloroform as the eluent. The iodide ion (X=I$^-$ in Scheme 22) was exchanged with chloride by using a Dowex column, thus obtaining Derivative 6.

Example 22

Preparation of Derivative 7

Derivative 7 was prepared from Precursor 1 as shown in Scheme 23, as follows: To 0.449 g (1 mmol) of the Precursor 1 (X=Br)) in 2 ml of dry acetone, 0.165 g (1 mmol) of nicotine was added and the solution was refluxed for 3 h. The quaternary salt, was separated from the reaction mixture by column chromatography using chloroform and methanol (1:1, v/v) as the eluent.

Elemental analysis Calculated for $C_{31}H_{51}N_2O_5Br$: Br, 13%. Found: 11.9%.

Example 23

Synthesis of Precursor 18

Precursor 18 both as the chloroactoxy and bromoacetoxy derivatives was prepared from trivernolin as shown in Scheme 24, herein and as described in WO 02/055011 (Example 33).

Example 24

Preparation of Amphiphilic Derivative 8

Derivative 8 was prepared from Precursor 18 as shown in Scheme 25, as follows: The crude tris-chloroacetoxy Precursor 18 (1.73 g containing 1 mmol) and N,N-dimethylaminoethyl acetate (0.393 g, 3 mmol) were refluxed in 4 ml of acetone for 3 hours. The solvent was removed under reduced pressure and the residue was dried under vacuum at room temperature to give Derivative 8 as oil. The chloride ion amount of this product as determined by argentometric titration was equal to 3.49% (theoretical 4.03%). Yield of quaternization was equal to 86.6%.

Elemental Analysis: Calculated for $C_{105}H_{200}O_{15}N_3C_{13}$ (MW=1848.5): Cl, 5.76%; N, 2.27%. (70% of product): Cl=5.76×0.7=4.03%; N=2.27×0.7=1.59%. Found: Cl, 4.0%; N, 1.85%.

Derivative 8 is also obtained from the tris-bromoacetoxy precursor, under conditions identical to those described hereinabove.

Example 25

Preparation of Derivative 9

Derivative 9 was prepared as described in Schemes 26-28 by the catalytic reduction of the azido Precursor 19 to the corresponding amine (Precursor 20), followed by reaction

--- precipitated product was recrystalized 3 times from dichloromethane/ethyl acetate. 0.6 g of the Derivative 3 as a pure product was obtained.

Elemental analysis Calculated for Br, 14.9%. Found: 13.1%.

with 1,2-dibromoethane to obtain Precursor 21 and then nucleophilic substitution with p-amino-phenyl alanine, to obtain Derivative 9.

Example 26

Preparation of Amphiphilic Derivative 10

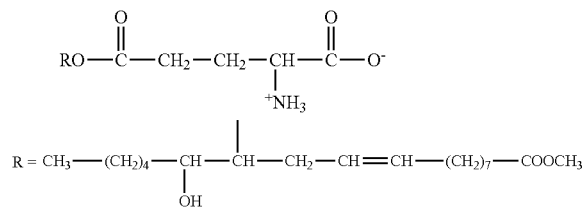

Derivative 10, the γ-ester of glutamic acid where R is a residue of vernolic acid, was prepared by reacting methyl vernolate with glutamic acid in the presence of thionyl chloride as previously described (see Widmer and Keller-Schierlein, 1974; Hanby et al., 1950).

Example 27

Preparation of Derivative 11 (PEG Derivative)

Derivative 11 was prepared as depicted in Scheme 29 by reacting Precursor 3 with PEG having different molecular weights (400, 600 and 2,000) in the presence of $(C_2H_5)_2O \cdot BF_3$.

Example 28

Preparation of Derivative 12

Derivative 12 was prepared as depicted in Schemes 30-31 as follows:

A mixture of 1 g (5.7 mmol) of 1,6-octanedioic acid and 11.5 g (57 mmol) of 1,12 diaminododecane in 50 ml of dibutyl ether was refluxed for 5 h. After cooling the reaction mixture to RT, the product was purified by column chromatography on Silica gel 60 to obtain 0.9 (yield: 29%) of the diamide Precursor 22.

IR $cm^{-1}$: 1650 $cm^{-1}$

A solution containing 1 g (1.86 mmol) of Precursor 22, 0.6 g of a-bromomethyl acetate and 0.31 g pyridine in 25 ml toluene was refluxed for 5 h. The precipitated pyridine hydrochloride was filtered after cooling the reaction. The solvent was removed under reduced pressure and the product was purified by column chromatography on Silica gel 60, thus obtaining 0.4 g of Precursor 23.

IR $cm^{-1}$: 1735, 1650

A solution of 1g (1.5 mmol) of Precursor 23, 1.3 g of N,N-dimethylaminoethanol and 0.1 ml of $NaOCH_3$ 2N (methanol) in 25 ml dichloromethane was refluxed for 8 h. After the completion of the reaction, the mixture was washed with water till pH=7, the crude product was purified by column chromatography to give 0.4 g of the pure Precursor 24.

IR $cm^{-1}$: 2773, 1735, 1650

A solution of 1 g (1.26 mmol) of Precursor 24 and 1 g of iodomethane in 25 ml acetone was refluxed for 5 h. The solvent was removed under reduced pressure to obtain Derivative 12 as the iodo salt ($X^- = I^-$). $I^-$ found 23%; $I^-$ calcd. 23.5%. The chloro derivative of Derivative 12 ($X^- = Cl^-$) was obtained by passing through an ion exchange resin (Amberlite 50).

Example 29

Methods for the Preparation of the Vesicles/Liposomes

According to the present invention, the liposomes and vesicles can be made by any of the many of the state of the art procedures such as, but not limited to: (i) hydration with shaking or mixing of dried phospholipids results in the spontaneous formation of multi-compartment liposomes; (ii) freeze drying the lipid dissolved in a suitable organic solvent and then adding the dried material to an aqueous solution; (iii) extrusion through polycarbonate membranes results in multi-compartment liposomes; (iv) sonication, either by probe or in bath; (v) injection of an alcoholic solution of the lipids through a small bore-Hamilton syringe into a well stirred aqueous solution at a temperature above the phase transition of the lipid; (vi) co-solubilizing a lipid with a detergent which is then removed by filtration or dialysis; (vii) injection of lipid dispersions through the small orifice of a power press (French Press), combined with reverse phase evaporation and a sequential extrusion through polycarbonate membranes; (viii) slow swelling of a lipid film in an aqueous solution; (ix) injection of a lipid-ether solution into a warm aqueous solution; (x) removal of the organic phase under reduced pressure from water-oil emulsion; (xi) injection of an immiscible organic solvent, which dissolves the lipid, into water followed by evaporation of the solvent; and (xii) dispersion of the amphiphiles, dissolved in organic solvent in water to form a water in oil emulsion. These vesicles are then suspended in aqueous medium and have an aqueous core, the two aqueous compartments separated from each other by the amphiphilic layer. Upon evaporation of the solvent results in vesicles with very high entrapment yields.

These procedures are described, for example, in the following references: Benita, 1996; Fendler, 1982; Toshinori and Sunamoto, 1992; Kunitake et al., 1981a; Kunitake et al., 1981b; Kunitake and Okahata, 1977; Boder et al., 1981; Fuhrhop and Mathieu, 1984, each and all of these references being herein incorporated by reference as if fully disclosed herein.

In general, it has been shown that emulsions of many different water insoluble compounds have an innate property of forming membrane vesicles when subjected to ultrasonic treatment or phase transfer conditions. A particular method can give a certain type of vesicle. Thus, for the same amphiphilic derivative, a range of different vesicle sizes can be made by choosing different methods or variations. For many applications requiring penetration through biological barriers the methods of preparation leading to vesicles of less than 100 nm diameter are preferred, and sizes in the range of about 20 nm and less are most preferred.

One preferred method for forming nanovesicles according to the present invention is by sonication. To improve encapsulation efficiency we have used a combination of the method (xii) above with sonication, which was applied after evaporation of the solvent. For obtaining larger vesicles, we used one of the above procedures as described in the specific examples. In another case, hydration with mixing of the dried amphiphilic derivative with one head group resulted in the spontaneous formation of a multi-compartment vesicle. The vesicles obtained by this method were heterogeneous, having a sphere onion-like, oblong, and tubular structures. They were however all closed and their aqueous compartments separated from each other. These multi-compartment heterodispersed vesicles were 1800 Å to 8000 Å in diameter.

In another case, multi-compartment vesicles of homogeneity and defined size were prepared by extrusion of monohead group amphiphilic derivative at 35° C. (above the phase transition) through 1 micron Nucleopore membranes. Monolayered vesicles were formed from bipolar amphiphilic derivatives by the introduction of an aqueous buffer into an ether solution of the amphiphile derivative, followed by the removal of the ether.

Large single compartment vesicles were also obtained without sonication by injection of an alcoholic solution of double head amphiphile through a small bore Hamilton syringe into a well stirred solution at room temperature (above the phase transition of the amphiphilic derivative), followed by removal of the ethanol by evaporation.

Large single compartment bilayer vesicles were made by slow swelling of an amphiphilic film to give 0.8-micron vesicles.

Example 30

Methods for Encapsulation of Active Materials

Biologically active compounds may be encapsulated in the process of forming the vesicle or can be loaded into the vesicle after its formation. The different methods of achieving encapsulation of drugs in vesicles are well known in the art and all can be used in principle with the amphiphilic derivatives of the present invention. Lipophilic molecules can be entrapped in the lipid layer. In this case it may be advantageous to make small multilayer vesicles to maximize the quantity of drug that may be encapsulated. In another embodiment of the invention, the amphiphilic derivatives that make the vesicle may be designed to maximize the adsorption and the number of adsorption sites to the drug.

For the encapsulation of hydrophilic drugs, single layer vesicles will give the highest encapsulation. High loading may be further achieved by loading the vesicle after formation using different pH gradient methods as a function of the pKa of the drug to be loaded.

Hydrophilic drugs can be loaded into the vesicles after they were formed. For drugs having ionizable amine groups, the loading is across an ammonium ion gradient. Ammonium ions within the vesicles are in equilibrium with ammonia, which is freely permeable, and protons accumulate as the ammonia is lost from the liposomes. This leads to a lower inside/higher outside pH gradient. After establishing the gradient, excess of ammonium ions within the liposomes provides a reservoir of protons to maintain the pH gradient over time. Thus, as amine drugs permeate across the membrane into the liposomes, they are converted into ammonium ions which keeps them entrapped.

A similar approach can be used for loading high drug concentration of an ionizable drug, which is negatively charged in its ionized state. In this case, liposomes are formed with weak acids (formic, acetic, propanoic acid, etc) having a higher inside/lower outside pH gradient. The gradient allows the loading of weak acid compounds as previously described in U.S. Pat. No. 5,939,096, herein incorporated by reference as if fully disclosed herein Example 31

Assessing the Susceptibility of the Headgroups of the Amphiphilic Derivatives to Undergo Specific Enzymatic Hydrolysis The novel amphiphilic derivatives were designed for the formation of vesicles, which will remain stable until conditions are met, mainly or exclusively in the target organ, that will promote the hydrolysis of the headgroups and thus will result in the destabilization of the vesicles and release of their content within the target organ. Three novel amphiphilic derivatives, synthesized from vernonia oil, were chosen to assess this concept.

31A. Hydrolyis of Cholinester Headgroups by Acetylcholinesterases

The ability of cholinesterases (ChE) to hydrolyze Derivatives 1 and 2 was assessed using two methods:

(i) The pH-stat method: Hydrolysis of the acetylcholine ester headgroups of Derivative 1, as well as of acetylcholine (ACh), by cholinesterases (ChE), releases acetic acid into the solution. Hydrolysis of Derivative 2 by ChE releases choline and a free fatty acid. In both cases, the release of acid results in pH drop. The hydrolysis rate of these compounds can be determined by measuring the amount of NaOH needed to neutralize the acid generated during hydrolysis. Three solutions, 100 mM concentration each of acetylcholine (ACh) in water and of Derivatives 1 and 2 in methanol were prepared, then diluted 100 times with water (10 ml), and their pH was adjusted to pH 9.0 using 0.1M NaOH. The pH was monitored until it remained stable for 10 min (baseline). At this stage, human serum (0.1 ml) containing ChE, was added and each of the solutions was titrated with 0.05M NaOH in order to maintain pH 9.0. The amount of the NaOH needed to maintain constant pH was measured during 15 min. The results, which are summarized in FIG. 1, show that each of the three compounds hydrolyzes at different rates, the fastest of which was observed for ACh and the slowest hydrolysis rate was observed for Derivative 2. Hydrolysis of all three compounds was completely blocked by the ChE inhibitor, pyridostigmine ($10^{-5}$M), indicating that the hydrolysis was cholinesterase-specific. These results suggest that the rate of hydrolysis can be determined by the nature of the head group. Thus vesicles prepared from Derivative 1 are expected to disrupt, in presence of ChE, faster than vesicles made from Derivative 2.

Figure 2:
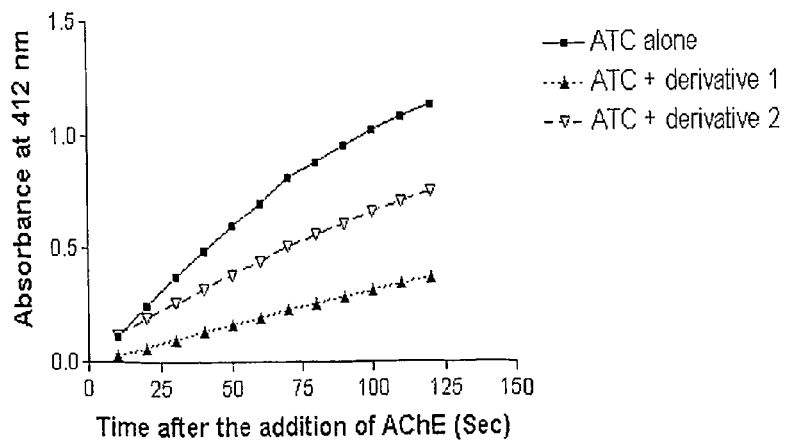
FIG. 2 shows the kinetics of development of yellow color following the interaction of dithionitrobenzoate (DTNB) with thiocholine released from acetylthiocholine (ATC) in presence and absence of Derivatives 1 and 2.

(ii) Competition assay using the Elman's method: Hydrolysis of acetylthiocholine (ATC) releases thiocholine, which reduces 5,5'-dithiobis-2-nitrobenzoate (DTNB) giving rise to a yellow coloring of the solution. Addition of a substrate, which is also hydrolyzed by ChE but does not release thiocholine, will inhibit the development of the yellow color, due to a competition between ATC and the other substrate for the hydrolyzing enzyme. A series of solutions with varying concentrations of Derivatives 1 and 2 in methanol together with acetylthiocholine (1.5 mM), DTNB (0.5 mM), and with 3 units of acetylcholinesterase (ACHE) in phosphate-buffered saline, was prepared. The rate of appearance of yellow color was determined in each of the reaction mixtures. The results, summarized in FIG. 2, show that Derivative 1 competes with acetylthiocholine to a higher extent than Derivative 2. These results are consistent with those obtained from the pH-stat experiment, indicating that the headgroup of Derivative 1 is preferably recognized by the cholinesterase enzymes, therefore undergoing a faster hydrolysis compared to the headgroup of Derivative 2. Thus, vesicles prepared from Derivative 1 are expected to disrupt faster than vesicles prepared from Derivative 2, when exposed to cholinesterases.

31B. Removal of Levodopa Headgroup by Decarboxylation with Aromatic Amino Acid Decarboxylase (AADC)

Derivative 5 contains an aromatic amino acid moiety as a headgroup. This negatively charged headgroup, at physiological pH, may be a suitable substrate for the enzyme aromatic L-amino acid decarboxylase (AADC). Upon exposure to AADC, the headgroup of Derivative 5 should be converted to an amine thus changing the nature of the headgroup (from a carboxyl to amine) in a way that can result in destabilization of vesicles made from Derivative 5.

To test whether Derivative 5 could serve as a substrate for AADC, rat liver homogenate served as the source for AADC and the following experiment was carried out. A methanol solution (0.005 ml) of Derivative 5 was added to a reaction mixture (0.5 ml final volume) containing potassium phosphate (50 mM, pH=7.0), dithiothreitol (1 mM), EDTA (0.2 mM), pyridoxal 5'-phosphate (0.01 mM), pargylin (0.1 mM), and rat liver homogenate adjusted to 5 mg protein. The final concentration of Derivative 5 was 1 mM. The reaction mixture was incubated at 37° C. for 60 min followed by the addition of 0.05 ml perchloric acid (70%) and neutralized by 4M KOH. The mixture was then centrifuged at 20.000 g for 10 min at 4° C. and 0.1 ml of the supernatant was injected into a C18-HPLC column. The presence of the amine, which was formed during the reaction, was determined by electrochemical detector. The mobile phase consisted of 75 mM sodium citrate (pH=3.1), 20 mM trichloroacetic acid, 1.5 mM sodium dodecil sulfate, $2\times10^{-6}$M EDTA, 14% acetonitrile and 7% methanol. A peak having the same retention time as the reference compound, which represents the amine formed from decarboxylation of Derivative 5, was eluted from the reaction mixture, indicating that Derivative 5 was decarboxylated. This peak was not detectable when benserazide, a known decarboxylase inhibitor, was added to the reaction mixture at a concentration of $5\times10^{-5}$ M. In addition, the appearance of the peak, which corresponds to the amine, was dependent on the presence of liver homogenate in the reaction mixture (results not shown). This experiment indicates that Derivative 5 was decarboxylated by AADC.

31 C. Control of the Vesicle Stability by Functional Headgroups

Vesicles loaded with acetylthiocholine (ATC), were prepared from the amphiphilic Derivatives 1 and 5, as well as from dipalmitoyl phosphatidyl choline (DPPC), as follows: Each of the amphiphilic Derivatives 1 and 5 (20 mg/ml) was added to a solution of ATC (0.1M) in phosphate buffer (50 mM, pH 7.0) and vesicles were prepared by sonication. Extravesicular ATC was removed by chromatography of the liposomes over Sephadex G-25M columns followed by dialysis against phosphate buffer. Sodium dithionitrobenzoate (DTNB) was added to the liposomal suspension at a final concentration of 0.5 mM. The liposomal suspension was rthen monitored spectrophotometrically at 412 nm until a steady reading was obtained.

Upon addition of 10 units of acetylcholinesterase (AChE from electric eel) to the vesicles, which were made from Derivative 1, an increase in the absorbance was observed due to the development of yellow color, which results from the interaction of ATC with DTNB. This reaction takes place only when ATC is released from the liposomes and comes in contact with DTNB. No change in absorbance was observed when the same procedure was applied to vesicles made from Derivative 5 or DPPC, or to vesicles made from Derivative 1 in the absence of AChE.

Figure 3:
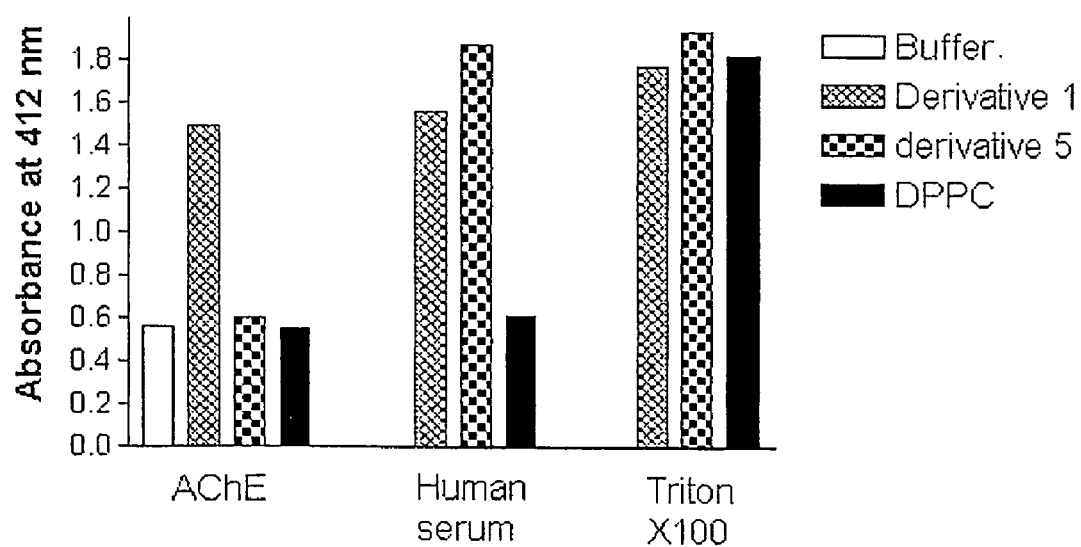
FIG. 3 shows the release of encapsulated ATC from vesicles that were exposed to disrupting conditions. Vesicles made from the amphiphilic Derivatives 1 and 5, or from dipalmitoyl phosphatidylcholine (DPPC) were loaded with ATC. Following the removal of extravesicular ATC, DTNB was added and the vesicles were exposed to the following conditions: (i) acetylcholinesterase (AChE); (ii) human serum; (iii) Triton X100. The development of the yellow color as the result of the interaction between ATC and DTNB was monitored spectrophotometrically at 412 nm.

However, addition of human serum (which contains both AADC and AChE) to vesicles made from Derivative 1 or Derivative 5 or DPPC resulted in the appearance of the yellow color only in vesicles made from Derivatives 1 and 5, but not in vesicles made from DPPC. Benserazide, at a concentration of $5\times10^{-5}$M, inhibited the development of the yellow color, which resulted from the addition of human serum, only in vesicles which were made from Derivative 5, whereas the development of the yellow color in vesicles made from Derivative 1, was unaffected by benserazide. Finally, in the presence of 1% Triton X100, the yellow color developed in all the three vesicle preparations described above. The results, depicted in FIG. 3, indicate that the yellow color develop only when the vesicle structure is disrupted and that vesicles made from Derivative 1 are stable in the absence of ACHE, but they break in the presence of ACHE, whereas vesicles made from Derivative 5 are stable in the presence of ACHE and in the absence of AADC, but they break in the presence of AADC (human serum). Finally, vesicles made from DPPC, which do not contain degradable headgroups, are not sensitive to either of these enzymes.

Example 32

Delivery of Insulin to the Blood Circulation via the Intestinal Wall

Vesicles made of Derivative 1 were loaded with insulin as follows: 20 mg of Derivative 1 were added to a solution containing 2 mg/ml insulin in phosphate-buffered saline and the mixture was sonicated for 20 min. This procedure yielded insulin-loaded vesicles having a diameter of 20-30 nm. The non-encapsulated insulin was removed by gel filtration on Sephadex G-150. Vesicles were eluted immediately after the void volume. This vesicle preparation was administrated, by means of catheterization, into the small intestine of alloxan-treated rats (an animal model for diabetes) (150 mg/kg, 2 weeks before the experiment), which were deprived of food 24 hours before administration of the vesicles (rats from local bred, weiglhing 300-400 g, kept under controlled conditions in the animal facilities of the Ben-Gurion University of the Negev, Israel). The insulin dose was fixed at 15 units per kg body weight and blood sugar was determined at various times following catheterization. Empty vesicles administrated into the small intestine, served as control. A significant reduction in blood glucose (from a mean of 255 mg to a mean of 130 mg glucose per 100 ml of blood) was observed only in animals that were treated with insulin-loaded vesicles, indicating that the vesicles penetrated the intestinal wall, disrupted in the blood circulation and released the entrapped insulin therein.

Example 33

Delivery of [$^{14}$C] Dextran-Loaded Liposomes Across the BBB

Vesicles made of Derivative 5 were loaded with [$^{14}$C]dextran as follows: 20 mg of Derivative 5 were added to a solution containing 1 µCi/ml [$^{14}$C]dextran in phosphate-buffered saline and the mixture was sonicated for 20 min. This procedure resulted in [$^{14}$C]dextran-loaded vesicles having a diameter of 20-30 nm. Rats were injected with 50 mg/kg benserazide (intramuscularly) and 30 min after the injection [$^{14}$C] dextran-loaded vesicles were injected into the carotid artery of these animals. Likewise, free [$^{14}$C]dextran having the same amount of radioactivity was injected to a second group of rats. At various times after the injection animals were deeply anesthetized, blood samples were taken from the animals and their brain was removed. The cerebral cortex was separated from the brain by free hand dissection and homogenized in water. The homogenates were centrifuged at 20.000 g for 10 min and radioactivity was determined in the supernatant. The ratio of radioactivity found in homogenate of the cerebral cortex to that of the blood was determined for each time point. As can be seen in Table 1, higher ratios were found in animals that were injected with vesicles, indicating that the vesicles penetrated the BBB, disrupted in the brain and released the labeled [$^{14}$C]dextran therein.

TABLE 1

Blood-brain barrier permeability of vesicles made of Derivative 5 and release of their content in the brain.

| Time (min) | Ratio of radioactivity in the cerebral cortex/radioactivity in the blood | |
|---|---|---|
| | Rats injected with [$^{14}$C] dextran-loaded vesicles | Rats injected with free [$^{14}$C] dextran |
| 15 | 0.34 | 0.22 |
| 30 | 1.15 | 0.26 |
| 60 | 0.67 | 0.24 |

Example 34

Preparation of Vesicles from Derivatives 1 and 5

Figure 4:
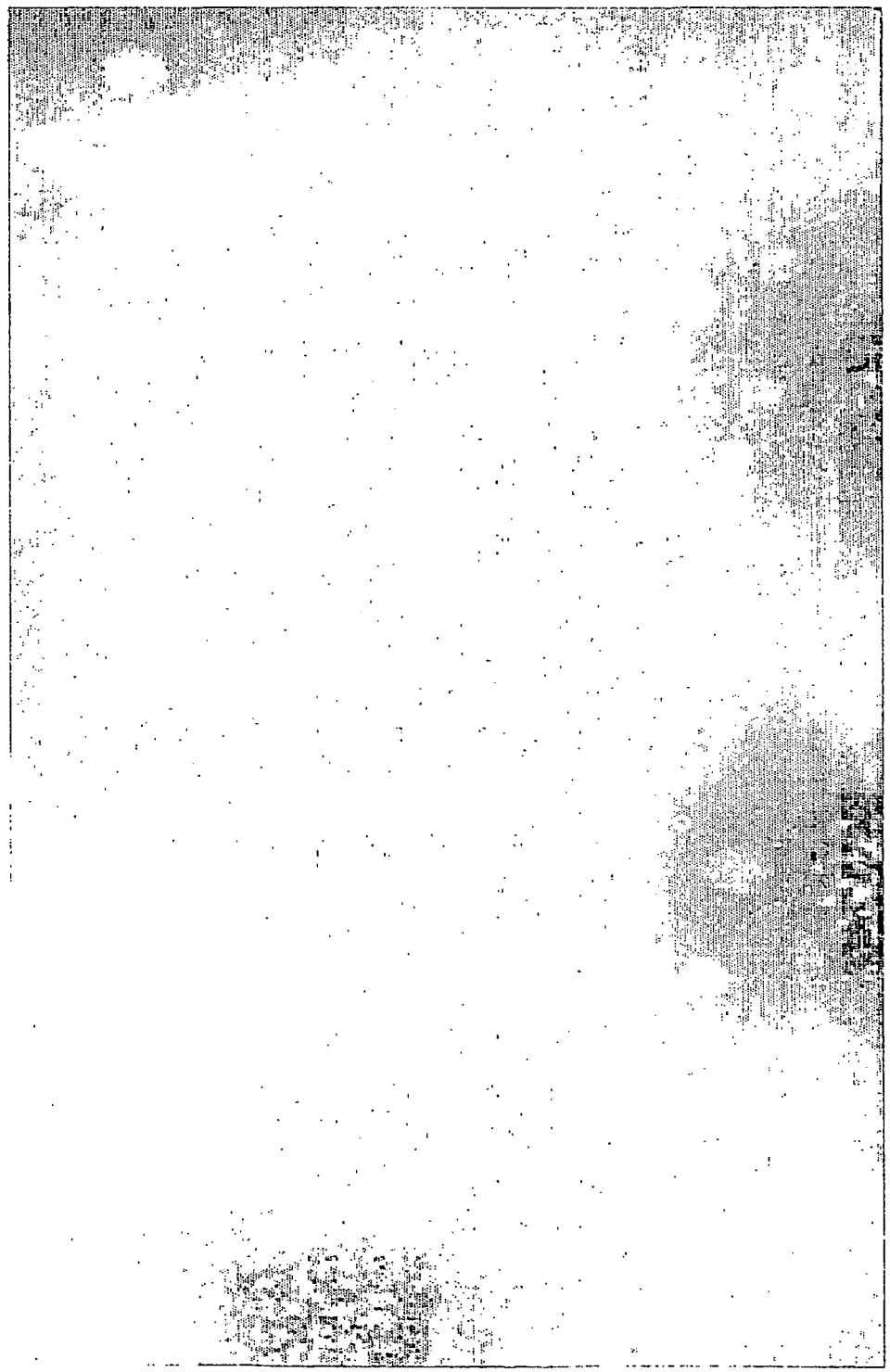
FIG. 4 is a TEM (transmission electron microscopy) photograph of vesicles made from Derivative 1.

Derivative 1 or Derivative 5 or dipalmytoylphosphatidyl choline (DPPC) was (50 mg) dissolved in 1 ml ethanol. 100 µl of this solution was injected under the surface of 2 ml of 0.01M Tris buffer pH 6.8 and 0.15M NaCl at room temperature under constant stirring. The resulting solution was sonicated (320 W) for 30 min at 25° C. Vesicles in a diameter range of 20-30 nm were obtained as visualized by transmission electron microscopy (TEM). Vesicles obtained from Derivative 1 are shown in FIG. 4.

REFERENCES

Benita, Simon (editor), "Microencapsulation Methods and Industrial Applications", Marcel Dekker, Inc. (1996)

Boder, H., Ringdorf, H., Skura, J. "Liposomes from Polymerizable Glycolipids", Angew. Chem. Int. Ed. Engl. 20, 91-92 (1981)

Chopineau, J. et. al, 1998. Monoacylation of ribonuclease. Journal of Controlled Release 56: 231-237

Fendler, J. Membrane Mimetic Chemistry, "Vesicles", Chapter 6, pp. 113-183, John Wiley & Sons (1982)

Fuhrhop J-H., Mathieu, J., "Routes to Functional Vesicle Membranes without Proteins", Angew. Chem. Int. Ed. Engl. 23, 100-113 (1984)

Grinberg, S.; Kolot, V.; Mills, D., Industrial Crops and Products, 3, 113-119 (1994)

Hanby, W E and S. G. Waley and J. Watson, J. Chem. Soc. 1950, 3239

Kozler, P. 2001. Osmotic opening of the hematoencephalic barrier in experiments. Rozhl Chir. 2001 80(8):393-396).

Kunitake, T.; Okahata, Y. J., "Totally Synthetic Bilayer Membranes", J. Am. Chem. Soc., 99, 3860-3861 (1977)

Kunitake, T.; Okahata, Y. J., J. Am. Chem. Soc., 102, 549 (1980)

Kunitake, T., N. Nak, K. K. Takarabe, M. Nagai, A. Tsuge and H. Yanagi, "Vesicles of Polymeric Bilayer and Monolayer Membranes", J. Am. Chem. Soc., 103, 5945-5947 (1981a)

Kunitake, T., Okahata, Y. J., Shimomura, M., Yasunami, S., "Formation of Stable Bilayer Assemblies in Water from Single Chain Amphiphiles. Relationship Between the Amphiphiles Structure and Aggregate Morphology", J. Am. Chem. Soc., 103, 5401-5413 (1981b)

Lasic, D. D. 1996. "Stealth Liposomes" In S. Benita (see above), Chapter 11, p. 302

Lasic, D. D. 1991. Novel Applications of Liposomes, Trends in Biotechnology, 16:307

Lee et al., 2001. Drug transporters in the CNS. Pharmacol. Review 53(4) 569-596

Menger, F M and D E Johnston, Jr. 1991. Specific Enzyme-Induced Decapsulation J Am Chem Soc 113: 5467-5468

Naoi, and Yagi K, et. al, 1980. Incorporation of enzymes through blood brain barrier into the brain by means of liposomes. Biochem. Int. 1: 591-596

Pak C C, Ali S, Janoff A S, Meers P. 1998. Triggerable liposomal fusion by enzyme cleavage of a novel-peptide-lipid conjugate. Biochim Biophys Acta, 1372: 13-27

Pardridge W M, 2001. Brain drug targeting and gene technologies. Jpn. J. Pharmacol. 87(2) 97-103

Patel, D. et. al, 1997. Peptide targeting and delivery across the BBB utilizing synthetic triglycerides esters: Design, synthesis and bioactivity. Conjugate Chem 8: 434-441

Shi, N. et al., 2001. Brain-specific expression of an exogenous gene after iv administration. Proc Nat Acad Soc USA 98(22):12754-12759

Toshinori and J. Sunamoto, "Recent Aspects in the Use of Liposomes in Biotechnology and Medicine", Prog. Lipid Res., 31:345 (1992)

Umezawa, F., and Eto Y. 1988. Liposome targeting to mouse brain: Mannose as a recognition marker. Biochem Biophysic Res. Commun. 153: 1038-1044

Widmer, J. and W. Keller-Schierlein. 1974. Helw. Chim. Acta 57: 657

Wolf F A and Brett G M. 2000. Ligand binding proteins and their potential. Pharmacol Review 52(2): 207-236

Yagi, K., et. al, 1982. Incorporation of enzymes into the brain by means of liposomes of novel composition. J Appl Bio Chem 4: 121-125

Yang C. et al., 2001. Prodrug-based optimal drug delivery via membrane transporters. Expert Opin. Biol. Ther. 1(2): 159-175

SCHEME 1
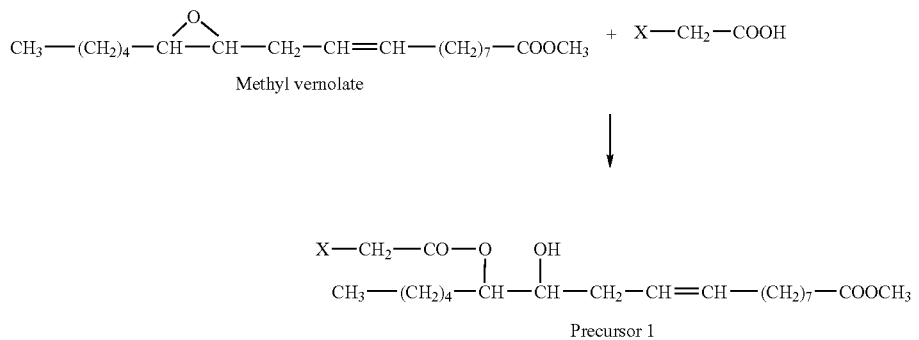
X = Cl, Br
SCHEME 2
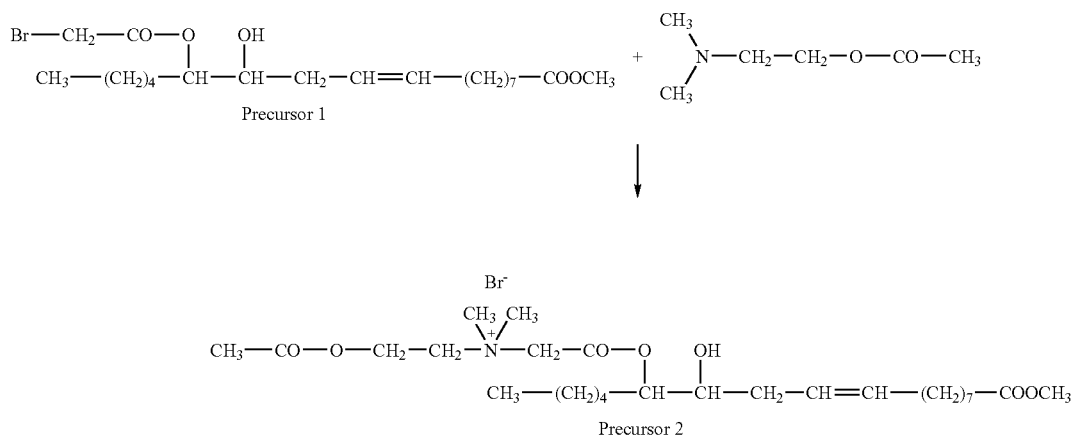
SCHEME 3
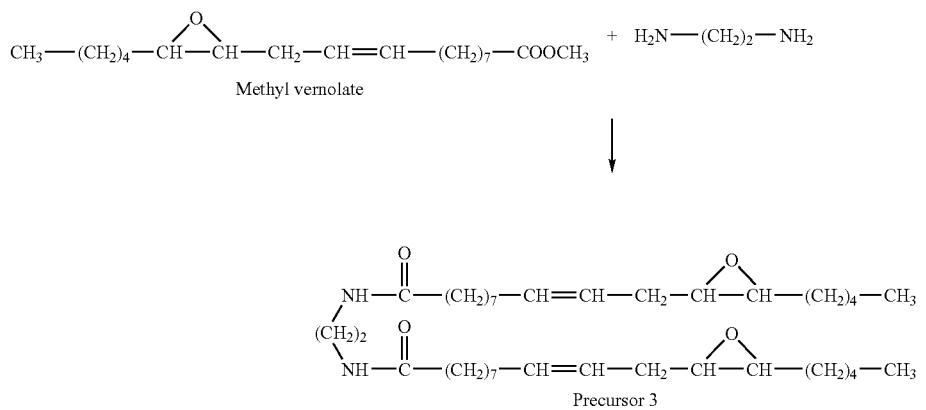

SCHEME 4
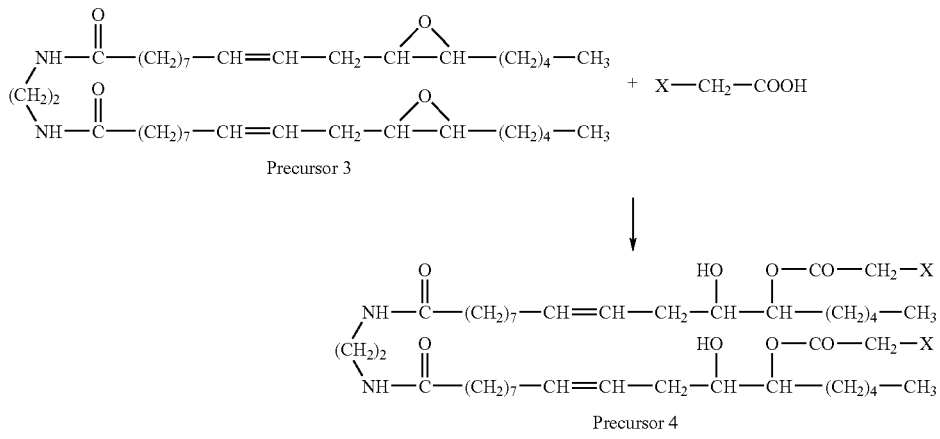
Precursor 3
X = Cl, Br, I
Precursor 4
SCHEME 5
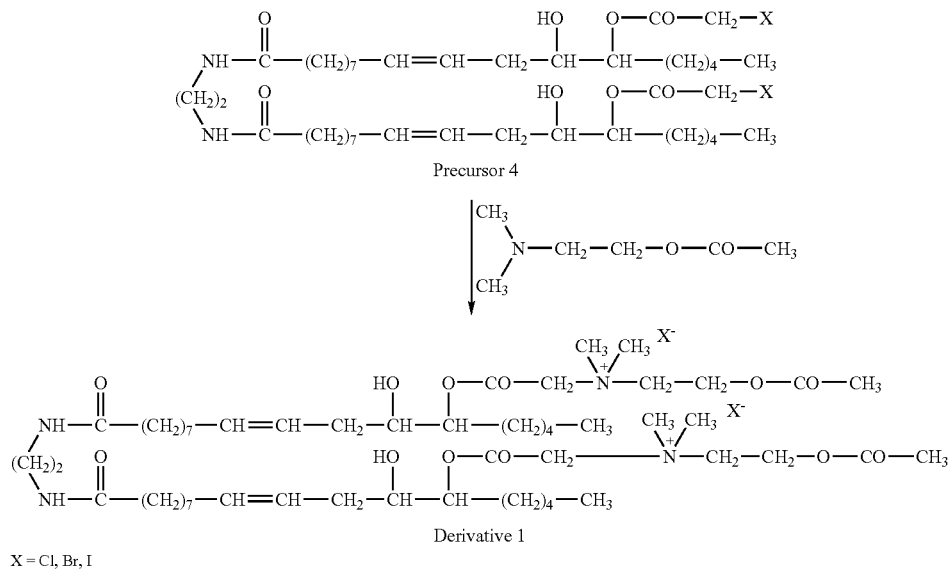
Precursor 4
Derivative 1
X = Cl, Br, I
SCHEME 6
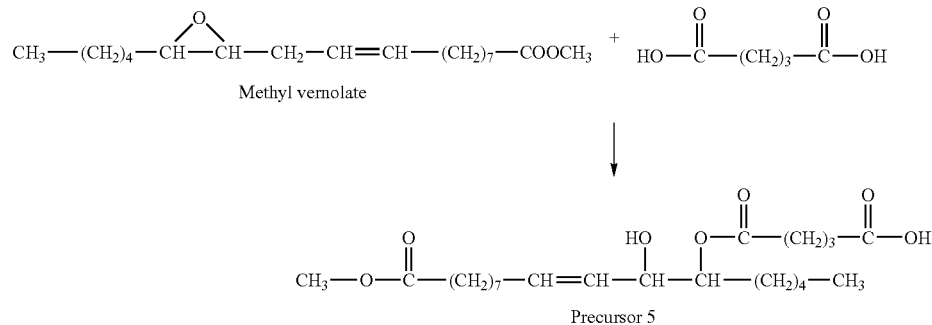
Methyl vernolate
Precursor 5

SCHEME 7
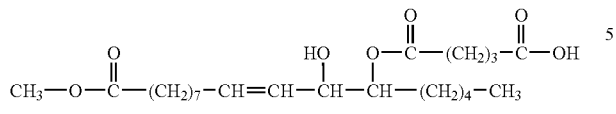
Precursor 5
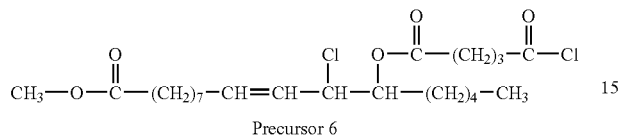
Precursor 6
SCHEME 8
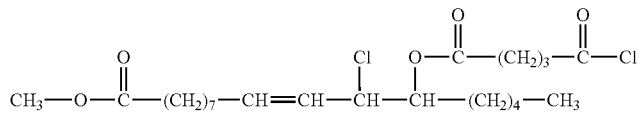
Precursor 6
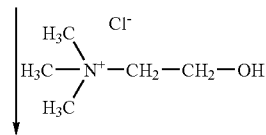
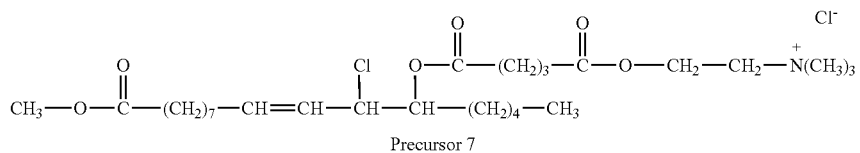
Precursor 7
SCHEME 9
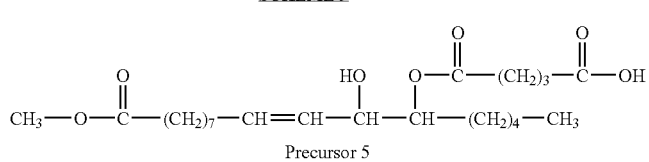
Precursor 5
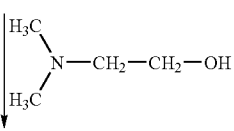
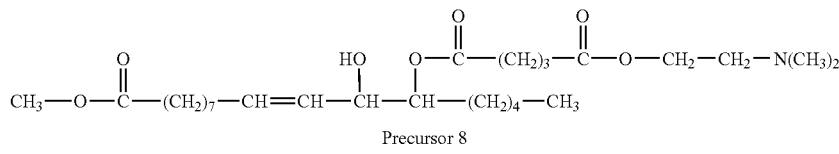
Precursor 8

SCHEME 10
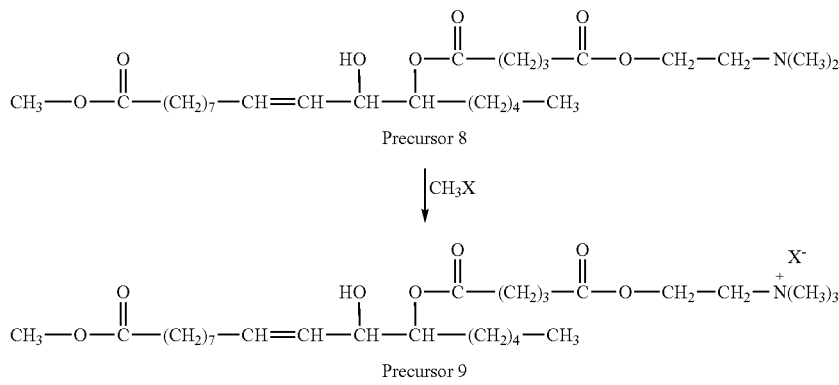
X = Cl, I
SCHEME 11
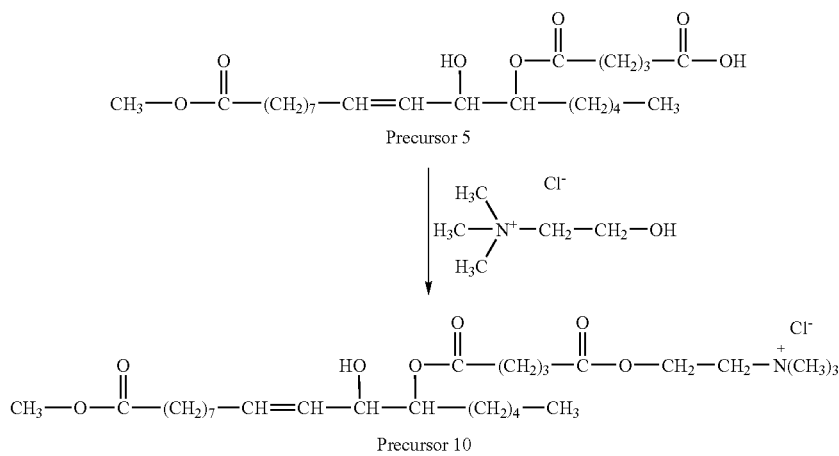
SCHEME 12
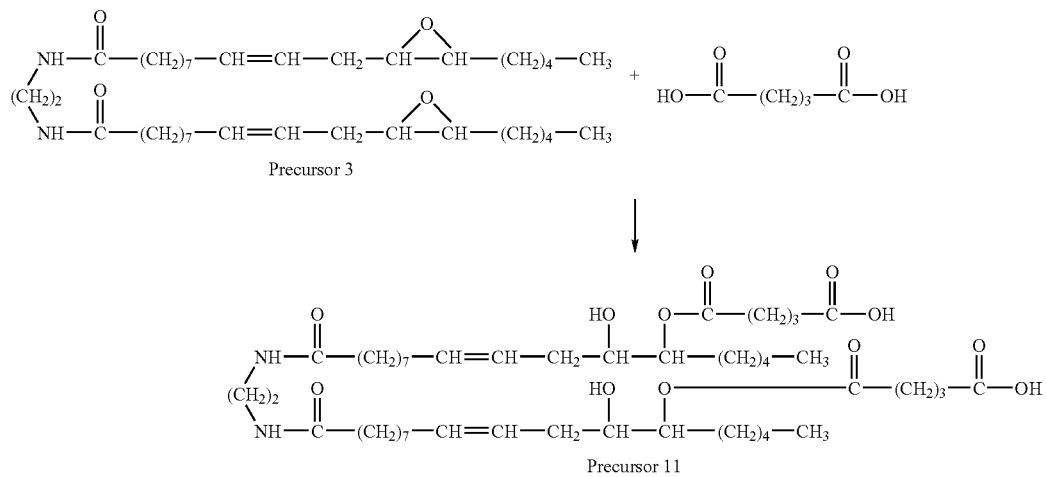

SCHEME 13
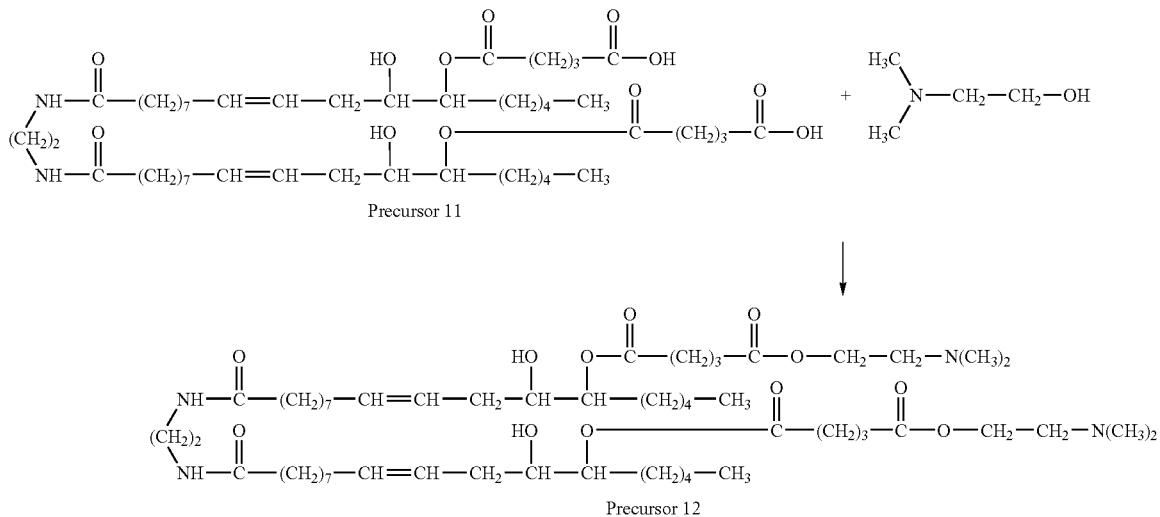
Precursor 11
SCHEME 14
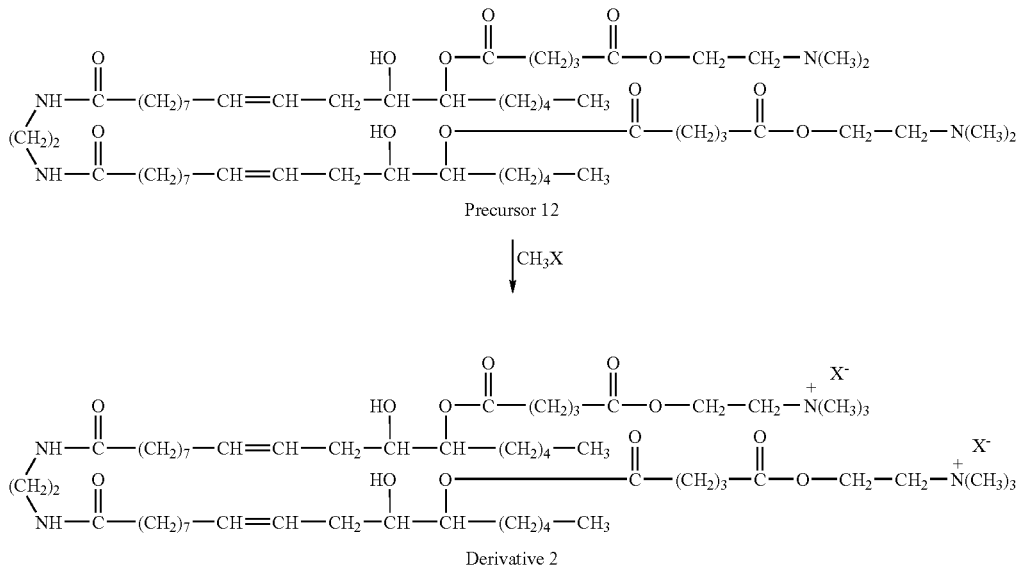
Derivative 2
X = Cl⁻, Br⁻, I⁻
SCHEME 15
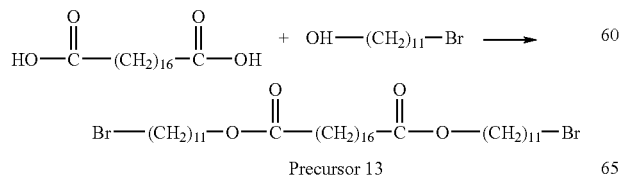
Precursor 13

SCHEME 16
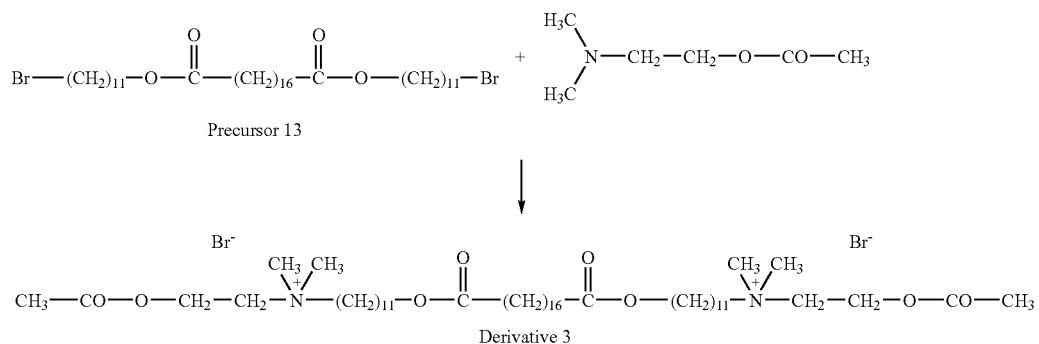
SCHEME 17
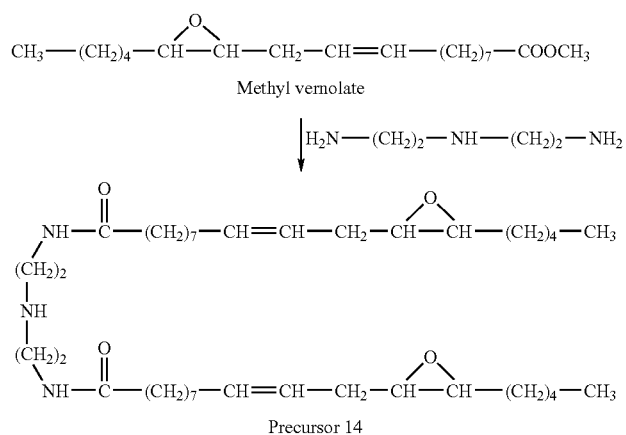
SCHEME 18
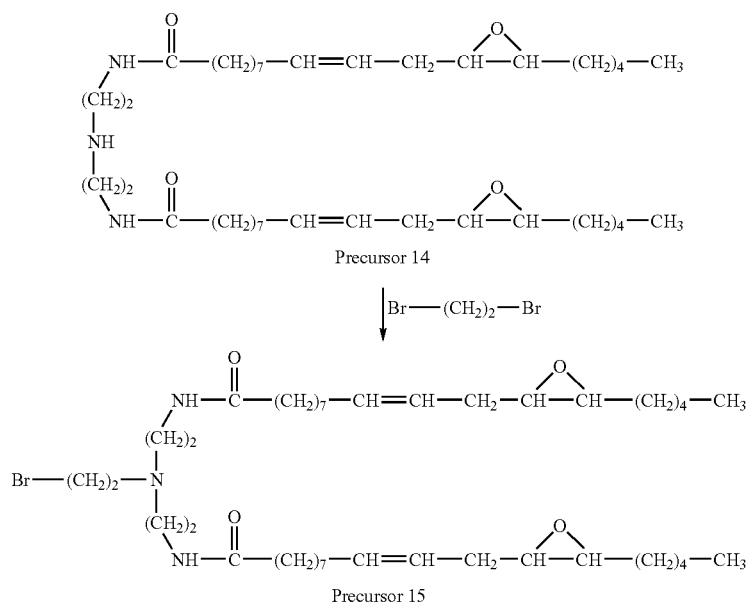

SCHEME 19
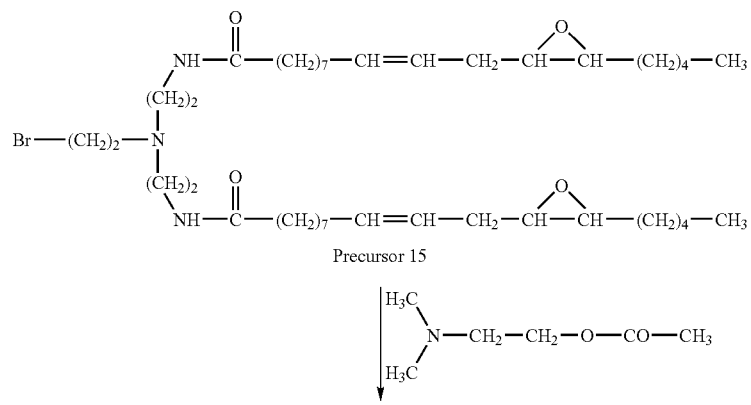
SCHEME 20
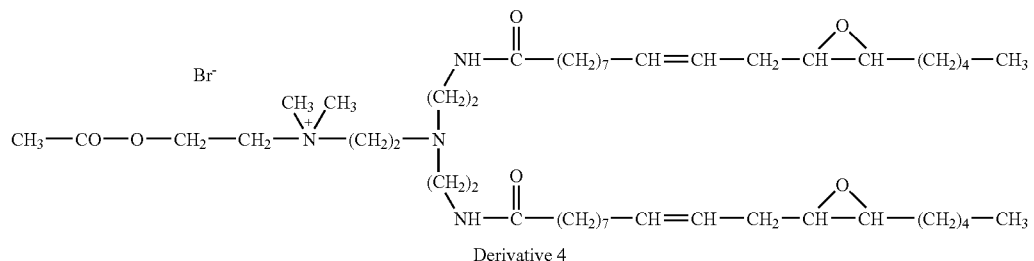
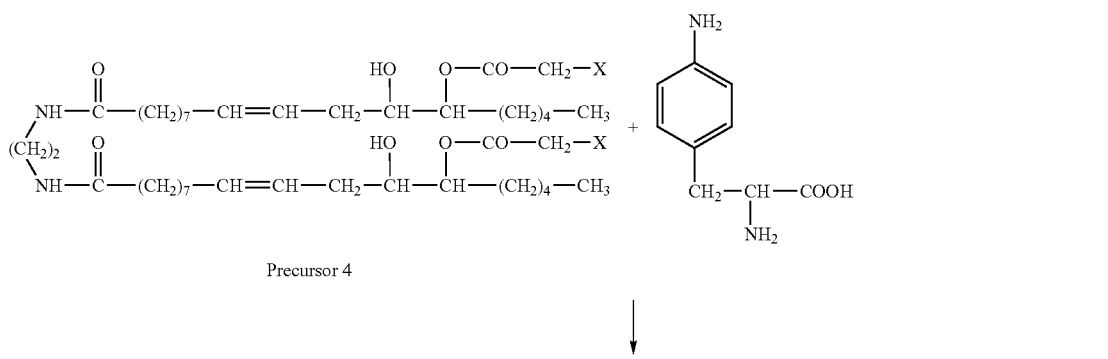
X = Cl⁻, Br⁻, I⁻

SCHEME 21
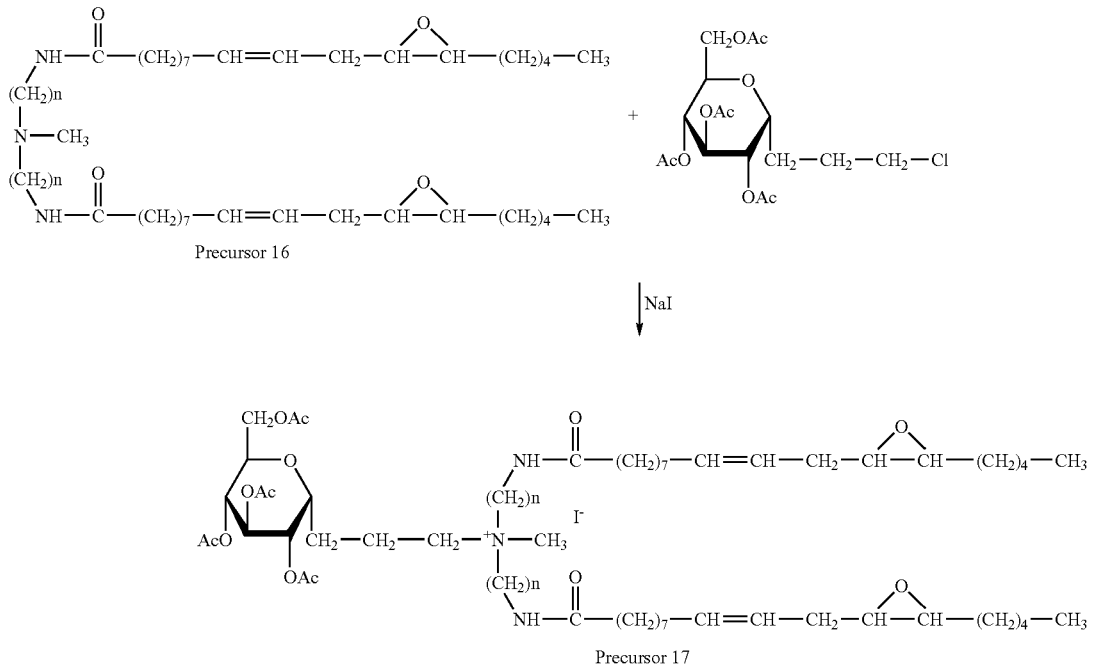
X = Cl⁻, I⁻
SCHEME 22
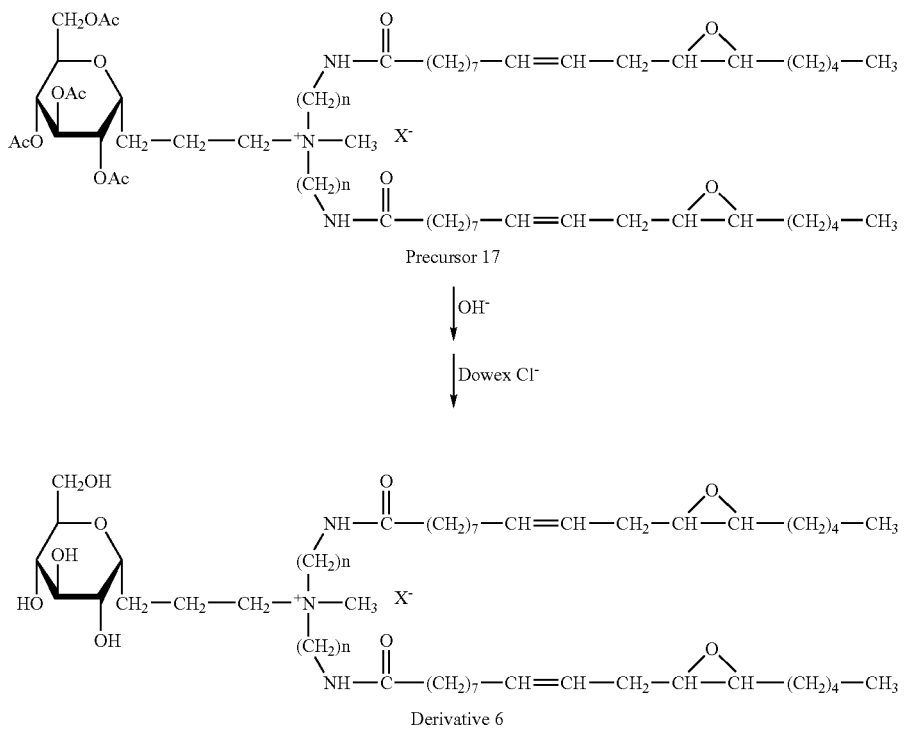

SCHEME 23
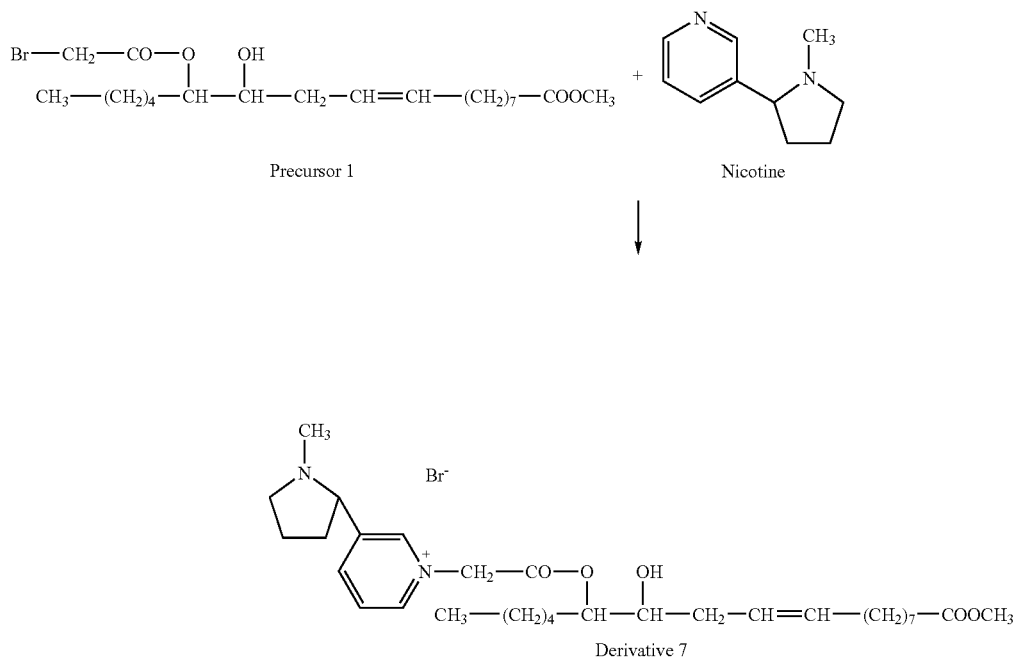
SCHEME 24
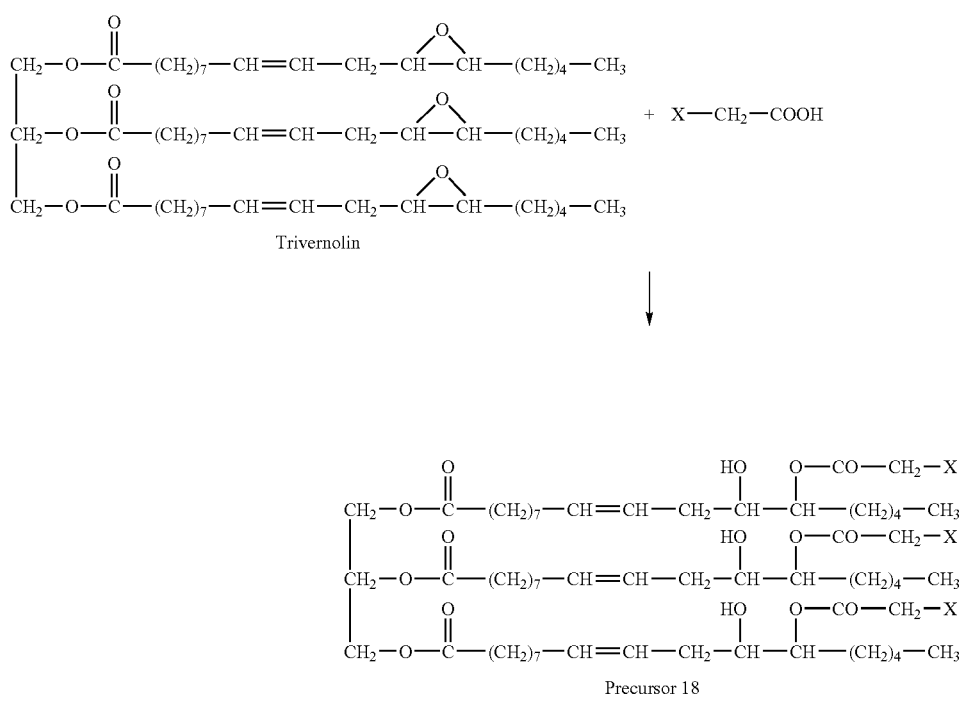
X = Cl, Br, I

SCHEME 25
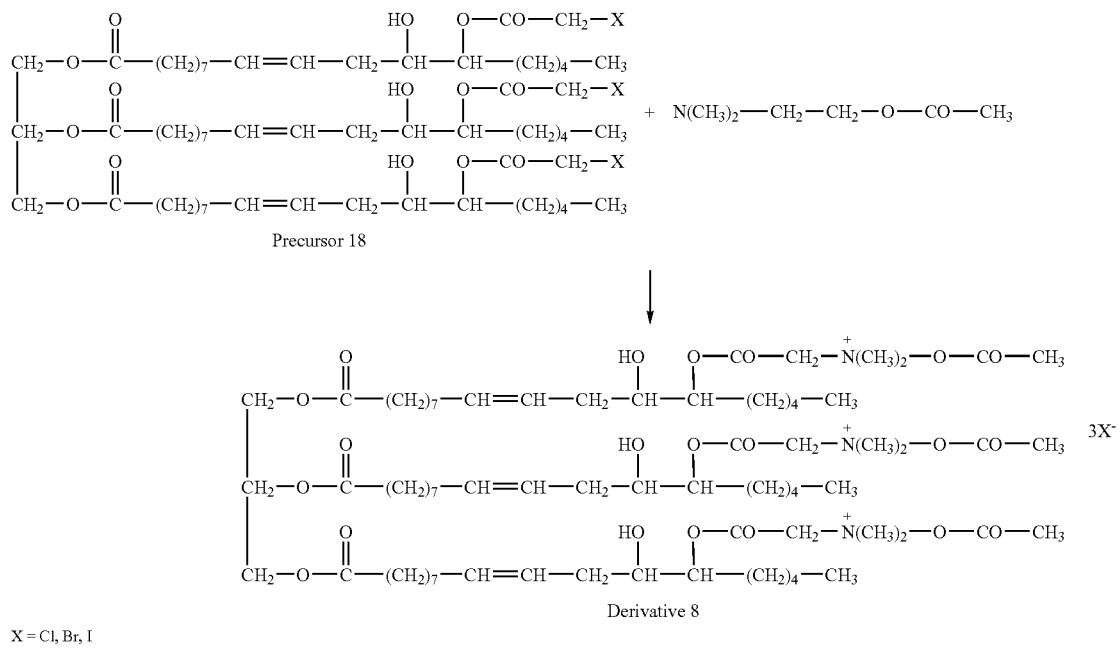
X = Cl, Br, I
SCHEME 26
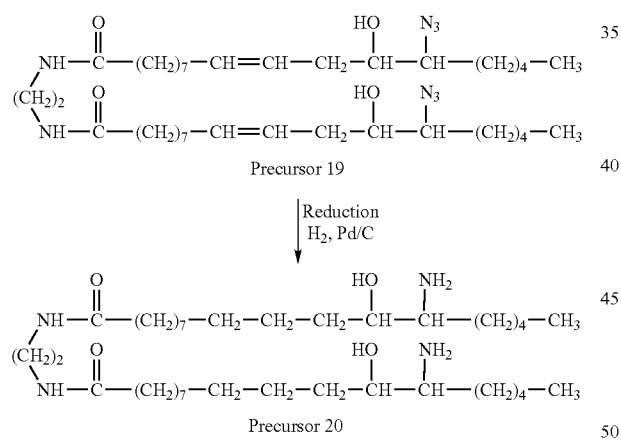
SCHEME 27
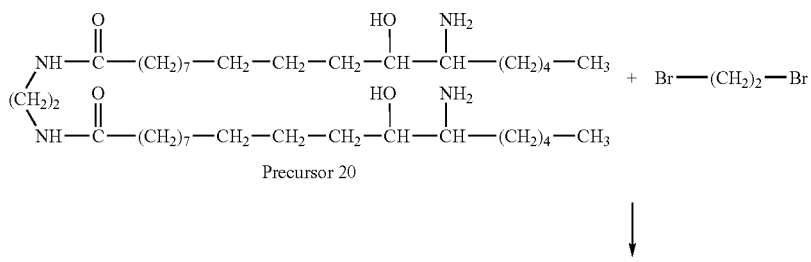

-continued
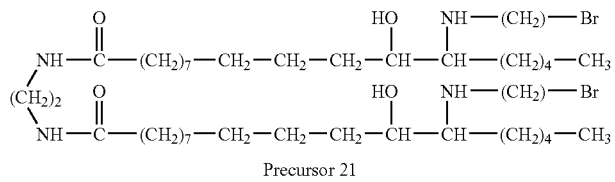
Precursor 21
SCHEME 28
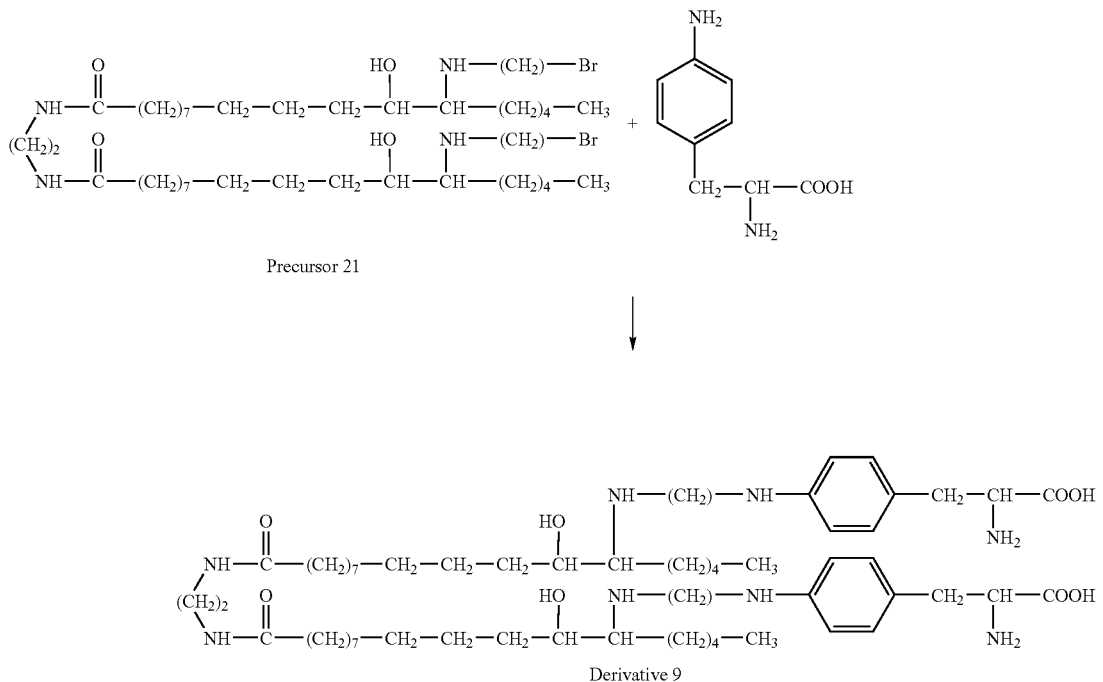
SCHEME 29
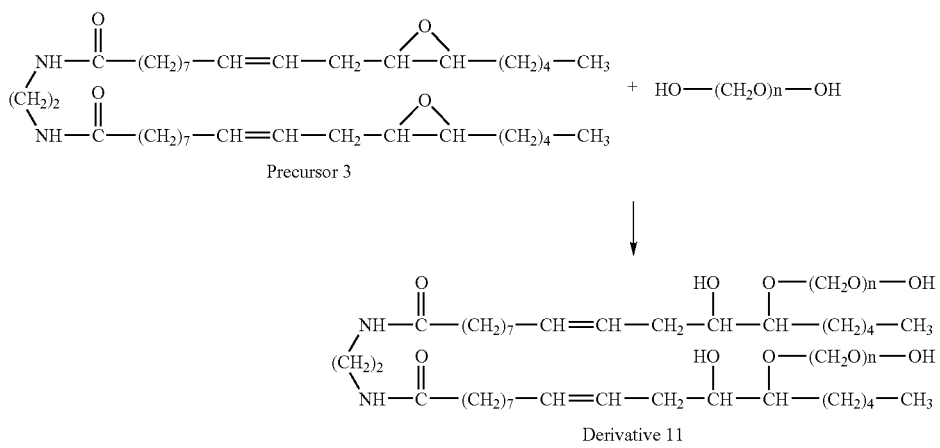

SCHEME 30

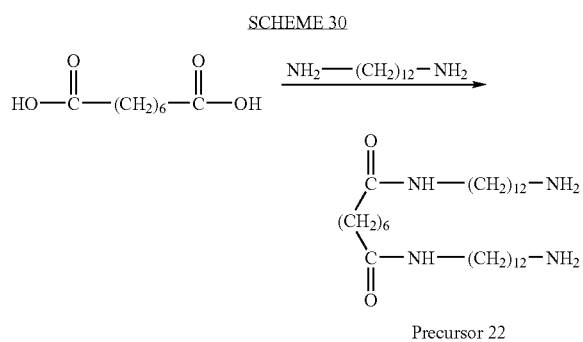

Precursor 22

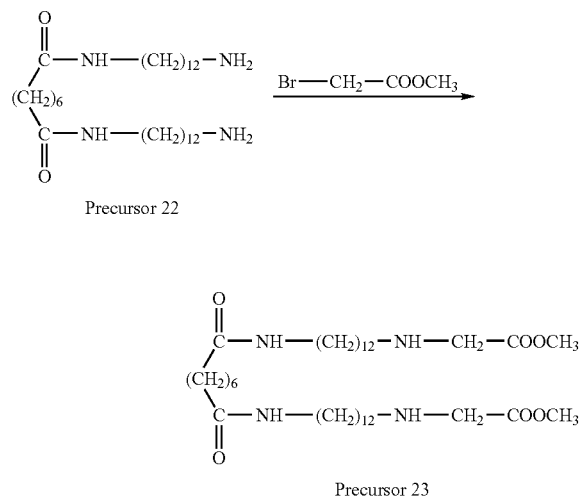

Precursor 23

SCHEME 31

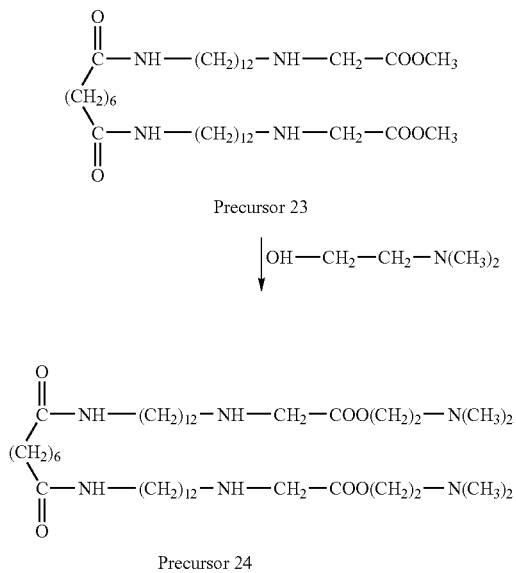

Precursor 24

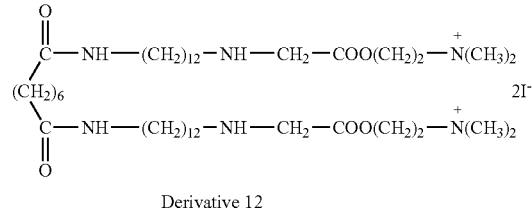

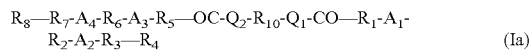

Derivative 12

The invention claimed is:

1. An amphiphilic compound capable of forming vesicles or liposomes, of the formula Ia:

$$R_8-R_7-A_4-R_6-A_3-R_5-OC-Q_2-R_{10}-Q_1-CO-R_1-A_1-R_2-A_2-R_3-R_4 \quad \text{(Ia)}$$

wherein:

$R_1$ and $R_5$, the same or different, each is $-(CH_2)_n-$;

$A_1$ is selected from the group consisting of $-(CH_2)_{m+2}-$, $-CH=CH-(CH_2)_m-$, $-CH=CH-CH(Y_1)-$, $-CH_2-CH_2-CH(Y_1)-$, $(-CH_2-CH(Y_1)-(CH_2)_m-$, $-CH(Y_1)-CH_2-(CH_2)_m-$, $-CH(Y_1)-CH(Y_2)-(CH_2)_m-$, wherein $Y_1$ and $Y_2$ each is halogen, $-OH$, $-O-CO-(CH_2)_m-Y_3$, $-NH-CO-Y_3$, $-SH$, $-SR_{11}$, $-NH_2$, or $-N(R_{11})(R_{12})$, or $Y_1$ and $Y_2$ together with the carbon atoms to which they are attached form a 2,3-oxiranylene group; and $Y_3$ is halogen, $-OH$, $-SH$, $-NH_2$, or $-N(R_{11})(R_{12})$;

$R_2$ and $R_6$, the same or different, each is $C_1$-$C_4$ alkylene, unsubstituted or substituted by halogen, amino or hydroxy;

$A_2$ is $-CH(R_{13})-$, $-CH_2-CH(R_{13})-$, $-CH(R_{13})-CH_2-$, $-CH(OH)-CH(R_{13})-$, $-CH(R_{13})-CH(OH)-$, $-CH(OH)-CH_2-CH(OH)-CH(R_{13})-$, $-CH(OH)-CH_2-CH(R_{13})-CH(OH)-$, $-G1-(C_6-C_{14}\text{ arylene})-(CH_2)_qR_{14}$, $-N(CH_3)_2R_{14}$, or $-SR_{14}$;

$R_3$ and $R_7$, the same or different, each is $-(CH_2)_o-$;

$R_4$ is H or $CH_3$, and wherein the total sum of carbon atoms in the $R_1$-$A_1$-$R_2$-$A_2$-$R_3$-$R_4$ chain is at most 23;

$Q_1$ is $-NH-$, $-O-$, $-S-$, or $-O-PO(OH)-O-$;

$Q_2$ is $-NH-$, $-O-$, $-S-$, or $-O-PO(OH)-O-$;

$R_{10}$ is $-(CH_2)_p-$; $-CH_2(CH_3)-(CH_2)_p-$; $-CH(CH_3)-(CH_2)_p-CH(CH_3)-$; $-(CH_2-CH_2-O-)_p-CH_2-CH_2-$; $-(CH_2-CH_2-S-)_p-CH_2-CH_2-$; $-(CH_2-CH_2-NH-)_p-CH_2-CH_2-$; $-C_6$-$C_{14}$ arylene-; $-(C_6$-$C_{14}$ arylene)-R-$(C_6$-$C_{14}$ arylene), wherein R is $C_1$-$C_4$ alkylene, $-C(CH_3)_2-$, $-O-$, $-S-$, $-NH-$ or $-SO_2-$;

$A_3$ is as defined for $A_1$, or is $-(CH_2)_m$, phenyl or $-CH_2$-phenyl, wherein the phenyl ring is unsubstituted or substituted by $C_1$-$C_4$ alkyl, halogen or both;

$A_4$ is as defined for $A_2$, or is $-(CH_2)_m-$;

$R_8$ is as defined for $R_4$;

$R_{13}$ is -G1-$(CH_2)_mR_{14}$ or -G1-$CO(CH_2)_mR_{14}$;

G1 is $-O-$, $-S-$, $-NR''-$, $-CH2NR''-$, $-CH2S-$, $-CH2O-$, $-NH-CO-$, $-O-CO-NH-$, $-NH-CO-NH-$, $-C=NO-$, or $-C(NH2)=NO-$, wherein R'' is H or $C_1$-$C_{18}$ alkyl;

$R_{14}$ is either a headgroup containing a selectively cleavable group or moiety, or is as defined for $R_{15}$ or for $R_{15}$ substituted by a selectively cleavable group or moiety;

$R_{11}$ and $R_{12}$, the same or different, each is $C_1$-$C_{18}$ alkyl unsubstituted or substituted by halogen; phenyl or $-CH_2$-phenyl, wherein the phenyl ring is unsubstituted or substituted by $C_1$-$C_4$-alkyl, halogen, or both, and wherein one of $R_{11}$ and $R_{12}$ may be H;

$R_{15}$ is —$NH_2$; —$NR_{11}R_{12}$; —$N^+R_{11}R_{12}R_{16}$ wherein $R_{16}$ is as defined for $R_{11}$ and $R_{12}$; —O—CO—($C_2$-$C_6$ alkenyl); —O—CO—$(CH_2)_t$—$NR_{11}R_{12}$; —O—CO—$(CH_2)_t$—$N^+R_{11}R_{12}R_{16}$; —O—CO—$(CH_2)_t$—COOH; —O—CO—$(CH_2)_t$—$SO_3H$; —O—CO—$(CH_2)_t$—O—PO(OH)$_2$; —NH—$(CH_2)_r$—COOH; —NH—$(CH_2)_r$—$SO_3H$; —NH—$(CH_2)_r$—O—PO(OH)$_2$; —NH—PO(OH)$_2$; —$N^+(CH_3)_2$—$R_{17}$; —O—PO(OH)—O—$(CH_2)_2$—$N^+R_{11}R_{12}R_{16}$; —O—PO(OH)—O—$(CH_2)_2$—$NH_3^+$; —O—PO(OH)—NH—PO(OH)—O—; —O—PO(OH)—O—$CH_2$—CH($NH_3^+$)—$COO^-$; —$CH_2$—CH=$CH_2$; —CO—CH=$CH_2$; —CO—C($CH_3$)=$CH_2$; —$(CH_2)_r$—COOH; —$(CH_2)_r$—O—$SO_2H$; —$(CH_2)_r$—O—PO(OH)$_2$; —$SR_{18}$; -G1-($C_6$-$C_{14}$ arylene)-$NR_{11}R_{12}$; -G1-($C_6$-$C_{14}$ arylene)-$N^+R_{11}R_{12}R_{16}$; -G1-($C_6$-$C_{14}$ arylene)-COOH; -G1-($C_6$-$C_{14}$ arylene)-$SO_3H$; -G1-($C_6$-$C_{14}$ arylene)-O—PO(OH)$_2$; -G1-($C_6$-$C_{14}$ arylene)-$(CH_2)_t$—$NR_{11}R_{12}$; -G1-($C_6$-$C_{14}$ arylene)-$(CH_2)_n$—$N^+R_{11}R_{12}R_{16}$; -G1-($C_6$-$C_{14}$ arylene)-$(CH_2)_t$—COOH; or -G1-($C_6$-$C_{14}$ arylene)-$(CH_2)_t$—$SO_3H$;

$R_{17}$ is —$CH_2$—CH=$CH_2$, —CO—CH=$CH_2$, —CO—C($CH_3$)=$CH_2$, —$(CH_2)_q$—$N^+R_{11}R_{12}R_{16}$, —$(CH_2)_q$—NH—$(CH_2)_q$—$SO_3H$, —$(CH_2)_q$—NH—$(CH_2)_q$—COOH, —$(CH_2)_q$—NH—$(CH_2)_q$—O—PO(OH)$_2$, —PO(OH)$_2$, or —O—PO(OH)—O—$(CH_2)_2$—$N^+R_{11}R_{12}R_{16}$;

$R_{18}$ is hydrogen, $C_1$-$C_{18}$ alkyl, $C_2$-$C_6$ alkenyl with a terminal double bond, —CO—CH=$CH_2$, or —CO—C($CH_3$)=CH—$NR_{11}R_{12}$;

n is an integer from 5 to 10; m is an integer from 0 to 4; o is an integer from 0 to 10; p is an integer from 1 to 16; q is an integer from 0 to 3; r is an integer from 1 to 6; and t is an integer from 1 to 14, and salts thereof;

wherein said amphiphilic compound of formula Ia has at least one radical $R_{14}$ which is a headgroup containing a selectively cleavable group or moiety and at least one hydrogen-bonding group located within said at least one headgroup, in close proximity thereto, or within and in close proximity to said at least one headgroup; and said selectively cleavable group or moiety is a group or moiety that is cleaved under selective conditions selected from the group consisting of change of chemical conditions, physical conditions, biological environment and combinations thereof.

2. An amphiphilic compound according to claim 1, wherein said selective conditions are selected from the group consisting of change of pH, change of temperature, oxidative conditions, reducing conditions, enzymatic conditions, and combinations thereof.

3. An amphiphilic compound according to claim 1, wherein said cleavable group is cleaved enzymatically in a biological environment.

4. An amphiphilic compound according to claim 3, wherein said biological environment is the brain or the blood.

5. An amphiphilic compound according to claim 1, wherein said selectively cleavable group or moiety is a residue of a derivative of a compound selected from the group consisting of choline, an aromatic amino acid, a dicarboxylic amino acid, a saccharide and a peptide that is specifically cleaved by an enzyme at a desired site.

6. An amphiphilic compound according to claim 5, wherein said derivative of choline is acetylcholine or acetylthiocholine; said aromatic amino acid is selected from the group consisting of phenylalanine, tyrosine, tryptophan and a derivative thereof selected from the group consisting of p-aminophenylalanine and levodopa; said dicarboxylic amino acid is glutamic acid or aspartic acid; said saccharide is glucose, galactose or mannose; and said peptide is enkephaline or N-acetyl-ala,ala.

7. An amphiphilic compound according to claim 1, wherein said hydrogen-bonding group is selected from the group consisting of —OH, —SH, —NH—, —$N^+H_2$—, —$NH_2$, —$N^+H_3$, —NH—CO—, —O—CO—NH—, —NH—CO—NH—, —C=NOH, —C($NH_2$)=NOH, —C($NH_2$)=NO— and —CO—$NH_2$.

8. An amphiphilic compound according to claim 1, capable of forming monolayer vesicles, of the formula Ia:

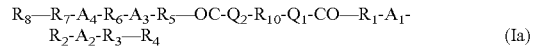

wherein:

$R_1$ and $R_5$ are each —$(CH_2)_7$;

$A_1$ is —CH=CH—$(CH_2)_m$—, wherein m is 0;

$R_2$ and $R_6$ each is —$CH_2$—;

$A_2$ is —CH(OH)—CH($R_{13}$)—;

$R_3$ and $R_7$ each is —$(CH_2)_4$—;

$R_4$ is $CH_3$, and wherein the total sum of carbon atoms in the $R_1$-$A_1$-$R_2$-$A_2$-$R_3$—$R_4$ chain is 17;

$Q_1$ is —NH—;

$Q_2$ is —NH—;

$R_{10}$ is —$(CH_2)_2$—;

$A_3$ is as defined for $A_1$;

$A_4$ is as defined for $A_2$;

$R_8$ is as defined for $R_4$;

$R_{13}$ is —O—$COCH_2$—$R_{14}$; and $R_{14}$ is a headgroup containing the selectively cleavable group or moiety —$N^+(CH_3)_2$—$CH_2$—$CH_2$—O—CO—$CH_3$;

and salts thereof.

9. An amphiphilic compound according to claim 1, selected from the group consisting of:

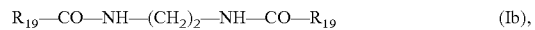

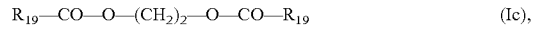

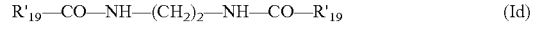

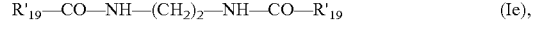

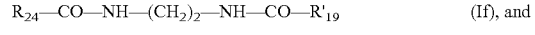

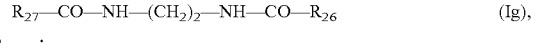

wherein $R_{19}$ is —$(CH_2)_7$—CH=CH—$CH_2$—CH(OH)—CH($R_{20}$)—$(CH_2)_4$—$CH_3$, $R'_{19}$ is —$(CH_2)_7$—CH=CH—$CH_2$—CH(OH)—CH($R_{21}$)—$(CH_2)_4$—$CH_3$, $R''_{19}$ is —$(CH_2)_7$—CH=CH—$CH_2$—CH(OH)—CH($R_{23}$)—$(CH_2)_4$—$CH_3$, $R_{20}$ is —$OCOCH_2CH_2$NH-phenyl-$CH_2$—CH($NH_2$)—COOH, $R_{21}$ is —NHCO—$CH_2CH_2$NH-phenyl-$CH_2$—CH($NH_2$)—COOH, $R_{23}$ is —NH—$CH_2CH_2$NH-phenyl-$CH_2$—CH($NH_2$)—COOH, $R_{24}$ is —$(CH_2)_7$—CH=CH—$CH_2$—CH(OH)—CH($R_{25}$)—$(CH_2)_4$—$CH_3$, $R_{25}$ is —NH—CO—$CH_2$—COOH, and $R_{26}$ and $R_{27}$ is each —$(CH_2)_{12}$—CH(OH)—$CH_2$—$R_{23}$.

10. An amphiphilic compound according to claim 1, selected from the group consisting of:

$$R_{28}-CO-NH-(CH_2)_2-NH-CO-R_{28} \quad (Ih),$$

$$R_{29}-CO-NH-(CH_2)_2-NH-CO-R_{29} \quad (Ii),$$

$$R_{31}-CO-NH-(CH_2)_2-NH-CO-R_{31} \quad (Ik),$$

$$R_{33}-CO-NH-(CH_2)_2-NH-CO-R_{31} \quad (Il),$$

$$R_{35}-CO-NH-(CH_2)_2-NH-CO-R_{35} \quad (Im),$$

$$R_{37}-CO-NH-(CH_2)_2-NH-CO-R_{37} \quad (In),$$

$$R_{39}-CO-NH-(CH_2)_2-NH-CO-R_{39} \quad (Io), \text{and}$$

$$R_{41}-CO-NH-(CH_2)_2-NH-CO-R_{41} \quad (Ip),$$

wherein
$R_{28}$ is $-(CH_2)_{12}-NHCH_2CH_2NH\text{-phenyl-}CH_2-CH(NH_2)COOH$,
$R_{29}$ is $-(CH_2)_{12}-NHCO-CH_2CH_2NH\text{-phenyl-}CH_2-CH(NH_2)COOH$,
$R_{31}$ is $-(CH_2)_{12}-R_{32}$,
$R_{32}$ is $-NHCH_2CH_2N^+(CH_3)_2-CH_2-CH_2-OCOCH_3$,
$R_{33}$ is $-(CH_2)_{12}-R_{34}$,
$R_{34}$ is $-NHCH_2CH_2N^+(CH_3)_3$,
$R_{35}$ is $-(CH_2)_9-CH=CH-CH_2-CH(R_{36})-(CH_2)_5CH_3$,
$R_{36}$ is $-OCH_2CH_2NH-CO-CH_2-CH_2-CH(NH_2)COOH$,
$R_{37}$ is $-(CH_2)_7-CH=CH-CH_2-CH(R_{38})-(CH_2)_5CH_3$,
$R_{38}$ is $-OCH_2CH_2NH\text{-phenyl-}CH_2-CH(NH_2)COOH$,
$R_{39}$ is $-(CH_2)_{12}-N(R_{40})CH_2CH_2NH\text{-phenyl-}CH_2-CH(NH_2)COOH$
$R_{40}$ is a $C_4$-$C_{16}$ alkyl, and
$R_{41}$ is $-(CH_2)_7-CH=CH-CH_2-CH(OR_{40})-CH(R_{38})-(CH_2)_4-CH_3$.

11. Vesicles or liposomes made from at least one amphiphilic compound according to claim 1.

12. Vesicles or liposomes according to claim 11, presenting one or more of the following characteristics:
(i) an ionic or polar headgroup attached to a hydrophobic chain, said headgroup containing a selectively cleavable group or moiety and a hydrogen-bonding group within the headgroup or in close proximity thereto;
(ii) two ionic or polar headgroups on opposite ends of the hydrophobic chain moiety, at least one containing a selectively cleavable group or moiety and a hydrogen-bonding group within the headgroup or in close proximity thereto, and optionally containing additional ionic and polar groups in proximity to the said headgroups, that do not hinder vesicle formation but which are capable of polar or hydrogen-bonding interactions that stabilize the vesicles which are made therefrom;
(iii) two headgroups on opposite ends of the molecule, at least one containing a selectively cleavable group or moiety and a hydrogen-bonding group within the headgroup or in close proximity thereto, and said headgroups may optionally contain additional polar groups within the center or in relative proximity to the midsection or center of the hydrophobic chain, capable of polar or hydrogen-bonding interactions that stabilize the vesicles which are made therefrom; and
(iv) in addition to (i) to (iii), additional aliphatic chain(s) of at least 5 methylene groups attached to the aforementioned hydrophobic chain moiety or to the headgroups to increase the hydrophobic interactions, and thus, contribute to the stability of vesicles which are made therefrom.

13. Vesicles or liposomes according to claim 11, being monolayered nanovesicles with asymmetric headgroups, made from double headed amphiphilic derivatives with two different polar or ionic headgroups on opposite sides of the aliphatic chains (bolaamphiphiles), wherein at least one of the said headgroups (the bulkier one) contains a group or moiety located on the outer vesicle surface, that can be selectively cleaved, and additional polar or ionic headgroups on the aliphatic chain(s) that give the vesicle additional stability, but nevertheless allow the vesicle to disrupt after removal of the ionic or polar headgroups.

14. Vesicles or liposomes according to claim 11, comprising a therapeutic substance encapsulated in, or loaded on, the vesicle or liposome.

15. Vesicles or liposomes according to claim 14, wherein said therapeutic substance is selected from the group consisting of levodopa (L-DOPA), a combination of carbidopa and levodopa, apomorphine, dopamine, and glial derived neurotrophic factor.

16. Vesicles or liposomes according to claim 14, wherein said therapeutic substance is a chemotherapeutic drug for chemotherapy of a brain tumor.

17. Vesicles or liposomes according to claim 14, for delivery of a therapeutic substance to the brain wherein said vesicles or liposomes further comprising amphiphilic compounds with headgroups containing targeting groups to the brain, groups for transport through the blood brain barrier, groups to stabilize the vesicles against clearance by the body, or combinations thereof.

18. Vesicles or liposomes according to claim 15, wherein said targeting groups to the brain are selected from the group consisting of residues of nicotine, cytosine, lobeline, L-glutamic acid, MK801, morphine, enkephaline, benzodiazepines, dopamine antagonists, tricyclic antidepressants, muscarinic agonists, muscarinic antagonists and cannabinoids.

19. Vesicles or liposomes according to claim 17, wherein said group for transport through the blood brain barrier is selected from the group consisting of glucose, mannose, and ascorbic acid, an antibody, choline, or an amino acid selected from the group consisting of glutamic acid, tryptophan and levodopa.

20. Vesicles or liposomes according to claim 17, wherein said groups to stabilize the vesicles against clearance by the body are polyethyleneglycol (PEG) residues.

21. Vesicles or liposomes according to claim 14, wherein said therapeutic substance has a short lifetime at the delivery site and exerts its activity in another part of the body.

22. Vesicles or liposomes according to claim 21, wherein said therapeutic substance is selected from the group consisting of insulin, copaxone, herceptin and a mixture of immunoglobulins.

23. The amphiphilic compounds herein designated as Derivatives 1, 2, 3, 4, 5, 8, 9 and 12 having the formulas

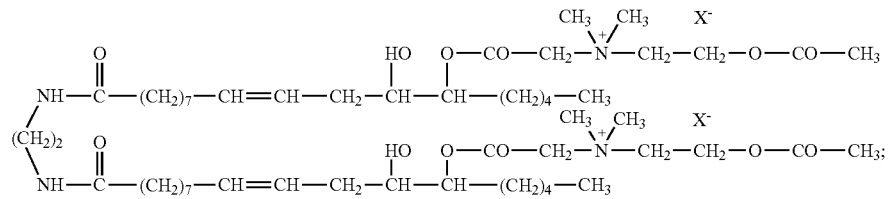
Derivative 1
X = Cl, Br, I
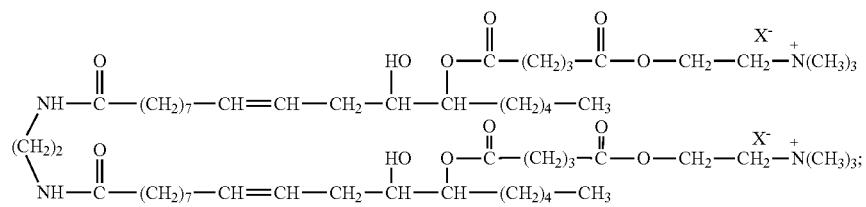
Derivative 2
X = Cl⁻, Br⁻, I⁻
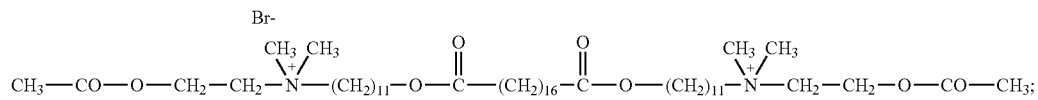
Derivative 3
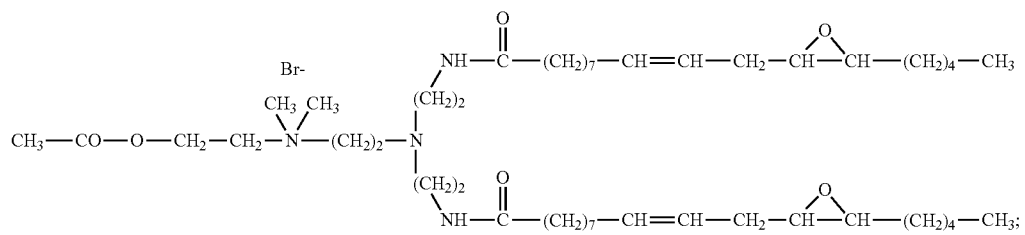
Derivative 4
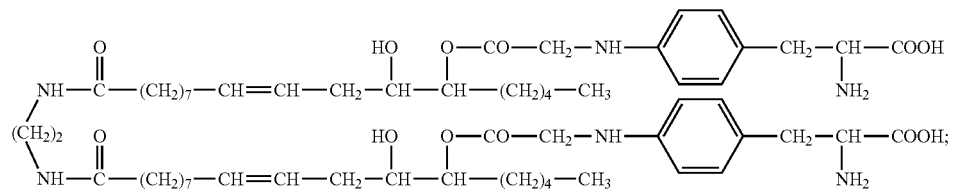
Derivative 5
X = Cl⁻, Br⁻, I⁻
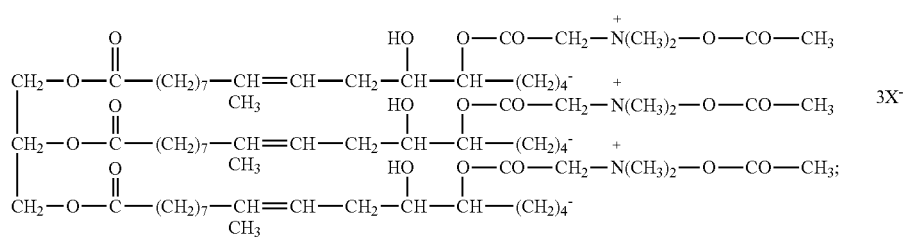
Derivative 8
X = Cl, Br, I -continued

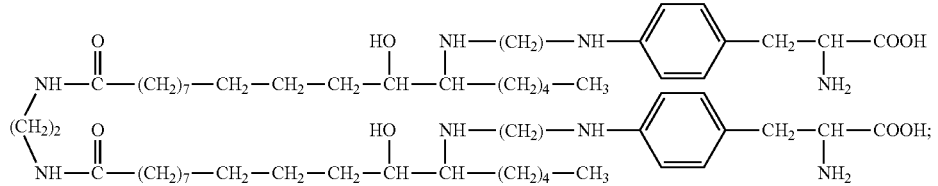

Derivative 9

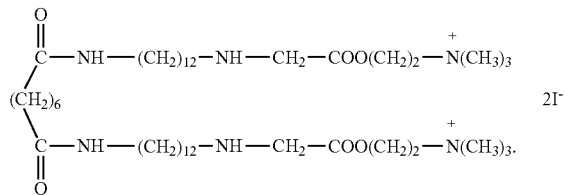

Derivative 12

24. The amphiphilic compounds herein designated as Derivatives 6, 10 and 11, as described at pages 68, 45 and 72 of the specification, respectively.

25. Vesicles or liposomes according to claim 14, wherein said therapeutic substance is selected from the group consisting of an antibody against components of Alzheimer plaques, an anti-inflammatory agent, a growth factor, and a muscarinic agonist.

* * * * *